(12) United States Patent
Haghgooie et al.

(10) Patent No.: US 10,835,163 B2
(45) Date of Patent: Nov. 17, 2020

(54) SYSTEMS AND METHODS FOR COLLECTING FLUID FROM A SUBJECT

(71) Applicant: Seventh Sense Biosystems, Inc., Medford, MA (US)

(72) Inventors: Ramin Haghgooie, Arlington, MA (US); Donald E. Chickering, III, Framingham, MA (US); Shawn Davis, Santa Monica, CA (US); Mark Michelman, Reading, MA (US); Li Yang Chu, Medford, MA (US)

(73) Assignee: Seventh Sense Biosystems, Inc., Medford, MA (US)

( * ) Notice: Subject to any disclaimer, the term of this patent is extended or adjusted under 35 U.S.C. 154(b) by 636 days.

(21) Appl. No.: 14/987,973

(22) Filed: Jan. 5, 2016

(65) Prior Publication Data

US 2016/0262676 A1 Sep. 15, 2016

Related U.S. Application Data

(63) Continuation of application No. 13/456,394, filed on Apr. 26, 2012, now Pat. No. 9,295,417.

(Continued)

(51) Int. Cl.
*A61B 5/15* (2006.01)
*A61B 5/151* (2006.01)
(Continued)

(52) U.S. Cl.
CPC ...... *A61B 5/150099* (2013.01); *A61B 5/1411* (2013.01); *A61B 5/14514* (2013.01);
(Continued)

(58) Field of Classification Search
CPC ... A61M 1/0001; A61M 35/00; A61B 5/1411; A61B 5/14514; A61B 5/150022;
(Continued)

(56) References Cited

U.S. PATENT DOCUMENTS 2,735,671 A 2/1956 Kuhn
2,961,233 A 11/1960 Ullrich
(Continued)

FOREIGN PATENT DOCUMENTS

CN 2065878 U 11/1990
CN 1222334 A 7/1999
(Continued)

OTHER PUBLICATIONS

European Office Action dated Jun. 30, 2015 for Application No. 12719217.7.
(Continued)

*Primary Examiner* — Benjamin J Klein
(74) *Attorney, Agent, or Firm* — Wolf, Greenfield & Sacks, P.C.

(57) ABSTRACT

Systems and methods for delivering to and/or receiving fluids or other materials, such as blood or interstitial fluid, from subjects, e.g., from the skin. Beading disruptors and/or capillaries may be used for facilitating the transport of fluids from a subject into a device. Beading disruptors may disrupt the "pooling" of bodily fluids such as blood on the surface of the skin and help influence flow in a desired way. A capillary may conduct flow of fluid in the device, e.g., to an inlet of a channel or other flow path that leads to a storage chamber. A vacuum (reduced pressure relative to ambient) may be used to receive fluid into the device, e.g., by using relatively low pressure to draw fluid into the inlet of a channel leading to a storage chamber. The vacuum source may be part of the device and have a volume that is larger than a recess of the fluid transporter that receives fluid from a surface.

21 Claims, 13 Drawing Sheets

Related U.S. Application Data

(60) Provisional application No. 61/480,960, filed on Apr. 29, 2011.

(51) Int. Cl.
*A61B 5/145* (2006.01)
*A61B 10/00* (2006.01)
*A61M 37/00* (2006.01)

(52) U.S. Cl.
CPC ........ *A61B 5/151* (2013.01); *A61B 5/150022* (2013.01); *A61B 5/150969* (2013.01); *A61B 5/150984* (2013.01); *A61B 10/0045* (2013.01); *A61M 37/0015* (2013.01); *A61B 5/150389* (2013.01); *A61B 5/150412* (2013.01); *A61B 5/150503* (2013.01); *A61B 2010/008* (2013.01); *A61M 2037/0007* (2013.01); *A61M 2037/0023* (2013.01); *A61M 2037/0061* (2013.01)

(58) Field of Classification Search
CPC ........ A61B 5/150099; A61B 5/150389; A61B 5/150412; A61B 5/150503; A61B 5/150969; A61B 5/150984
See application file for complete search history.

(56) References Cited

U.S. PATENT DOCUMENTS

| | | |
|---|---|---|
| 2,976,735 A | 3/1961 | Witte |
| 3,060,429 A | 10/1962 | Winston |
| 3,072,122 A | 1/1963 | Rosenthall |
| 3,339,546 A | 9/1967 | Chen |
| 3,519,171 A | 7/1970 | Kinnavy |
| 3,551,554 A | 12/1970 | Herschler |
| 3,645,253 A | 2/1972 | Goverde et al. |
| 3,711,602 A | 1/1973 | Herschler |
| 3,711,606 A | 1/1973 | Herschler |
| 3,740,421 A | 6/1973 | Schmolka |
| 3,761,013 A | 9/1973 | Schuster |
| 3,908,657 A | 9/1975 | Kowarski |
| 3,964,482 A | 6/1976 | Gerstel et al. |
| 4,103,684 A | 8/1978 | Ismach |
| 4,150,744 A | 4/1979 | Fennimore |
| 4,203,520 A | 5/1980 | Schuster |
| 4,253,460 A | 3/1981 | Chen et al. |
| 4,280,509 A | 7/1981 | Bethkenhagen et al. |
| 4,329,999 A | 5/1982 | Phillips |
| 4,340,067 A | 7/1982 | Rattenborg |
| 4,437,567 A | 3/1984 | Jeng |
| 4,537,776 A | 8/1985 | Cooper |
| 4,553,552 A | 11/1985 | Valdespino et al. |
| 4,557,943 A | 12/1985 | Rosler et al. |
| 4,572,210 A | 2/1986 | McKinnon |
| 4,615,697 A | 10/1986 | Robinson |
| 4,621,268 A | 11/1986 | Keeling et al. |
| 4,627,445 A | 12/1986 | Garcia et al. |
| 4,637,403 A | 1/1987 | Garcia et al. |
| 4,696,309 A | 9/1987 | Stephan |
| 4,706,676 A | 11/1987 | Peck |
| 4,740,365 A | 4/1988 | Yukimatsu et al. |
| 4,756,314 A | 7/1988 | Eckenhoff et al. |
| 4,764,378 A | 8/1988 | Keith et al. |
| 4,772,470 A | 9/1988 | Inoue et al. |
| 4,796,644 A | 1/1989 | Polaschegg |
| 4,820,720 A | 4/1989 | Sanders et al. |
| 4,821,733 A | 4/1989 | Peck |
| 4,855,298 A | 8/1989 | Yamada et al. |
| 4,856,533 A | 8/1989 | Anraku et al. |
| 4,863,970 A | 9/1989 | Patel et al. |
| 4,908,404 A | 3/1990 | Benedict et al. |
| 4,957,108 A | 9/1990 | Schoendorfer et al. |
| 4,971,068 A | 11/1990 | Sahi |
| 4,973,468 A | 11/1990 | Chiang et al. |
| 5,006,342 A | 4/1991 | Cleary et al. |
| 5,014,718 A | 5/1991 | Mitchen |
| 5,015,677 A | 5/1991 | Benedict et al. |
| 5,036,861 A | 8/1991 | Sembrowich et al. |
| 5,054,499 A | 10/1991 | Swierczek |
| 5,076,273 A | 12/1991 | Schoendorfer et al. |
| 5,108,927 A | 4/1992 | Dorn |
| 5,145,565 A | 9/1992 | Kater et al. |
| 5,161,532 A | 11/1992 | Joseph |
| 5,174,291 A | 12/1992 | Schoonen et al. |
| 5,201,324 A | 4/1993 | Swierczek |
| 5,213,568 A | 5/1993 | Lattin et al. |
| 5,231,993 A | 8/1993 | Haber et al. |
| 5,238,655 A | 8/1993 | Laible et al. |
| 5,279,294 A | 1/1994 | Anderson et al. |
| 5,320,607 A | 6/1994 | Ishibashi |
| 5,379,895 A | 1/1995 | Foslien |
| 5,402,798 A | 4/1995 | Swierczek et al. |
| 5,415,177 A | 5/1995 | Zadini et al. |
| 5,438,984 A | 8/1995 | Schoendorfer |
| 5,441,048 A | 8/1995 | Schoendorfer |
| 5,441,490 A | 8/1995 | Svedman |
| 5,443,080 A | 8/1995 | D'Angelo et al. |
| 5,445,611 A | 8/1995 | Eppstein et al. |
| 5,458,140 A | 10/1995 | Eppstein et al. |
| 5,504,011 A | 4/1996 | Gavin et al. |
| 5,505,212 A | 4/1996 | Keljmann et al. |
| 5,507,288 A | 4/1996 | Bocker et al. |
| 5,516,487 A | 5/1996 | Rosenthal et al. |
| 5,520,727 A | 5/1996 | Vreeland et al. |
| 5,529,581 A | 6/1996 | Cusack |
| 5,540,709 A | 7/1996 | Ramel |
| 5,552,118 A | 9/1996 | Mayer |
| 5,560,543 A | 10/1996 | Smith et al. |
| 5,574,134 A | 11/1996 | Waite |
| 5,580,794 A | 12/1996 | Allen |
| 5,582,184 A | 12/1996 | Erickson et al. |
| 5,636,640 A | 6/1997 | Staehlin |
| 5,638,815 A | 6/1997 | Schoendorfer |
| 5,662,127 A | 9/1997 | De Vaughn |
| 5,676,144 A | 10/1997 | Schoendorfer |
| 5,680,872 A | 10/1997 | Sesekura et al. |
| 5,682,233 A | 10/1997 | Brinda |
| 5,685,875 A | 11/1997 | Hlavinka et al. |
| 5,701,910 A | 12/1997 | Powles et al. |
| 5,714,390 A | 2/1998 | Hallowitz et al. |
| 5,741,138 A | 4/1998 | Rice et al. |
| 5,746,217 A | 5/1998 | Erickson et al. |
| 5,800,420 A | 9/1998 | Gross et al. |
| 5,807,375 A | 9/1998 | Gross et al. |
| 5,811,108 A | 9/1998 | Goeringer |
| 5,813,614 A | 9/1998 | Coffee |
| 5,817,011 A | 10/1998 | Schoendorfer |
| 5,817,012 A | 10/1998 | Schoendorfer |
| 5,820,570 A | 10/1998 | Erickson et al. |
| 5,820,622 A | 10/1998 | Gross et al. |
| 5,823,973 A | 10/1998 | Racchini et al. |
| 5,857,983 A | 1/1999 | Douglas et al. |
| 5,858,188 A | 1/1999 | Soane et al. |
| 5,873,900 A | 2/1999 | Maurer et al. |
| 5,876,675 A | 3/1999 | Kennedy |
| 5,879,310 A | 3/1999 | Sopp et al. |
| 5,879,311 A | 3/1999 | Duchon et al. |
| 5,879,367 A | 3/1999 | Latterell et al. |
| 5,885,211 A | 3/1999 | Eppstein et al. |
| 5,891,053 A | 4/1999 | Sesekura |
| 5,897,508 A | 4/1999 | Konrad |
| 5,944,662 A | 8/1999 | Schoendorfer |
| 5,951,492 A | 9/1999 | Douglas et al. |
| 5,951,493 A | 9/1999 | Douglas et al. |
| 5,955,096 A | 9/1999 | Santos et al. |
| 5,963,136 A | 10/1999 | O'Brien |
| 5,964,718 A | 10/1999 | Duchon et al. |
| 5,972,386 A | 10/1999 | Burgoyne |
| 5,985,312 A | 11/1999 | Jacob et al. |
| 5,998,588 A | 12/1999 | Hoffman et al. |
| 6,007,845 A | 12/1999 | Domb et al. |
| 6,015,392 A | 1/2000 | Douglas et al. |
| 6,024,710 A | 2/2000 | Miller et al. |

(56) References Cited

U.S. PATENT DOCUMENTS

| | | |
|---|---|---|
| 6,027,459 A | 2/2000 | Shain et al. |
| 6,040,135 A | 3/2000 | Tyrell |
| 6,044,303 A | 3/2000 | Agarwala et al. |
| 6,048,337 A | 4/2000 | Svedman |
| 6,050,988 A | 4/2000 | Zuck |
| 6,063,029 A | 5/2000 | Saita et al. |
| 6,063,039 A | 5/2000 | Cunningham et al. |
| 6,063,365 A | 5/2000 | Shefer et al. |
| 6,066,103 A | 5/2000 | Duchon et al. |
| 6,071,249 A | 6/2000 | Cunningham et al. |
| 6,071,250 A | 6/2000 | Douglas et al. |
| 6,071,251 A | 6/2000 | Cunningham et al. |
| 6,080,116 A | 6/2000 | Erickson et al. |
| 6,083,196 A | 7/2000 | Trautman et al. |
| 6,091,975 A | 7/2000 | Daddona et al. |
| 6,093,156 A | 7/2000 | Cunningham et al. |
| 6,099,484 A | 8/2000 | Douglas et al. |
| 6,107,102 A | 8/2000 | Ferrari |
| 6,126,899 A | 10/2000 | Woudenberg et al. |
| 6,132,449 A | 10/2000 | Lum et al. |
| 6,132,702 A | 10/2000 | Witt et al. |
| 6,133,318 A | 10/2000 | Hart |
| 6,152,889 A | 11/2000 | Sopp et al. |
| 6,152,942 A | 11/2000 | Brenneman et al. |
| 6,155,992 A | 12/2000 | Henning et al. |
| 6,162,639 A | 12/2000 | Douglas |
| 6,190,315 B1 | 2/2001 | Kost et al. |
| 6,192,890 B1 | 2/2001 | Levy et al. |
| 6,203,504 B1 | 3/2001 | Latterell et al. |
| 6,206,841 B1 | 3/2001 | Cunningham et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,234,990 B1 | 5/2001 | Rowe et al. |
| 6,235,313 B1 | 5/2001 | Mathiowitz et al. |
| 6,252,129 B1 | 6/2001 | Coffee |
| 6,261,245 B1 | 7/2001 | Kawai et al. |
| 6,267,724 B1 | 7/2001 | Taylor |
| 6,283,926 B1 | 9/2001 | Cunningham et al. |
| 6,306,104 B1 | 10/2001 | Cunningham et al. |
| 6,306,993 B1 | 10/2001 | Rothbard et al. |
| 6,309,887 B1 | 10/2001 | Ray |
| 6,319,210 B1 | 11/2001 | Douglas et al. |
| 6,322,574 B1 | 11/2001 | Llyod |
| 6,332,871 B1 | 12/2001 | Douglas et al. |
| 6,334,856 B1 | 1/2002 | Allen et al. |
| 6,340,354 B1 | 1/2002 | Rambin |
| 6,349,229 B1 | 2/2002 | Watanabe et al. |
| 6,349,850 B1 | 2/2002 | Cheikh |
| 6,361,944 B1 | 3/2002 | Mirkin et al. |
| 6,364,890 B1 | 4/2002 | Lum et al. |
| 6,379,317 B1 | 4/2002 | Kintzig et al. |
| 6,379,324 B1 | 4/2002 | Gartstein et al. |
| 6,391,471 B1 | 5/2002 | Hiraoka et al. |
| 6,406,919 B1 | 6/2002 | Tyrrell |
| 6,409,679 B2 | 6/2002 | Pyo |
| 6,436,078 B1 | 8/2002 | Svedman |
| 6,440,096 B1 | 8/2002 | Lastovich et al. |
| 6,455,324 B1 | 9/2002 | Douglas |
| 6,461,644 B1 | 10/2002 | Jackson et al. |
| 6,464,649 B1 | 10/2002 | Duchon et al. |
| 6,465,002 B1 | 10/2002 | Mathiowitz et al. |
| 6,485,439 B1 | 11/2002 | Roe et al. |
| 6,485,703 B1 | 11/2002 | Cote et al. |
| 6,491,657 B2 | 12/2002 | Rowe et al. |
| 6,491,902 B2 | 12/2002 | Shefer et al. |
| 6,501,976 B1 | 12/2002 | Sohrab |
| 6,502,697 B1 | 1/2003 | Crampton et al. |
| 6,503,209 B2 | 1/2003 | Hakky et al. |
| 6,503,231 B1 | 1/2003 | Prausnitz et al. |
| 6,506,168 B1 | 1/2003 | Fathallah et al. |
| 6,527,716 B1 | 3/2003 | Eppstein |
| 6,532,386 B2 | 3/2003 | Sun et al. |
| 6,537,243 B1 | 3/2003 | Henning et al. |
| 6,537,264 B1 | 3/2003 | Cormier et al. |
| 6,538,089 B1 | 3/2003 | Samra et al. |
| 6,540,675 B2 | 4/2003 | Aceti et al. |
| 6,548,264 B1 | 4/2003 | Tan et al. |
| 6,558,361 B1 | 5/2003 | Yeshurun |
| 6,562,014 B2 | 5/2003 | Lin et al. |
| 6,589,562 B1 | 7/2003 | Shefer et al. |
| 6,591,124 B2 | 7/2003 | Sherman et al. |
| 6,602,205 B1 | 8/2003 | Erickson et al. |
| 6,603,987 B2 | 8/2003 | Whitson |
| 6,607,495 B1 | 8/2003 | Skalak et al. |
| 6,607,513 B1 | 8/2003 | Down et al. |
| 6,611,707 B1 | 8/2003 | Prausnitz et al. |
| 6,614,522 B1 | 9/2003 | Sopp et al. |
| 6,620,123 B1 | 9/2003 | Mitragotri et al. |
| 6,624,882 B2 | 9/2003 | Sopp et al. |
| 6,626,884 B1 | 9/2003 | Dillon et al. |
| 6,629,057 B2 | 9/2003 | Zweig et al. |
| 6,652,478 B1 | 11/2003 | Gartstein et al. |
| 6,656,147 B1 | 12/2003 | Gertsek et al. |
| 6,660,527 B2 | 12/2003 | Stroup |
| 6,669,961 B2 | 12/2003 | Kim et al. |
| 6,678,554 B1 | 1/2004 | Sun et al. |
| 6,685,921 B2 | 2/2004 | Lawlor |
| 6,689,100 B2 | 2/2004 | Connelly et al. |
| 6,696,075 B2 | 2/2004 | Mathiowitz et al. |
| 6,706,000 B2 | 3/2004 | Perez et al. |
| 6,706,159 B2 | 3/2004 | Moerman et al. |
| 6,712,776 B2 | 3/2004 | Latterell et al. |
| 6,712,792 B2 | 3/2004 | Leong |
| 6,741,877 B1 | 5/2004 | Shults et al. |
| 6,743,211 B1 | 6/2004 | Prausnitz et al. |
| 6,749,575 B2 | 6/2004 | Matriano et al. |
| 6,765,081 B2 | 7/2004 | Lin et al. |
| 6,766,817 B2 | 7/2004 | da Silva |
| 6,768,920 B2 | 7/2004 | Lange et al. |
| 6,783,502 B2 | 8/2004 | Orloff et al. |
| 6,786,874 B2 | 9/2004 | Grace et al. |
| 6,793,633 B2 | 9/2004 | Douglas et al. |
| 6,798,920 B1 | 9/2004 | Wells et al. |
| 6,800,122 B2 | 10/2004 | Anderson et al. |
| 6,811,090 B2 | 11/2004 | Yogi et al. |
| 6,814,760 B2 | 11/2004 | Anderson et al. |
| 6,825,161 B2 | 11/2004 | Shefer et al. |
| 6,826,426 B2 | 11/2004 | Lange et al. |
| 6,837,858 B2 | 1/2005 | Cunningham et al. |
| 6,855,133 B2 | 2/2005 | Svedman |
| 6,860,873 B2 | 3/2005 | Allen et al. |
| 6,878,120 B2 | 4/2005 | Roe et al. |
| 6,896,666 B2 | 5/2005 | Kochamba |
| 6,899,851 B2 | 5/2005 | Allen et al. |
| 6,908,448 B2 | 6/2005 | Redding, Jr. |
| 6,918,404 B2 | 7/2005 | Dias da Silva |
| 6,918,901 B1 | 7/2005 | Theeuwes et al. |
| 6,923,764 B2 | 8/2005 | Aceti et al. |
| 6,925,317 B1 | 8/2005 | Samuels et al. |
| 6,931,277 B1 | 8/2005 | Yuzhakov et al. |
| 6,940,591 B2 | 9/2005 | Sopp et al. |
| 6,952,604 B2 | 10/2005 | DeNuzzio et al. |
| 6,969,351 B2 | 11/2005 | Knoll |
| 6,969,359 B2 | 11/2005 | Duchon et al. |
| 6,990,367 B2 | 1/2006 | Kiser et al. |
| 6,997,886 B2 | 2/2006 | Latterell et al. |
| 7,001,343 B2 | 2/2006 | Erickson et al. |
| 7,001,344 B2 | 2/2006 | Freeman et al. |
| 7,004,928 B2 | 2/2006 | Aceti et al. |
| 7,008,384 B2 | 3/2006 | Tapper |
| 7,014,615 B2 | 3/2006 | Erickson et al. |
| 7,025,774 B2 | 4/2006 | Freeman et al. |
| 7,037,277 B1 | 5/2006 | Smith et al. |
| 7,041,067 B2 | 5/2006 | Sopp et al. |
| 7,041,068 B2 | 5/2006 | Freeman et al. |
| 7,047,070 B2 | 5/2006 | Wilkinson et al. |
| 7,066,586 B2 | 6/2006 | da Silva |
| 7,066,885 B2 | 6/2006 | Erickson et al. |
| 7,097,631 B2 | 8/2006 | Trautman et al. |
| 7,131,987 B2 | 11/2006 | Sherman et al. |
| 7,133,717 B2 | 11/2006 | Coston et al. |
| 7,137,957 B2 | 11/2006 | Erickson et al. |
| 7,150,755 B2 | 12/2006 | Levaughn et al. |

(56) References Cited

U.S. PATENT DOCUMENTS

| | | |
|---|---|---|
| 7,172,071 B2 | 2/2007 | Hawkins |
| 7,174,199 B2 | 2/2007 | Berner et al. |
| 7,182,910 B2 | 2/2007 | Allen et al. |
| 7,185,764 B2 | 3/2007 | Lee et al. |
| 7,235,056 B2 | 6/2007 | Duchon et al. |
| 7,247,144 B2 | 7/2007 | Douglas et al. |
| 7,264,627 B2 | 9/2007 | Perez |
| 7,316,671 B2 | 1/2008 | Lastovich et al. |
| 7,335,166 B2 | 2/2008 | Faupel et al. |
| 7,344,499 B1 | 3/2008 | Prausnitz et al. |
| 7,344,587 B2 | 3/2008 | Khan et al. |
| 7,374,545 B2 | 5/2008 | Alroy |
| 7,374,949 B2 | 5/2008 | Kuriger |
| 7,402,441 B2 | 7/2008 | Lowe et al. |
| 7,413,868 B2 | 8/2008 | Kauvar et al. |
| 7,422,567 B2 | 9/2008 | Lastovich et al. |
| 7,429,258 B2 | 9/2008 | Angel et al. |
| 7,537,590 B2 | 5/2009 | Santini et al. |
| 7,544,185 B2 | 6/2009 | Bengtsson |
| 7,556,615 B2 | 7/2009 | Pettis et al. |
| 7,572,237 B2 | 8/2009 | Saikley et al. |
| 7,575,717 B2 | 8/2009 | Cooke et al. |
| 7,585,278 B2 | 9/2009 | Aceti et al. |
| 7,585,412 B2 | 9/2009 | Gorsuch et al. |
| 7,631,760 B2 | 12/2009 | Guelzow et al. |
| 7,758,518 B2 | 7/2010 | Perez et al. |
| 7,767,017 B2 | 8/2010 | Lahann et al. |
| 7,811,236 B2 | 10/2010 | List et al. |
| 7,811,302 B2 | 10/2010 | Steg |
| 7,833,172 B2 | 11/2010 | Hein et al. |
| 7,883,473 B2 | 2/2011 | LeVaughn et al. |
| 7,896,830 B2 | 3/2011 | Gura et al. |
| 7,942,827 B2 | 5/2011 | Mir et al. |
| 7,947,772 B2 | 5/2011 | Lahann |
| 8,043,480 B2 | 10/2011 | Lahann et al. |
| 8,052,849 B2 | 11/2011 | Lahann et al. |
| 8,058,077 B2 | 11/2011 | Groll et al. |
| 8,071,384 B2 | 12/2011 | Burke et al. |
| 8,075,826 B2 | 12/2011 | Lastovich et al. |
| 8,133,191 B2 | 3/2012 | Rosenberg et al. |
| 8,187,708 B2 | 5/2012 | Lahann et al. |
| 8,202,240 B2 | 6/2012 | Felt et al. |
| 8,241,651 B2 | 8/2012 | Lahann |
| 8,246,582 B2 | 8/2012 | Angel et al. |
| 8,344,028 B2 | 1/2013 | Xu et al. |
| 8,383,044 B2 | 2/2013 | Davis et al. |
| 8,465,425 B2 | 6/2013 | Heller et al. |
| 8,523,894 B2 | 9/2013 | Schmelzeisen-Redeker et al. |
| 8,561,795 B2 | 10/2013 | Schott |
| 8,808,202 B2 | 8/2014 | Brancazio |
| 8,821,412 B2 | 9/2014 | Gonzalez-Zugasti et al. |
| 8,821,446 B2 | 9/2014 | Trautman et al. |
| 8,827,971 B2 | 9/2014 | Chickering, III et al. |
| 8,870,903 B2 | 10/2014 | LeVaughn et al. |
| 8,882,794 B2 | 11/2014 | Lum |
| 8,900,180 B2 | 12/2014 | Wolter et al. |
| 8,934,955 B2 | 1/2015 | Schraga |
| 8,971,980 B2 | 3/2015 | Mace et al. |
| 9,028,426 B2 | 5/2015 | List et al. |
| 9,033,898 B2 | 5/2015 | Chickering, III et al. |
| 9,033,989 B2 | 5/2015 | Wolfson et al. |
| 9,039,638 B2 | 5/2015 | Arnitz |
| 9,041,541 B2 | 5/2015 | Levinson et al. |
| 9,101,302 B2 | 8/2015 | Mace et al. |
| 9,113,836 B2 | 8/2015 | Bernstein et al. |
| 9,119,578 B2 | 9/2015 | Haghgooie et al. |
| 9,295,417 B2 | 3/2016 | Haghgooie et al. |
| 9,730,624 B2 | 8/2017 | Gonzalez-Zugasti et al. |
| 9,775,551 B2 | 10/2017 | Bernstein et al. |
| 10,188,335 B2 | 1/2019 | Haghgooie et al. |
| 10,543,310 B2 | 1/2020 | Bernstein et al. |
| 2001/0005772 A1 | 6/2001 | Kisakibaru |
| 2002/0010414 A1 | 1/2002 | Coston et al. |
| 2002/0013538 A1 | 1/2002 | Teller |
| 2002/0065453 A1 | 5/2002 | Lesho et al. |
| 2002/0076443 A1 | 6/2002 | Stein et al. |
| 2002/0077584 A1* | 6/2002 | Lin ................ A61B 5/150984 604/21 |
| 2002/0082543 A1 | 6/2002 | Park et al. |
| 2002/0099308 A1 | 7/2002 | Bojan et al. |
| 2002/0099356 A1 | 7/2002 | Unger et al. |
| 2002/0112981 A1 | 8/2002 | Cooper et al. |
| 2002/0115967 A1* | 8/2002 | Svedman ........... A61B 5/14521 604/313 |
| 2002/0119136 A1 | 8/2002 | Johansen |
| 2002/0130042 A1 | 9/2002 | Moerman et al. |
| 2002/0130093 A1 | 9/2002 | Ferrara et al. |
| 2002/0138049 A1 | 9/2002 | Allen |
| 2002/0143320 A1 | 10/2002 | Levin |
| 2002/0168290 A1 | 11/2002 | Yuzhakov et al. |
| 2002/0169393 A1 | 11/2002 | Cunningham et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0187556 A1 | 12/2002 | Shartle et al. |
| 2002/0188221 A1 | 12/2002 | Sohrab |
| 2003/0004437 A1 | 1/2003 | Collins et al. |
| 2003/0040682 A1 | 2/2003 | Tapper |
| 2003/0055326 A1 | 3/2003 | Sohrab |
| 2003/0083618 A1 | 5/2003 | Angel et al. |
| 2003/0083645 A1 | 5/2003 | Angel et al. |
| 2003/0083685 A1 | 5/2003 | Freeman et al. |
| 2003/0100846 A1 | 5/2003 | Custer et al. |
| 2003/0109807 A1 | 6/2003 | Knoll |
| 2003/0113540 A1 | 6/2003 | Anderson et al. |
| 2003/0135158 A1 | 7/2003 | Gonnelli |
| 2003/0135167 A1 | 7/2003 | Gonnelli |
| 2003/0135201 A1 | 7/2003 | Gonnelli |
| 2003/0135333 A1 | 7/2003 | Aceti et al. |
| 2003/0143746 A1 | 7/2003 | Sage |
| 2003/0159615 A1 | 8/2003 | Anderson et al. |
| 2003/0162304 A1 | 8/2003 | Dority et al. |
| 2003/0181863 A1 | 9/2003 | Ackley et al. |
| 2003/0187394 A1 | 10/2003 | Wilkinson et al. |
| 2003/0187395 A1 | 10/2003 | Gabel et al. |
| 2003/0195398 A1 | 10/2003 | Suzuki et al. |
| 2003/0204148 A1 | 10/2003 | Lange et al. |
| 2003/0208138 A1 | 11/2003 | Olson |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0212423 A1 | 11/2003 | Pugh et al. |
| 2003/0228367 A1 | 12/2003 | Mathiowitz et al. |
| 2004/0010207 A1 | 1/2004 | Flaherty et al. |
| 2004/0053894 A1 | 3/2004 | Mazess et al. |
| 2004/0058458 A1 | 3/2004 | Anker et al. |
| 2004/0096959 A1 | 5/2004 | Stiene et al. |
| 2004/0098009 A1 | 5/2004 | Boecker et al. |
| 2004/0102717 A1 | 5/2004 | Qi |
| 2004/0106904 A1 | 6/2004 | Gonnelli et al. |
| 2004/0133126 A1 | 7/2004 | McNenny |
| 2004/0137640 A1 | 7/2004 | Hirao et al. |
| 2004/0138688 A1 | 7/2004 | Giraud |
| 2004/0162521 A1 | 8/2004 | Bengtsson |
| 2004/0163987 A1 | 8/2004 | Allen |
| 2004/0171980 A1 | 9/2004 | Mitragotri et al. |
| 2004/0199103 A1 | 10/2004 | Kwon |
| 2004/0204744 A1 | 10/2004 | Penner et al. |
| 2004/0236250 A1 | 11/2004 | Hodges et al. |
| 2004/0247016 A1 | 12/2004 | Faries et al. |
| 2004/0249310 A1 | 12/2004 | Shartle et al. |
| 2004/0253185 A1 | 12/2004 | Herweck et al. |
| 2005/0015055 A1 | 1/2005 | Yang |
| 2005/0019902 A1 | 1/2005 | Mathies et al. |
| 2005/0027176 A1 | 2/2005 | Xie |
| 2005/0027308 A1 | 2/2005 | Davis et al. |
| 2005/0033197 A1 | 2/2005 | Cottler |
| 2005/0038669 A1 | 2/2005 | Sachdeva et al. |
| 2005/0054907 A1 | 3/2005 | Page et al. |
| 2005/0064529 A1 | 3/2005 | Kwon |
| 2005/0069925 A1 | 3/2005 | Ford et al. |
| 2005/0070819 A1 | 3/2005 | Poux et al. |
| 2005/0085838 A1 | 4/2005 | Thompson et al. |
| 2005/0090766 A1 | 4/2005 | Montanari |

(56) References Cited

U.S. PATENT DOCUMENTS

| | | |
|---|---|---|
| 2005/0106066 A1 | 5/2005 | Saltsman et al. |
| 2005/0106713 A1 | 5/2005 | Phan et al. |
| 2005/0137481 A1 | 6/2005 | Sheard et al. |
| 2005/0137531 A1 | 6/2005 | Prausnitz et al. |
| 2005/0137536 A1 | 6/2005 | Gonnelli |
| 2005/0172852 A1 | 8/2005 | Anderson et al. |
| 2005/0182307 A1 | 8/2005 | Currie et al. |
| 2005/0196747 A1 | 9/2005 | Stiene |
| 2005/0201974 A1 | 9/2005 | Schestopol et al. |
| 2005/0203360 A1 | 9/2005 | Brauker et al. |
| 2005/0215923 A1 | 9/2005 | Wiegel |
| 2005/0221276 A1 | 10/2005 | Rozakis et al. |
| 2005/0227269 A1 | 10/2005 | Lloyd, Jr. et al. |
| 2005/0228313 A1 | 10/2005 | Kaler et al. |
| 2005/0245844 A1 | 11/2005 | Mace et al. |
| 2005/0249672 A1 | 11/2005 | Bolbot |
| 2005/0251152 A1 | 11/2005 | Herweck et al. |
| 2005/0261632 A1 | 11/2005 | Xu |
| 2005/0261639 A1 | 11/2005 | Herweck |
| 2005/0267422 A1 | 12/2005 | Kriesel |
| 2006/0001551 A1 | 1/2006 | Kraft et al. |
| 2006/0004271 A1 | 1/2006 | Peyser et al. |
| 2006/0004303 A1 | 1/2006 | Weidenhaupt et al. |
| 2006/0030790 A1 | 2/2006 | Braig et al. |
| 2006/0036187 A1 | 2/2006 | Vos et al. |
| 2006/0058602 A1 | 3/2006 | Kwiatkowski et al. |
| 2006/0089566 A1 | 4/2006 | DeHart |
| 2006/0100654 A1 | 5/2006 | Fukuda et al. |
| 2006/0142651 A1 | 6/2006 | Brister et al. |
| 2006/0157362 A1 | 7/2006 | Schraga |
| 2006/0182738 A1 | 8/2006 | Holmes et al. |
| 2006/0189895 A1 | 8/2006 | Neel et al. |
| 2006/0200046 A1 | 9/2006 | Windus-Smith et al. |
| 2006/0202385 A1 | 9/2006 | Xu et al. |
| 2006/0228259 A1 | 10/2006 | Samsoondar |
| 2006/0257883 A1 | 11/2006 | Bjorkaker et al. |
| 2006/0258959 A1 | 11/2006 | Sode |
| 2006/0264779 A1 | 11/2006 | Kemp et al. |
| 2006/0264782 A1 | 11/2006 | Holmes et al. |
| 2007/0004989 A1 | 1/2007 | Dhillon |
| 2007/0016446 A1 | 1/2007 | Brown |
| 2007/0027427 A1 | 2/2007 | Trautman et al. |
| 2007/0031283 A1 | 2/2007 | Davis et al. |
| 2007/0031293 A1 | 2/2007 | Beatty |
| 2007/0036686 A1 | 2/2007 | Hatamian et al. |
| 2007/0046476 A1 | 3/2007 | Hinkamp |
| 2007/0054119 A1 | 3/2007 | Garstecki et al. |
| 2007/0066934 A1 | 3/2007 | Etheredge et al. |
| 2007/0078414 A1 | 4/2007 | McAllister et al. |
| 2007/0083131 A1 | 4/2007 | Escutia et al. |
| 2007/0092637 A1 | 4/2007 | Brown et al. |
| 2007/0100219 A1 | 5/2007 | Sweitzer et al. |
| 2007/0105176 A1 | 5/2007 | Ibey et al. |
| 2007/0112180 A1 | 5/2007 | Gray et al. |
| 2007/0123801 A1 | 5/2007 | Goldberger et al. |
| 2007/0129618 A1 | 6/2007 | Goldberger et al. |
| 2007/0161926 A1* | 7/2007 | Imamura ............ A61B 5/150022 600/573 |
| 2007/0161964 A1 | 7/2007 | Yukhazov |
| 2007/0167340 A1 | 7/2007 | Barthel et al. |
| 2007/0169411 A1 | 7/2007 | Thiessen et al. |
| 2007/0173740 A1 | 7/2007 | Chan et al. |
| 2007/0179404 A1 | 8/2007 | Escutia et al. |
| 2007/0185432 A1 | 8/2007 | Etheredge et al. |
| 2007/0185515 A1 | 8/2007 | Stout |
| 2007/0208275 A1 | 9/2007 | Vinogradov et al. |
| 2007/0213638 A1 | 9/2007 | Herbrechtsmeier et al. |
| 2007/0225676 A1 | 9/2007 | Prausnitz et al. |
| 2007/0231355 A1 | 10/2007 | Quadir et al. |
| 2007/0232956 A1 | 10/2007 | Harman et al. |
| 2007/0233199 A1 | 10/2007 | Moore et al. |
| 2007/0237800 A1 | 10/2007 | Lahann |
| 2007/0238943 A1 | 10/2007 | Poulsen et al. |
| 2007/0249962 A1 | 10/2007 | Alden et al. |
| 2007/0275193 A1 | 11/2007 | deSimone et al. |
| 2008/0009763 A1 | 1/2008 | Chiou et al. |
| 2008/0014627 A1 | 1/2008 | Merchant et al. |
| 2008/0021491 A1 | 1/2008 | Freeman et al. |
| 2008/0033319 A1 | 2/2008 | Kloepfer et al. |
| 2008/0051689 A1 | 2/2008 | Gura et al. |
| 2008/0077096 A1 | 3/2008 | Nakamura et al. |
| 2008/0077430 A1 | 3/2008 | Singer et al. |
| 2008/0081695 A1 | 4/2008 | Patchen |
| 2008/0086051 A1 | 4/2008 | Voegele |
| 2008/0099478 A1 | 5/2008 | Gleich |
| 2008/0103434 A1 | 5/2008 | Lastovich et al. |
| 2008/0108959 A1 | 5/2008 | Jung et al. |
| 2008/0112886 A1 | 5/2008 | Mitragotri et al. |
| 2008/0125673 A1 | 5/2008 | Carano et al. |
| 2008/0125743 A1 | 5/2008 | Yuzhakov |
| 2008/0129486 A1 | 6/2008 | Jeckelmann et al. |
| 2008/0140049 A1 | 6/2008 | Kirby |
| 2008/0154107 A1 | 6/2008 | Jina |
| 2008/0167535 A1 | 7/2008 | Stivoric et al. |
| 2008/0167613 A1 | 7/2008 | Khouri et al. |
| 2008/0183140 A1 | 7/2008 | Paproski et al. |
| 2008/0183144 A1 | 7/2008 | Trautman et al. |
| 2008/0200791 A1 | 8/2008 | Simpson et al. |
| 2008/0200838 A1 | 8/2008 | Goldberger et al. |
| 2008/0220411 A1 | 9/2008 | McNaughton et al. |
| 2008/0221407 A1 | 9/2008 | Baker |
| 2008/0269666 A1 | 10/2008 | Wang et al. |
| 2008/0275327 A1 | 11/2008 | Faarbaek et al. |
| 2008/0275378 A1 | 11/2008 | Herndon |
| 2008/0281290 A1 | 11/2008 | Yodfat et al. |
| 2008/0300508 A1 | 12/2008 | Tomer |
| 2008/0319347 A1 | 12/2008 | Keren |
| 2009/0036795 A1 | 2/2009 | Duineveld et al. |
| 2009/0043250 A1 | 2/2009 | Gonnelli |
| 2009/0048536 A1 | 2/2009 | Freeman et al. |
| 2009/0054813 A1 | 2/2009 | Freeman et al. |
| 2009/0054971 A1 | 2/2009 | Mitsunaga et al. |
| 2009/0076453 A1 | 3/2009 | Mejlhede et al. |
| 2009/0099427 A1 | 4/2009 | Jina et al. |
| 2009/0099478 A1 | 4/2009 | Cassells et al. |
| 2009/0099529 A1 | 4/2009 | Anderson et al. |
| 2009/0105614 A1* | 4/2009 | Momose ............ A61B 10/0045 600/583 |
| 2009/0118662 A1 | 5/2009 | Schnall |
| 2009/0124994 A1 | 5/2009 | Roe |
| 2009/0131829 A1 | 5/2009 | Freeman et al. |
| 2009/0182306 A1 | 7/2009 | Lee et al. |
| 2009/0187160 A1 | 7/2009 | McAllister et al. |
| 2009/0187167 A1 | 7/2009 | Sexton et al. |
| 2009/0198189 A1 | 8/2009 | Simons et al. |
| 2009/0198215 A1 | 8/2009 | Chong et al. |
| 2009/0209883 A1 | 8/2009 | Higgins et al. |
| 2009/0215159 A1 | 8/2009 | Kirby |
| 2009/0216103 A1 | 8/2009 | Brister et al. |
| 2009/0216629 A1 | 8/2009 | James et al. |
| 2009/0264720 A1 | 10/2009 | Torjman et al. |
| 2009/0270792 A1 | 10/2009 | Lastovich et al. |
| 2009/0318779 A1 | 12/2009 | Tran |
| 2009/0318846 A1 | 12/2009 | Prausnitz et al. |
| 2010/0010374 A1 | 1/2010 | Escutia et al. |
| 2010/0021947 A1 | 1/2010 | Emery et al. |
| 2010/0030111 A1 | 2/2010 | Perriere |
| 2010/0042137 A1 | 2/2010 | Oronsky et al. |
| 2010/0049126 A1 | 2/2010 | Bronfeld et al. |
| 2010/0069726 A1 | 3/2010 | Levinson |
| 2010/0069730 A1 | 3/2010 | Bergstrom et al. |
| 2010/0094170 A1 | 4/2010 | Wilson et al. |
| 2010/0111970 A1 | 5/2010 | Pons et al. |
| 2010/0114014 A1 | 5/2010 | Roser |
| 2010/0121368 A1 | 5/2010 | Kim et al. |
| 2010/0147763 A1 | 6/2010 | Tsou et al. |
| 2010/0160894 A1 | 6/2010 | Julian et al. |
| 2010/0210970 A1 | 8/2010 | Horikawa et al. |
| 2010/0222703 A1 | 9/2010 | Takashima et al. |
| 2010/0234768 A1 | 9/2010 | Uchiyama et al. |
| 2010/0240079 A1 | 9/2010 | Jackson |
| 2010/0249560 A1* | 9/2010 | Levinson ............ A61B 5/021 600/364 |
| 2010/0256465 A1 | 10/2010 | Bernstein et al. |

(56) References Cited

U.S. PATENT DOCUMENTS

| | | |
|---|---|---|
| 2010/0256524 A1* | 10/2010 | Levinson ......... A61B 5/150412 600/576 |
| 2010/0261988 A1 | 10/2010 | Tamir |
| 2010/0269837 A1 | 10/2010 | Levinson et al. |
| 2010/0272652 A1 | 10/2010 | Levinson et al. |
| 2010/0292191 A1 | 11/2010 | Mainx et al. |
| 2010/0318111 A1 | 12/2010 | Sarna et al. |
| 2010/0324449 A1 | 12/2010 | Rostaing et al. |
| 2010/0324451 A1 | 12/2010 | Ishibashi et al. |
| 2011/0003770 A1 | 1/2011 | Eek |
| 2011/0009847 A1 | 1/2011 | Levinson et al. |
| 2011/0034830 A1 | 2/2011 | Nakamura et al. |
| 2011/0040208 A1 | 2/2011 | Mcminn et al. |
| 2011/0040317 A1 | 2/2011 | Lee et al. |
| 2011/0105828 A1 | 5/2011 | Perless et al. |
| 2011/0105872 A1 | 5/2011 | Chickering et al. |
| 2011/0105951 A1 | 5/2011 | Bernstein et al. |
| 2011/0105952 A1 | 5/2011 | Bernstein et al. |
| 2011/0112384 A1 | 5/2011 | Eisenhardt et al. |
| 2011/0112438 A1 | 5/2011 | Radzuinas et al. |
| 2011/0125058 A1 | 5/2011 | Levinson et al. |
| 2011/0137203 A1 | 6/2011 | Nishiuchi et al. |
| 2011/0172508 A1 | 7/2011 | Chickering, III et al. |
| 2011/0172510 A1 | 7/2011 | Chickering, III et al. |
| 2011/0181410 A1 | 7/2011 | Levinson et al. |
| 2011/0245708 A1 | 10/2011 | Finkel et al. |
| 2011/0251562 A1 | 10/2011 | Chickering, III et al. |
| 2011/0276027 A1 | 11/2011 | Trautman et al. |
| 2011/0282173 A1 | 11/2011 | Fonduca et al. |
| 2011/0288389 A9 | 11/2011 | Levinson et al. |
| 2011/0306853 A1 | 12/2011 | Black et al. |
| 2012/0010529 A1 | 1/2012 | Chickering, III et al. |
| 2012/0016308 A1 | 1/2012 | Schott |
| 2012/0039809 A1 | 2/2012 | Levinson et al. |
| 2012/0041338 A1 | 2/2012 | Chickering et al. |
| 2012/0089050 A1 | 4/2012 | Fukuda |
| 2012/0123297 A1 | 5/2012 | Brancazio |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2012/0315271 A1 | 12/2012 | Shelton et al. |
| 2013/0018279 A1 | 1/2013 | Plante et al. |
| 2013/0079666 A1 | 3/2013 | Gonzalez-Zugasti et al. |
| 2013/0081960 A1 | 4/2013 | Schott |
| 2013/0131741 A1 | 5/2013 | Kourtis et al. |
| 2013/0138058 A9 | 5/2013 | Chickering, III et al. |
| 2013/0158468 A1 | 6/2013 | Bernstein et al. |
| 2013/0158482 A1 | 6/2013 | Davis et al. |
| 2014/0336536 A1 | 11/2014 | Brancazio |
| 2015/0038876 A1 | 2/2015 | Gonzalez-Zugasti et al. |
| 2015/0057510 A1 | 2/2015 | Levinson et al. |
| 2015/0087944 A1 | 3/2015 | Levinson et al. |
| 2015/0313522 A1 | 11/2015 | Bernstein et al. |
| 2015/0320349 A1 | 11/2015 | Haghgooie et al. |
| 2015/0342509 A1 | 12/2015 | Peeters et al. |
| 2016/0038068 A1 | 2/2016 | Chickering et al. |
| 2017/0067803 A1 | 3/2017 | Jackson et al. |
| 2017/0120022 A1 | 5/2017 | Chickering et al. |
| 2017/0120023 A1 | 5/2017 | Davis et al. |
| 2017/0127990 A1 | 5/2017 | Levinson et al. |
| 2017/0127991 A1 | 5/2017 | Bernstein et al. |
| 2017/0172481 A1 | 6/2017 | Berthier et al. |
| 2017/0215790 A1 | 8/2017 | Levinson et al. |
| 2017/0224264 A1 | 8/2017 | Brancazio |
| 2017/0281852 A1 | 10/2017 | Bernstein et al. |
| 2018/0008183 A1 | 1/2018 | Chickering et al. |
| 2018/0132774 A1 | 5/2018 | Gonzalez-Zugasti et al. |
| 2018/0242890 A1 | 8/2018 | Chickering et al. |
| 2018/0310884 A1 | 11/2018 | Chickering et al. |
| 2018/0317829 A9 | 11/2018 | Gonzalez-Zugasti et al. |
| 2019/0023473 A1 | 1/2019 | Schott |
| 2019/0053740 A1 | 2/2019 | Davis et al. |
| 2019/0159709 A1 | 5/2019 | Barone et al. |
| 2019/0209820 A1 | 7/2019 | Chickering et al. |
| 2019/0336058 A1 | 11/2019 | Haghgooie et al. |
| 2020/0015751 A9 | 1/2020 | Chickering et al. |

FOREIGN PATENT DOCUMENTS

| | | |
|---|---|---|
| CN | 2331315 Y | 8/1999 |
| CN | 2462854 Y | 12/2001 |
| CN | 2600055 Y | 1/2004 |
| CN | 1499949 A | 5/2004 |
| CN | 1753646 A | 3/2006 |
| CN | 101248998 A | 8/2008 |
| CN | 101347384 A | 1/2009 |
| CN | 101678196 A | 3/2010 |
| DE | 198 33 868 A1 | 5/2000 |
| DE | 20 2008 010918 U1 | 12/2008 |
| EP | 0 043 738 A2 | 1/1982 |
| EP | 0 115 388 A1 | 8/1984 |
| EP | 0 250 693 A1 | 1/1988 |
| EP | 0 365 196 A2 | 4/1990 |
| EP | 0 535 266 A1 | 4/1993 |
| EP | 0 555 554 A1 | 8/1993 |
| EP | 0 803 288 A2 | 10/1997 |
| EP | 0 838 232 A2 | 4/1998 |
| EP | 0 977 032 A1 | 2/2000 |
| EP | 1 027 864 A1 | 8/2000 |
| EP | 1 360 934 A1 | 11/2003 |
| EP | 1 437 093 A1 | 7/2004 |
| EP | 1 470 781 A2 | 10/2004 |
| EP | 1 491 143 A1 | 12/2004 |
| EP | 1 522 260 A1 | 4/2005 |
| EP | 1 611 837 A2 | 1/2006 |
| EP | 1 639 938 A1 | 3/2006 |
| EP | 1 652 551 A2 | 5/2006 |
| EP | 1 834 589 A2 | 9/2007 |
| EP | 1 844 710 B1 | 10/2007 |
| EP | 1 997 431 A1 | 12/2008 |
| EP | 2 064 993 A1 | 6/2009 |
| EP | 2 077 128 A1 | 7/2009 |
| EP | 1 187 653 B1 | 3/2010 |
| EP | 2 701 601 A1 | 3/2014 |
| EP | 12719217.7 | 6/2015 |
| EP | 16163588.2 | 11/2016 |
| EP | 16163588.3 | 2/2017 |
| FR | 2929135 A1 | 10/2009 |
| GB | 2 153 223 A | 8/1985 |
| JP | 61-198061 A2 | 9/1986 |
| JP | 63-108264 A | 5/1988 |
| JP | 03-060645 A2 | 3/1991 |
| JP | 4-053536 A2 | 2/1992 |
| JP | 5-63506 A | 8/1993 |
| JP | 06-508286 T2 | 9/1994 |
| JP | 7-255706 A | 10/1995 |
| JP | H08-080291 A | 3/1996 |
| JP | 2000-116629 A | 4/2000 |
| JP | 2002-085384 | 3/2002 |
| JP | 2002-272710 A | 9/2002 |
| JP | 2002-532165 A1 | 10/2002 |
| JP | 2003-159238 A | 6/2003 |
| JP | 2004-8413 A | 1/2004 |
| JP | 2004-500948 | 1/2004 |
| JP | 2004-191336 A | 7/2004 |
| JP | 2004-532079 A | 10/2004 |
| JP | 2005-011364 A | 1/2005 |
| JP | 2005-517463 A | 6/2005 |
| JP | 2005-522243 | 7/2005 |
| JP | 2005-211189 A | 8/2005 |
| JP | 2005-525141 A | 8/2005 |
| JP | 2005-245705 A | 9/2005 |
| JP | 2006-014789 | 1/2006 |
| JP | 2006-15148 A | 1/2006 |
| JP | 2006-109894 A | 4/2006 |
| JP | 2006-521555 A | 9/2006 |
| JP | 2006-280912 A | 10/2006 |
| JP | 2007-209549 A | 8/2007 |
| JP | 2007-209747 A | 8/2007 |
| JP | 2007-236686 | 9/2007 |
| JP | 2007-526460 A | 9/2007 |
| JP | 2008-022988 A | 2/2008 |

(56) References Cited

FOREIGN PATENT DOCUMENTS

| | | |
|---|---|---|
| JP | 2008-54884 A | 3/2008 |
| JP | 2008-079853 A | 4/2008 |
| JP | 2008-99988 A | 5/2008 |
| JP | 2008-099992 A | 5/2008 |
| JP | 2008-518662 A | 6/2008 |
| JP | 2008-534192 A | 8/2008 |
| JP | 2009-504273 A | 2/2009 |
| JP | 2009-509679 A | 3/2009 |
| JP | 2009-066385 A | 4/2009 |
| JP | 2009-078173 A | 4/2009 |
| JP | 2009-519064 A | 5/2009 |
| JP | 2009-254899 A2 | 8/2009 |
| JP | 2010-520036 A | 6/2010 |
| JP | 2011-511660 A | 4/2011 |
| JP | 2011-522593 A | 8/2011 |
| KR | 2003-0061753 A | 7/2003 |
| WO | WO 92/02175 A1 | 2/1992 |
| WO | WO 92/04867 A1 | 4/1992 |
| WO | WO 93/00043 A1 | 1/1993 |
| WO | WO 95/10223 A2 | 4/1995 |
| WO | WO 95/15783 A1 | 6/1995 |
| WO | WO 97/08987 A1 | 3/1997 |
| WO | WO 97/10745 A1 | 3/1997 |
| WO | WO 97/034587 A2 | 9/1997 |
| WO | WO 97/48442 A1 | 12/1997 |
| WO | WO 98/24366 A2 | 6/1998 |
| WO | WO 99/27852 A1 | 6/1999 |
| WO | WO 99/59657 A1 | 11/1999 |
| WO | WO 00/35357 A1 | 6/2000 |
| WO | WO 00/35530 A1 | 6/2000 |
| WO | WO 00/74763 A2 | 12/2000 |
| WO | WO 01/43643 A1 | 6/2001 |
| WO | WO 01/93946 A1 | 12/2001 |
| WO | WO 02/00101 A2 | 1/2002 |
| WO | WO 02/05890 A2 | 1/2002 |
| WO | WO 02/30301 A1 | 4/2002 |
| WO | WO 02/30506 A2 | 4/2002 |
| WO | WO 02/078533 A2 | 10/2002 |
| WO | WO 02/091922 A1 | 11/2002 |
| WO | WO 02/100253 A2 | 12/2002 |
| WO | WO 02/100460 A2 | 12/2002 |
| WO | WO 02/101359 A2 | 12/2002 |
| WO | WO 03/020134 A2 | 3/2003 |
| WO | WO 03/026611 A2 | 4/2003 |
| WO | WO 03/030984 A2 | 4/2003 |
| WO | WO 03/037407 A1 | 5/2003 |
| WO | WO 2003/037403 A1 | 5/2003 |
| WO | WO 03/070099 A1 | 8/2003 |
| WO | WO 03/082091 A2 | 10/2003 |
| WO | WO 03/088851 A1 | 10/2003 |
| WO | WO 2003/083469 A2 | 10/2003 |
| WO | WO 03/099123 A1 | 12/2003 |
| WO | WO 04/006982 A3 | 1/2004 |
| WO | WO 04/022133 A2 | 3/2004 |
| WO | WO 04/085995 A2 | 10/2004 |
| WO | WO 2005/000118 A1 | 1/2005 |
| WO | WO 2005/023111 A1 | 3/2005 |
| WO | WO 2005/025413 A2 | 3/2005 |
| WO | WO 2005/084534 A1 | 9/2005 |
| WO | WO 2005/095965 A1 | 10/2005 |
| WO | WO 2005/107594 A2 | 11/2005 |
| WO | WO 2005/123173 A1 | 12/2005 |
| WO | WO 2006/003403 A1 | 1/2006 |
| WO | WO 2006/019823 A2 | 2/2006 |
| WO | WO 2006/027586 | 3/2006 |
| WO | WO 2006/050032 A2 | 5/2006 |
| WO | WO 2006/111741 A1 | 10/2006 |
| WO | WO 2006/121510 A2 | 11/2006 |
| WO | WO 2006/128034 A1 | 11/2006 |
| WO | WO 2006/132504 A1 | 12/2006 |
| WO | WO 2007/002521 A2 | 1/2007 |
| WO | WO 2007/002522 A1 | 1/2007 |
| WO | WO 2007/021979 A2 | 2/2007 |
| WO | WO 2007/079530 A1 | 7/2007 |
| WO | WO 2007/091671 A1 | 8/2007 |
| WO | WO 2007/097754 A1 | 8/2007 |
| WO | WO 2007/108519 A1 | 9/2007 |
| WO | WO 2007/108987 A2 | 9/2007 |
| WO | WO 2007/115291 A2 | 10/2007 |
| WO | WO 2007/124411 A1 | 11/2007 |
| WO | WO 2008/016646 A2 | 2/2008 |
| WO | WO 2008/031035 A2 | 3/2008 |
| WO | WO 2008/043156 A1 | 4/2008 |
| WO | WO 2008/052034 A1 | 5/2008 |
| WO | WO 2008/062032 A1 | 5/2008 |
| WO | WO 2008/081444 A2 | 7/2008 |
| WO | WO 2008/109845 A2 | 9/2008 |
| WO | WO 2008/153930 A1 | 12/2008 |
| WO | WO 2009/004627 A3 | 1/2009 |
| WO | WO 2009/008267 A1 | 1/2009 |
| WO | WO 2009/011138 A1 | 1/2009 |
| WO | WO 2009/027950 A2 | 3/2009 |
| WO | WO 2009/055693 A2 | 4/2009 |
| WO | WO 2009/071775 A1 | 6/2009 |
| WO | WO 2009/104765 A1 | 8/2009 |
| WO | WO 2009/107135 A2 | 9/2009 |
| WO | WO 2009/126653 A1 | 10/2009 |
| WO | WO 2009/148624 A1 | 12/2009 |
| WO | WO 2009/149308 A2 | 12/2009 |
| WO | WO 2009/151421 A1 | 12/2009 |
| WO | WO 2010/011641 A2 | 1/2010 |
| WO | WO 2010/101620 A2 | 9/2010 |
| WO | WO 2010/101621 A1 | 9/2010 |
| WO | WO 2010/101625 A2 | 9/2010 |
| WO | WO 2010/101626 A1 | 9/2010 |
| WO | WO 2010/110916 A2 | 9/2010 |
| WO | WO 2010/120294 A1 | 10/2010 |
| WO | WO 2011/016019 A1 | 2/2011 |
| WO | WO 2011/053796 A2 | 5/2011 |
| WO | WO 2011/065972 A2 | 6/2011 |
| WO | WO 2011/088214 A2 | 7/2011 |
| WO | WO 2012/058337 A2 | 5/2012 |
| WO | WO 2012/064802 A1 | 5/2012 |
| WO | PCT/US2012/035207 | 8/2012 |
| WO | PCT/US2012/035207 | 10/2012 |
| WO | WO 2012/149134 A1 | 11/2012 |
| WO | PCT/US2012/035207 | 11/2013 |
| WO | WO 2014/160893 A2 | 10/2014 |

OTHER PUBLICATIONS

Partial European Search Report dated Nov. 3, 2016 for European Application No. 16163588.3.
Extended European Search Report dated Feb. 3, 2017 in connection with European Application No. 16163588.3.
International Preliminary Report on Patentability for PCT/US2012/035207 dated Nov. 7, 2013.
International Search Report and Written Opinion dated Oct. 4, 2012 in connection with PCT/U52012/035207.
Invitation to Pay Additional Fees dated Aug. 17, 2012 in connection with PCT/US2012/035207.
[No Author Listed] Greiner Bio-One Preanalytics Catalogue. www.gbo.com/preanalytics. Feb. 2012. 76 pages.
[No Author Listed] Safe-T-Fill®: 100% Plastic Capillary Blood Collection Systems. RAM Scientific. [Month of publication not listed on copy] 2003. Last accessed Jun. 28, 2012 at http//www.ramsci.com.
[No Author Listed] Sof-Tact Manual. Date Unknown. 57 pages. (After reasonable inquiry, the undersigned believes this manual was available beginning 2001, but cannot determine the exact date of this publication.The year of publication is sufficiently earlier than the effective U.S. filing date and priority date so that the particular month and year of publication is not in issue. See MPEP. 609.04(a).)
Angell et al., Silicon Micromechanical Devices. Scientific American. Apr. 1983;248:44-55.
Aungst et al., Contributions of drug solubilization, partitioning, barrier disruption, and solvent permeation to the enhancement of skin permeation of various compounds with fatty acids and amines. Pharm Res. Jul. 1990;7(7):712-8.
Baroli, Penetration of metallic nanoparticles in human full-thickness skin. J. Ind. Derm. 2007;127:1701-12. Epub Mar. 22, 2007.

(56) References Cited

OTHER PUBLICATIONS

Bina et al., Clinical impact of prandial state, exercise, and site preparation on the equivalence of alternative-site blood glucose testing. Diabetes Care. Apr. 2003;26(4):981-5.
Brown, Encapsulation of glucose oxidase and an oxygen-quenched fluorophore in polyelectrolyte-coated calcium alginate microspheres as optical glucose sensor systems. Biosens Bioelec. 2005;21:212-16. Epub Sep. 17, 2004.
Cormier et al., Transdermal delivery of desmopressin using a coated microneedle array patch system. J Control Release. Jul. 7, 2004;97(3):503-11.
Duffy et al., Rapid Prototyping of Microfluidic Systems and Polydimethylsiloxane. Anal Chem. Dec. 1, 1998;70:4974-84.
Elias, The Microscopic Structure of the Epidermis and Its Derivatives. In: Percutaneous Absorption—Mechanisms—Methodology. Bronaugh et al., eds. Marcell Dekker. 1989;3-12. (The year of publication is sufficiently earlier than the effective U.S. filing date and any foreign priority date so that the particular month of publication is not in issue. See MPEP 609.04(a)).
Fineberg et al., Use of an automated device for alternative site blood glucose monitoring. Diabetes Care. Jul. 2001;24(7):1217-20.
Gomes et al., Evaluation of nanoparticles loaded with benzopsoralen in rat peritoneal exudate cells. Int J Pharm. Mar. 6, 2007;332(1-2):153-60. Epub Sep. 27, 2006.
Kost et al., Chapter 4. Ultrasound-Mediated Transdermal Drug Delivery. In: Topical Drug Bioavailability Bioequivalance, and Penetration. Shah et al., eds. Plennum, NY. 1993:91-104. (The year of publication is sufficiently earlier than the effective U.S. filing date and any foreign priority date so that the particular month of publication is not in issue. See MPEP 609.04(a)).
Matriano et al., Macroflux microprojection array patch technology: a new and efficient approach for intracutaneous immunization Pharm Res. Jan. 2002;19(1):63-70.
McShane, Microcapsules as 'smart tattoo' glucose sensors: engineering systems with enzymes and glucose binding sensing elements, *Top Fluor. Spec.*, 2006, vol. 11, *Glc. Sens.*, p. 131-163. (The year of publication is sufficiently earlier than the effective U.S. filing date and any foreign priority date so that the particular month of publication is not in issue. See MPEP 609.04(a)).
Mitragotri et al., Sonophoresis: Enhanced Transfermal Drug Delivery by Application of Ultrasound. In: Encl. of Pharm. Tech., vol. 14, Swarbick, J., Boylan, J., (Eds.), vol. 14, 103-122, 1996. (After reasonable inquiry, the undersigned believes this was available in 1996, but cannot determine the exact date of this publication. The year of publication is sufficiently earlier than the effective U.S. filing date and priority date so that the particular month and year of publication is not in issue. See MPEP 609.04(a).).
Rousche et al., A method for pneumatically inserting an array of penetrating electrodes into cortical tissue. Annals of Biomedical Engineering Jul. 1992;20(4):413-22.
Rousche et al., A System for Impact Insertion of a 100 Electrode Array into Cortical Tissue. Annual Intl Conf IEEE Engineer Med Biol Soc. 1990;12(2):O494-95. (The year of publication is sufficiently earlier than the effective U.S. filing date and any foreign priority date so that the particular month of publication is not in issue. See MPEP 609.04(a)).
Rouse, Effects of mechanical flexion on the penetration of fullerene amino acid-derivatized peptide nanoparticles through skin. Nano Lett. Jan. 2007;7(1):155-60. Epub Dec. 6, 2006.
Suk et al., Gene delivery to differentiated neurotypic cells with RGD and HIV Tat peptide functionalized polymeric nanoparticles. Biomaterials. Oct. 2006;27(29):5143-50.
Uhrich et al., Polymeric systems for controlled drug release. Chem. Rev. 1999;99:3181-98. Epub Oct. 26, 1999.
Verbaan et al., Improved piercing of microneedle arrays in dermatomed human skin by an impact insertion method. J Control Release. May 22, 2008;128(1):80-8. Epub Feb. 26, 2008.
Whiiesides et al., Soft lithography in biology and biochemistry. Annu Rev Biomed Eng. Aug. 2001;3:335-73.
Xia et al., Soft Lithography. Ann Rev Mater Sci. Aug. 1998;28:153-84.
U.S. Appl. No. 16/806,426, filed Mar. 2, 2020, Chickering et al.
U.S. Appl. No. 16/705,286, filed Dec. 6, 2019, Bernstein et al.
[No Author Listed] Air-Tite Products Co., Inc.—Luer Slip. Oct. 14, 2008. Retrieved from the Internet: https://web.archive.org/web/20081014224752/https://www.air-tite-shop.com/c-6-luer-slip.aspx on Aug. 28, 2019. 2 pages.
[No Author Listed] Air-Tite Products Co., Inc.—Luer Lock. Oct. 14, 2008. Retrieved from the Internet: https://web.archive.org/web/20081023203858/https://www.air-tite-shop.com/c-7-luer-lock.aspx on Aug. 28, 2019. 2 pages.
Matsuura et al., Development of a blood extraction device for a miniature SMBG system. Dec. 27, 2007. Proceedings vol. 6799, BioMEMS and Nanotechnology III; 67990N (2007) https://doi.org/10.1117/12.758869. Event: SPIE Microelectronics, MEMS, and Nanotechnology, 2007, Canberra, ACT, Australia.
U.S. Appl. No. 14/797,421, filed Jul. 13, 2015, Bernstein et al.
U.S. Appl. No. 15/281,626, filed Sep. 30, 2016, Chickering et al.
U.S. Appl. No. 12/915,789, filed Oct. 29, 2010, Bernstein et al.
U.S. Appl. No. 12/915,820, filed Oct. 29, 2010, Bernstein et al.
U.S. Appl. No. 14/682,478, filed Apr. 9, 2015, Levinson et al.
U.S. Appl. No. 14/513,327, filed Oct. 14, 2014, Levinson et al.
U.S. Appl. No. 13/006,117, filed Jan. 13, 2011, Chickering et al.
U.S. Appl. No. 15/387,459, filed Dec. 21, 2016, Levinson et al.
U.S. Appl. No. 15/285,034, filed Oct. 4, 2016, Levinson et al.
U.S. Appl. No. 13/183,789, filed Jul. 15, 2011, Schott.
U.S. Appl. No. 15/231,881, filed Aug. 9, 2016, Chickering et al.
U.S. Appl. No. 15/290,217, filed Oct. 11, 2016, Levinson et al.
U.S. Appl. No. 15/297,253, filed Oct. 19, 2016, Brancazio.
U.S. Appl. No. 13/006,165, filed Jan. 13, 2011, Chickering et al.
U.S. Appl. No. 14/328,892, filed Jul. 11, 2014, Gonzalez-Zugasti et al.
U.S. Appl. No. 14/805,678, filed Jul. 22, 2015, Haghgooie et al.
U.S. Appl. No. 15/299,591, filed Oct. 21, 2016, Bernstein et al.
U.S. Appl. No. 15/349,090, filed Nov. 11, 2016, Bernstein et al.
U.S. Appl. No. 15/156,386, filed May 17, 2016, Bernstein et al.
U.S. Appl. No. 15/916,330, filed Mar. 9, 2018, Davis et al.
U.S. Appl. No. 15/828,908, filed Dec. 1, 2017, Chickering et al.
U.S. Appl. No. 15/899,613, filed Feb. 20, 2018, Schott.
U.S. Appl. No. 16/048,722, filed Jul. 30, 2018, Chickering et al.
U.S. Appl. No. 15/693,666, filed Sep. 1, 2017, Chickering et al.
U.S. Appl. No. 15/634,354, filed Jun. 27, 2017, Gonzalez-Zugasti et al.
U.S. Appl. No. 16/218,441, filed Dec. 12, 2018, Haghgooie et al.
U.S. Appl. No. 16/321,123, filed Jan. 28, 2019, Barone et al.

\* cited by examiner

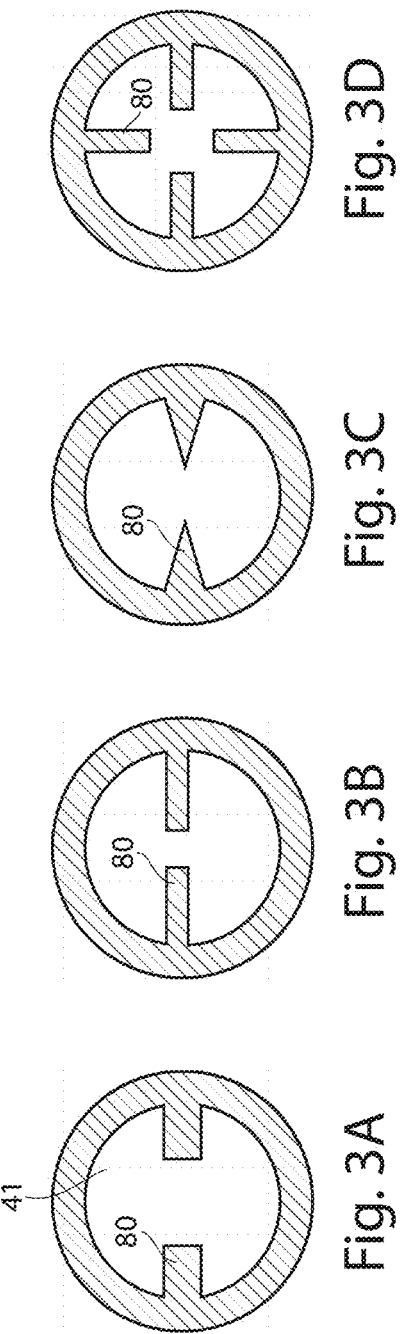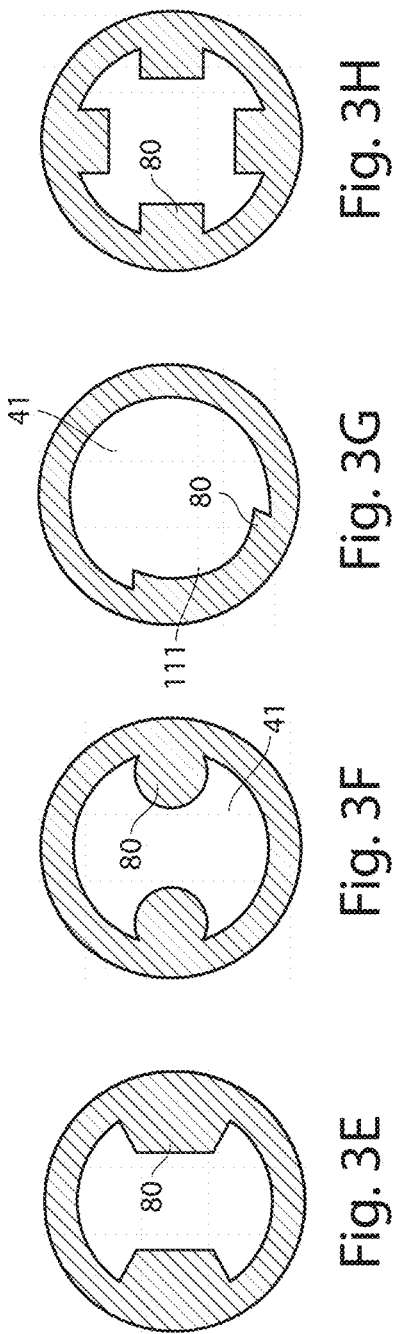

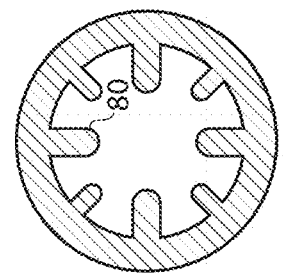
Fig. 3M
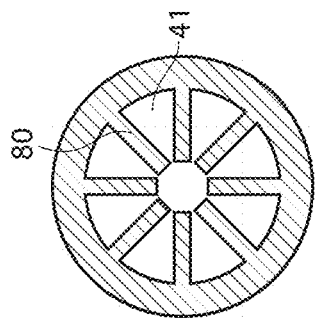
Fig. 3J
Fig. 3L
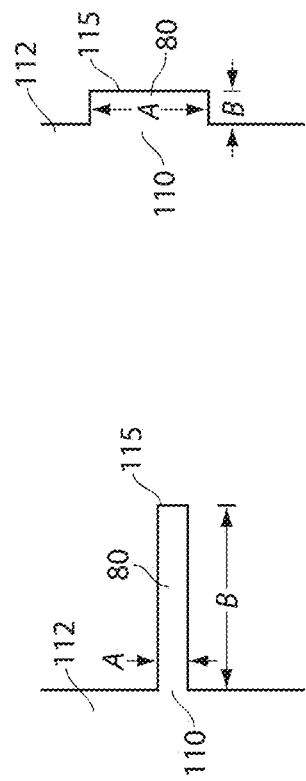
Fig. 3I
Fig. 3K

SYSTEMS AND METHODS FOR COLLECTING FLUID FROM A SUBJECT

CROSS-REFERENCE TO RELATED APPLICATIONS

This application is a continuation of U.S. patent application Ser. No. 13/456,394, filed Apr. 26, 2012, entitled "SYSTEMS AND METHODS FOR COLLECTING FLUID FROM A SUBJECT," which claims the benefit under 35 U.S.C. § 119 (e) of U.S. Provisional Application Ser. No. 61/480,960, entitled "SYSTEMS AND METHODS FOR COLLECTING FLUID FROM A SUBJECT" filed on Apr. 29, 2011.

FIELD OF INVENTION

The present invention generally relates to systems and methods for delivering to and/or receiving fluids or other materials, such as blood or interstitial fluid, from subjects, e.g., to or from the skin and/or beneath the skin.

BACKGROUND

Phlebotomy or venipuncture is the process of obtaining intravenous access for the purpose of intravenous therapy or obtaining a sample of venous blood. This process is typically practiced by medical practitioners, including paramedics, phlebotomists, doctors, nurses, and the like. Substantial equipment is needed to obtain blood from a subject, including the use of evacuated (vacuum) tubes, e.g., such as the Vacutainer™ (Becton, Dickinson and company) and Vacuette™ (Greiner Bio-One GmBH) systems. Other equipment includes hypodermic needles, syringes, and the like. However, such procedures are complicated and require sophisticated training of practitioners, and often cannot be done in non-medical settings. Accordingly, improvements in methods of obtaining blood or other fluids or through from the skin are still needed.

SUMMARY OF INVENTION

The present invention generally relates to systems and methods for delivering to and/or receiving fluids or other materials, such as blood or interstitial fluid, from subjects, e.g., from the skin of a subject, including at the surface and/or beneath the surface of the skin. The subject matter of the present invention involves, in some cases, interrelated products, alternative solutions to a particular problem, and/or a plurality of different uses of one or more systems and/or articles.

In one aspect, the present invention is directed to a device for receiving bodily fluid from a subject. In some aspects, the device includes a flow activator that may cause fluid to be released from the skin of the subject and enter a portion of a fluid transporter of the device. Additionally, the fluid transporter may include a beading disruptor for disrupting a pooling of bodily fluids on the surface of the skin. In another aspect, the fluid transporter may include a recess or other applicator region and a capillary extending along a surface defining the applicator region. In yet another aspect, at least a portion of a surface defining the recess or applicator region may be pleated.

In one aspect, the fluid transporter fluidly communicates with an inlet of a microfluidic channel. In some embodiments, the inlet may be positioned such that at least a portion of the inlet is positioned within about 0.7 millimeters of an opening to a recess or the applicator region. In other embodiments, at least a portion of the inlet is positioned within about 10% of the opening relative to the distance between the opening and a point within the recess or applicator region perpendicularly furthest away from the opening.

In one aspect, the device includes a seal arranged to control a fluid communication pathway between a recess or applicator region and a vacuum source. In another aspect, the device may include a first volume defined by the applicator region and the opening, and a second volume defined by the vacuum source. The volumetric ratio of the first volume to the second volume may be at least about 1:6.

In one aspect, the present invention is related to methods for receiving bodily fluid from a subject. In some aspects, the method includes applying, to the skin of a subject, a device including an applicator region configured to receive a fluid and a vacuum source having a pressure less than ambient pressure, moving air from the applicator region into the vacuum source to equate the pressure between the applicator region and the vacuum source, receiving bodily fluid from the skin into the applicator region, at least a portion of the fluid at least partially blocking an inlet of a fluid communication pathway between the applicator region and the vacuum source such that the pressure within the applicator region becomes greater than the pressure within the vacuum source, and moving the bodily fluid towards the vacuum source due to a pressure difference between the applicator region and the vacuum source. In some aspects, pressure is increased within the applicator region once bodily fluid enters the inlet, thereby moving the bodily fluid towards the vacuum source due to a difference in pressure between the applicator region and vacuum source.

In another illustrative embodiment, a device for receiving bodily fluid from a subject includes a fluid transporter arranged to receive bodily fluid on skin of a subject at an opening, a channel having an inlet in fluid communication with the fluid transporter, and a beading disruptor located with respect to the fluid transporter to interact with fluid entering the opening of the fluid transporter and influence flow of the fluid to the inlet. The beading disruptor may perform one or more functions, such as guiding, wicking or otherwise aiding flow of liquid to the inlet, resisting excessive entry of skin into the device, compensating for relatively small volume fluid release or other presence at the opening, and so on. For example, the fluid transporter may include a recess in fluid communication with the opening, e.g., through which blood or other fluid passes to the recess. The opening may have a center and the beading disruptor may be positioned with respect to the fluid transporter such that a droplet of fluid at the center of the opening and lying on a surface at a contact angle of 45° with the surface first contacts the beading disruptor prior to contacting a portion of the fluid transporter. The beading disruptor may include one or more protrusions, such as a protrusion having first and second ends, a width and a length extending from the first end to the second end. The protrusion may be relatively long and thin, where a ratio of the width of the protrusion at the first end to the length is greater than about 1, or may be relatively short and wide, where a ratio of the width of the protrusion at the first end to the length is less than about 1. In one embodiment, the fluid transporter includes a recess defined by a wall and in fluid communication with the opening, and the beading disruptor includes at least one protrusion that extends from the wall into the recess. The at least one protrusion may extend across the recess from a first side of the recess to a second side of the recess, or may be cantilevered from the wall. The at least one protrusion may be arranged to lie in a plane, such as a plane that is positioned in the recess and away from the opening. In other arrangements, the at least one protrusion may extend at a downward angle to the wall and toward the opening, and/or may not be arranged to lie in a plane, but rather may arranged in other ways. In one embodiment, a portion of the at least one protrusion may be arranged to move away from the opening when contacted by a skin surface entering the opening. This arrangement may help the protrusion resist movement of a skin surface into the recess and/or aid in causing flow of blood or other fluid to the inlet. In one embodiment, the fluid transporter may include a capillary structure adjacent the beading disruptor that is arranged to conduct fluid to the inlet. For example, the beading disruptor may cause fluid to be introduced to the capillary structure, which conducts a flow of fluid to the inlet.

The fluid transporter may include a flow activator, such as a device having one or more needles, to cause the release of fluid from a surface, such as skin. At least some of the needles may have a length of at least about 500 micrometers, and/or to have a maximum penetration into skin of a subject of no more than about 1 mm. If the flow activator includes needles, any suitable number of needles may be included, and may be arranged in any configuration, such as an array of microneedles having at least 6 microneedles. A fluid transporter recess may have a volume of any suitable size, such as no more than about 2 ml, 5 ml, etc. The inlet may be positioned in any suitable way with respect to the opening, such as within about 0.7 mm of the opening of the fluid transporter or such that at least a portion of the inlet is positioned within a distance of the opening that is about 10% of a largest dimension of the recess.

The device may also include a vacuum source and a seal arranged to control a fluid communication pathway between the vacuum source and the inlet. The vacuum source may include a vacuum chamber having a pressure less than ambient pressure prior to opening of the seal, which may help draw fluid from the fluid transporter and into the inlet, may help draw skin into the device for interaction with a flow activator, etc.

The device may be sized and/or shaped in any suitable way, and may have a relatively small size that is convenient for handling and use. For example, the device may have a largest lateral dimension (a dimension that is generally parallel to a skin surface or other surface from which fluid is received and or that lies in a plane of the opening of the fluid transporter) of no more than about 5 cm, and may have a largest vertical dimension (a dimension that is generally perpendicular to the lateral dimension) of no more than about 1 cm. The device may be generally lightweight, such as having a mass of no more than about 25 g prior to use in fluid collection. An adhesive may be positioned on a surface of the device and arranged to adhere the device to skin of the subject, e.g., so that blood or other fluid collection may occur without requiring a user to hold the device in place.

In another embodiment, a device for receiving bodily fluid from a subject includes a fluid transporter having a recess and an opening arranged to collect bodily fluid on skin of a subject. A flow activator may be located in the recess and arranged to interact with the skin at the opening to release the bodily fluid. An at least partially open capillary may extend along a surface of the recess and be arranged to conduct flow of the bodily fluid, e.g., to an inlet that leads to a storage chamber or other location where fluid may be collected. For example, the device may include a channel with an inlet, and the capillary may be in fluidic communication with the inlet. The inlet may be positioned in the recess as discussed above, and be arranged to receive fluid from the capillary. Likewise, the capillary may be arranged in a variety of different ways, e.g., may be fully open to the recess, may be within about 700 micrometers from the opening, have a substantially circular shape, have a cross-sectional shape that is substantially rectangular, be at least partially defined by at least two substantially parallel walls, form a closed circuit along the surface of the recess, be positioned in the recess such that at least a portion of the capillary is positioned within a distance of the opening that is about 10% of a largest dimension of the recess, be oriented in a plane that is substantially parallel to the opening, and so on. As noted above, a capillary arrangement may be used in conjunction with a beading disruptor having any suitable arrangement, or may be used without a beading disruptor.

In another embodiment, a method of receiving bodily fluid from a subject includes applying, to the skin of a subject, a device comprising a fluid transporter having a recess and a flow activator, a channel having an inlet in fluid communication with the recess, and a vacuum source having a pressure less than ambient pressure. The recess may be positioned to collect bodily fluid on the skin of the subject that is released by the flow activator, and thus the method may include receiving a bodily fluid from the skin into the recess. The bodily fluid may be moved into the recess and toward the channel and vacuum source due to a difference in pressure between the recess and the vacuum source. For example, with fluid presented at the opening to the recess, fluid communication between the vacuum source and the recess may be opened, causing the fluid to be drawn into the recess and toward the vacuum source, e.g., for collection in a storage chamber.

In another embodiment, a method of receiving bodily fluid from a subject includes applying, to the skin of a subject, a device comprising a fluid transporter having a recess and a flow activator, a channel having an inlet in fluid communication with the recess, and a vacuum source having a reduced pressure less than ambient pressure. A flow path between the recess and the vacuum source may be opened, and the inlet may be blocked or at least partially obstructed with at least a portion of a bodily fluid in the recess. A pressure within the recess may be increased relative to a pressure in the vacuum source, e.g., because of the blockage of the inlet, and the bodily fluid may be moved towards the vacuum source due to a difference in pressure between the recess and the vacuum source.

In another embodiment, a device for receiving bodily fluid from a subject includes a fluid transporter with an opening arranged to be adjacent to the skin of the subject when the device is applied to the skin of the subject, and an inlet of a microfluidic channel positioned such that at least a portion of the inlet is within about 0.7 millimeters of the opening of the fluid transporter. As in embodiments discussed above, the fluid transporter may include a recess in communication with the opening, a flow activator, a beading disruptor, etc. The device may have other features, such as a vacuum source, a channel or other flow path between the fluid transporter and the vacuum source, a storage chamber, an adhesive to adhere the device to a surface, etc.

In another embodiment, a device for receiving bodily fluid from a subject includes a fluid transporter with an opening arranged to be adjacent to the skin of the subject when the device is applied to the skin of the subject, and an inlet of a microfluidic channel positioned such that at least a portion of the inlet is within a distance to the opening of about 10% of a distance between the opening and a point within the fluid transporter perpendicularly furthest away from the opening.

In another embodiment, a device for receiving bodily fluid from a subject includes a fluid transporter having an opening adjacent to the skin of the subject when the device is applied to the skin of the subject and a first volume in fluid communication with the opening, a vacuum source having a second volume and a reduced pressure less than ambient pressure, and a seal arranged to control a fluid communication pathway between the fluid transporter and the vacuum source. A volumetric ratio of the first volume to the second volume may be at least about 1:6, e.g., at least about 1:10. The first and/or second volume may be less than about 10 ml.

In another aspect, the present invention is directed to a method of making one or more of the embodiments described herein, for example, devices for receiving a fluid such as blood from a subject. In another aspect, the present invention is directed to a method of using one or more of the embodiments described herein, for example, devices for receiving a fluid such as blood from a subject.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 3A-3M illustrate certain beading disruptors, in various embodiments of the invention;

DETAILED DESCRIPTION

Figure 1A:
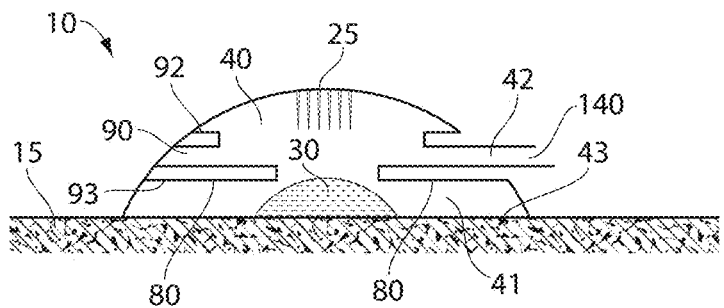
FIGS. 1A-1B illustrate a cross-sectional side view and a partial perspective view of a device in accordance with certain embodiments of the invention.

Aspects of the present invention relate to systems and methods for delivering materials to, and/or receiving fluids or other materials, such as blood or interstitial fluid, from subjects, e.g., to or from the skin and/or beneath the skin. In one aspect, the present invention is generally directed to devices containing a beading disruptor and/or capillary for facilitating the transport of fluids from a subject into a device. Beading disruptors may disrupt the "pooling" of bodily fluids such as blood on the surface of the skin or otherwise interact with such fluids. Also, certain aspects of the invention involve systems and techniques for receiving bodily fluids such as blood into a device, e.g., using a vacuum or reduced pressures. In some cases, a device may include a fluid transporter that receives fluid from a subject. The fluid transporter may include a recess or other applicator region where bodily fluids from the body are received, and a vacuum or reduced pressure may be used to withdraw the bodily fluids from the recess or applicator region into the device, e.g., into a vacuum source or a storage chamber. In some cases, a volume of the vacuum source may be larger than a volume of the fluid transporter recess. Still other aspects of the present invention are directed to kits involving such devices, methods of making such devices, methods of using such devices, and the like.

The fluid transporter may include an opening of any size and/or geometry that is constructed to receive fluid into the device. For example, the opening may lie in a two-dimensional plane or the opening may include a three-dimensional cavity, hole, groove, slit, etc. In some embodiments, the fluid transporter may also include a flow activator, such as one or more microneedles, arranged to cause fluid to be released from the subject, e.g., by piercing the skin of a subject. In some embodiments, if fluid may partially or fully fill an enclosure surrounding a flow activator, then the enclosure can define at least part of a fluid transporter.

It should be noted that a flow activator need not be included with all embodiments as the device may not necessarily employ a mechanism for causing fluid release from the subject. For instance, the device may receive fluid that has already been released due to another cause, such as a cut or an abrasion, fluid release due to a separate and independent device, such as a separate lancet, an open fluid access such as during a surgical operation, and so on. Additionally, fluid may be introduced into, or presented for introduction into, the device via urination, spitting, pouring fluid into the device, etc. If included, a flow activator may physically penetrate, pierce, and/or or abrade, chemically peel, corrode and/or irritate, release and/or produce electromagnetic, acoustic or other waves, other otherwise operate to cause fluid release from a subject. The flow activator may include a moveable mechanism, e.g., to move a needle, or may not require movement to function. For example, the flow activator may include a jet injector or a "hypospray" that delivers fluid under pressure to a subject, a pneumatic system that delivers and/or receives fluid, a hygroscopic agent that adsorbs or absorbs fluid, a reverse iontophoresis system, a transducer that emits ultrasonic waves, or thermal, radiofrequency and/or laser energy, and so on, any of which need not necessarily require movement of a flow activator to cause fluid release from a subject.

One non-limiting example of a device for receiving bodily or other fluids is now described with reference to FIGS. 1A and 1B; further details of this and other devices in accordance with certain aspects of the present invention are also described in further detail below. In this figure, device 10 is used to receive blood or other bodily fluids from the skin and/or from beneath the skin of a subject, although fluids may be received from other surfaces, such as an internal organ, a blood vessel, a floor, a table top, a sponge or other surface. However, in this embodiment, device 10 is shown positioned on skin 15 of a subject. Bodily fluid 30 is caused to reach the surface of the skin using one or more flow activators that include, for example, microneedles 25 as shown in this figure. In other embodiments, however, as discussed below and/or in documents incorporated herein by reference, other flow activator arrangements may be used in addition to and/or instead of flow activators that include microneedles 25. The bodily fluid collects on the surface of skin 15 and may pass through an opening 43 of the applicator region 40 (which includes recess 41) with the ultimate goal that at least some of the bodily fluid may enter device 10 through an inlet 42 to a channel 140.

The bodily fluid 30 on the surface of the skin typically will from a "pool" or a "bead" of liquid on the surface of the skin. However, this beading of the liquid may prevent, or at least delay, the movement of the bodily fluid 30 to inlet 42. To counter the natural tendency of the bodily fluid to form a bead on the surface, one or more beading disruptors 80 may be used. As depicted in FIGS. 1A and 1B, a beading disruptor 80 can include one or more protrusions extending from a portion of the surface defining a recess of the fluid transporter, e.g., the protrusions may extend from a wall that defines the recess 41. However, in other embodiments, the beading disruptor 80 may take other forms, instead of and/or in addition to including one or more protrusions. Upon contact of bodily fluid 30 with beading disruptor 80, at least a portion of the bead of fluid may be deformed or otherwise be caused to move towards inlet 42 for entry into the device, e.g., for processing, analysis, storage, etc. as is discussed in detail below.

In some embodiments, the fluid transporter may include a capillary that may facilitate fluid flow in the fluid transporter, e.g., may help move fluid from the recess 41 to the inlet 42. Fluid may move along the capillary with, or without, capillary action, e.g. it may be moved due to a vacuum, pneumatic force, gravity feed, or other suitable manner. Additionally, the capillary may be of any cross-sectional shape, length, diameter, and is not limited to any particular arrangement. The some cases, the capillary may be a capillary slit, e.g., including a relatively narrow groove. However, a capillary slit is only one arrangement and others are possible. For example, fluid may flow through a closed tube of any suitable cross-sectional shape. Also, it should be noted that a beading disruptor and capillary are not necessarily required in all embodiments; in certain cases, one or both of these may be absent.

Figure 1B:
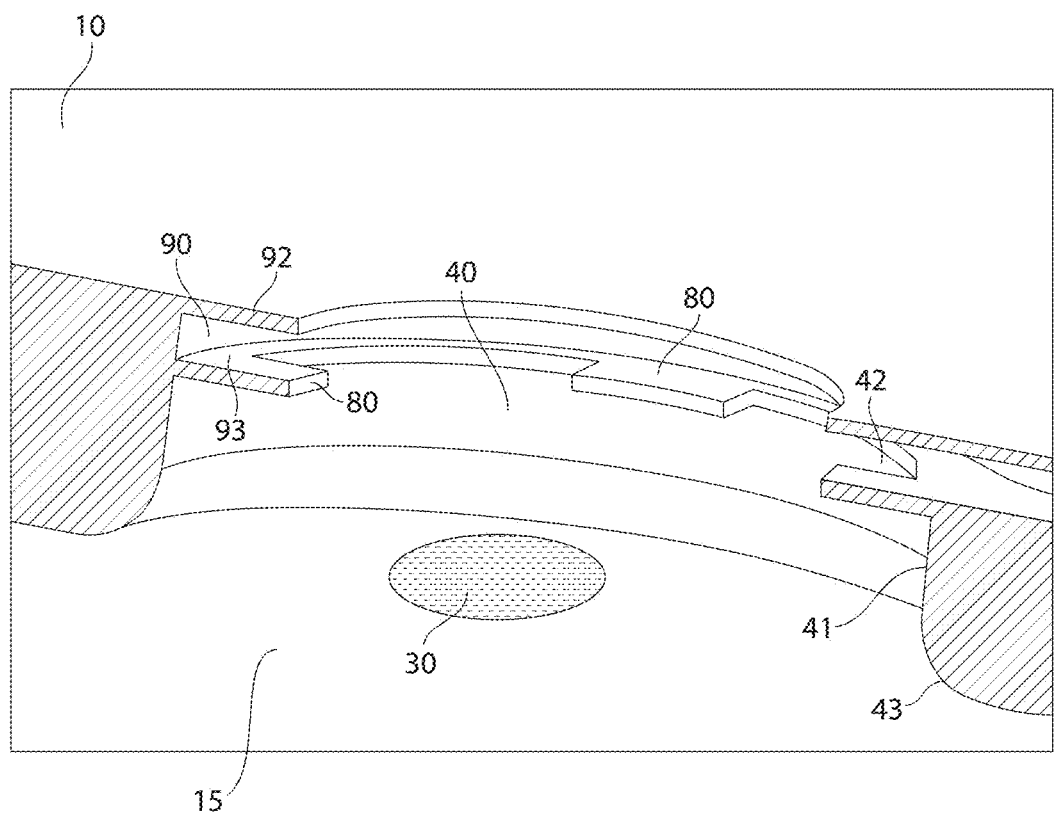

In the illustrative embodiment of FIGS. 1A and 1B, a capillary 90 may be positioned such that it adjacent the beading disrupter 80 and is in fluidic communication with inlet 42. In this embodiment, a single capillary 90 forms a closed circuit or circular flow path along the surface that defines the recess 41 (note that FIG. 1B has been cut in half for clarity). However, in other embodiments, more than one capillary 90 may be present and/or the capillary may not necessarily form a closed circuit along the surface of the recess. In addition, in this figure, the capillary is depicted as being oriented in a plane that is substantially parallel to the opening 43 and skin 15 of the subject, although in other embodiments, other orientations are also possible. Also, while in this embodiment the beading disruptor 80 is positioned between the capillary 90 and the opening 43, the capillary 90 may be positioned between the beading disruptor 80 and the opening 43 or in other ways. For example, in one embodiment, a capillary 90 may be formed into a protrusion of the beading disruptor. Capillary 90, in this example, is illustrated as being defined by two substantially parallel walls 92, 93, and a cross-sectional shape that is substantially rectangular, although other arrangements are possible, such as being defined by a cut, groove, recess or other feature having any suitable cross-sectional shape including circular, semi-circular and others.

A bodily fluid 30 on the surface of the skin may come into contact with capillary 90 during use, and at least a portion of the bodily fluid may then flow along capillary 90, e.g., due to capillary action. The capillary may thereby guide bodily fluid 30 towards inlet 42 into the device. As shown in FIG. 1A, beading disruptor 80 is formed as part of the bottom plane of capillary 90, such that at least a portion of the bead 30 of bodily fluid may be caused to enter capillary 90, and the fluid can then be moved towards inlet 42, e.g., as previously discussed. For example, the beading disruptor 80 may deform the shape of the bead so as to cause the bead 30 to extend upwardly in the recess 41 toward the capillary 90 so the fluid in the bead 30 is drawn into the capillary 90. The beading disruptor 80 may act in other ways, such as wicking fluid in the bead 30 to the capillary 90, etc. Surface treatments and/or material properties (e.g., to give desired hydrophobic/hydrophilic properties to portions of the beading disruptor may be used to help influence fluid movement.

Thus, in certain aspects, the present invention is generally directed to devices able to receive blood, interstitial fluid, or other bodily fluids from the skin of a subject, e.g., from the surface of the skin and/or from beneath the outer surface of the skin, or other mucosal surface, as well as methods of use thereof. The received fluid may be any suitable bodily fluid, such as interstitial fluid, other skin-associated material, mucosal material or fluid, whole blood, perspiration, saliva, plasma, serum, tears, lymph, urine, or any other bodily fluid, or combinations thereof. Substances received from a subject can include solid or semi-solid material such as skin, cells, or any other substance from the skin and/or beneath the skin of the subject. Substances that can be delivered to a subject in accordance with some embodiments of the invention include diagnostic substances, therapeutic substances such as drugs, and the like. Various embodiments of the invention are described below in the context of delivering or receiving a fluid, such as blood or interstitial fluid, from the skin and/or beneath the skin. It is to be understood that in all embodiments herein, regardless of the specific exemplary language used (e.g., receiving blood), the devices and methods of other embodiments of the invention can be used for receiving any substance from the skin of the subject, and/or for delivering any substance to the subject, e.g., to the skin of the subject, whether on, in or beneath the skin's surface.

In some cases, the device may contain a flow activator (for example, one or more needles or microneedles). As used herein, "needles" refers to any size needle structure, including microneedles. Examples of flow activators are discussed in detail below. In some cases, the device may be used to pierce the skin of the subject, and fluid or other material can then be delivered to and/or received from the skin of the subject. Thus, it should be understood that in the discussions herein, references to receiving a fluid "from the skin" includes embodiments in which a fluid is delivered and/or received through the surface of the skin. For example, a fluid may be delivered into or received from a layer of skin in one embodiment, while in another embodiment a fluid may be delivered into or received from a region just below the skin of the subject, e.g., passing through the surface of the skin, as opposed to other routes of administration such as oral delivery. The subject is usually human, although non-human subjects may be used in certain instances, for instance, other mammals such as a dog, a cat, a horse, a rabbit, a cow, a pig, a sheep, a goat, a rat (e.g., *Rattus norvegicus*), a mouse (e.g., *Mus musculus*), a guinea pig, a hamster, a primate (e.g., a monkey, a chimpanzee, a baboon, an ape, a gorilla, etc.), or the like.

Accordingly, various aspects of the present invention are generally directed to devices for receiving bodily fluids from a subject. The device may contain an applicator region for facilitating the movement of the bodily fluids into an inlet of the device. As discussed in detail below, the applicator region may be relatively small in some embodiments, and/or the device may contain one or more beading disruptors and/or capillaries. In some cases, the device may also contain a flow activator, such as one or more needles or microneedles, to facilitate transport a bodily fluid from the skin and/or from beneath the skin to the applicator region. In certain embodiments, the device may be self-contained, for example, containing a vacuum source that assists in the movement of bodily fluids into the device, e.g., as discussed below. The device may also contain channels such as microfluidic channels, sensors, displays, or the like.

One aspect of the present invention is generally directed to an applicator region. The applicator region may be positioned to collect a bodily fluid on the skin of the subject that is transported thereto by a flow activator. Non-limiting examples of bodily fluids include blood or interstitial fluid, as is discussed herein. The flow activator may be applied to the skin, and optionally received from the skin, in order to cause the transport of a bodily fluid to the applicator region of the device. For example, a flow activator may include one or more needles or microneedles, a hygroscopic agent, etc., as is discussed herein. The flow activator can be centered with respect to the applicator region in certain embodiments; in other embodiments, however, the flow activator is not centered within the applicator region, and in some embodiments, the flow activator may not necessarily enter the applicator region. The applicator region may be any portion of the device that is sized and/or positioned to collect bodily fluids, and in some cases, the applicator region may have a relatively small size and/or volume.

In one set of embodiments, the volume of the applicator region is defined relative to the opening of the applicator region, or the portion of the applicator region that is adjacent to the skin of the subject when the device is applied to the skin of the subject. In some embodiments, the applicator region may include a recess or an indentation within the base of the device, which can receive a fluid from the surface of the skin. The applicator region may have any suitable shape. For example, the applicator region can be generally hemispherical, semi-oval, rectangular, irregular, etc. The volume of the applicator region can be relatively small in some embodiments. For example, the volume of the applicator region may be less than about 10 ml, less than about 8 ml, less than about 5 ml, less than about 3 ml, less than about 2 ml, less than about 1.5 ml, less than about 1 ml, less than about 800 microliters, less than about 600 microliters, less than about 500 microliters, less than about 400 microliters, less than about 300 microliters, less than about 200 microliters, or less than about 100 microliters. Smaller volumes may be desirable, for example, to minimize the amount of bodily fluid collected within the applicator region before the bodily fluid is able to be transported into the device, e.g., through an inlet within the applicator region into the device.

In some instances, the applicator region, e.g., a recess of the applicator region, may have a small volume relative to a vacuum source contained within the device, e.g., in embodiments where a vacuum source is present in the device. In some cases, the vacuum source may be in the form of a vacuum chamber. The vacuum source may be a pre-packaged vacuum source as is discussed below. Without wishing to be bound by any theory, it is believed that a relatively small applicator region will result in less gas being drawn into the vacuum source upon the creation of a fluid communication pathway between the vacuum source and the applicator region, e.g., as is discussed herein. This may allow more of the vacuum or reduced pressure to be able to draw more bodily fluid into the device. Thus, for example, the ratio between the volume of the applicator region and the volume of the vacuum source can be at least about 1:5, at least about 1:6, at least about 1:8, at least about 1:10, at least about 1:12, at least about 1:15, etc.

In one set of embodiments, the applicator region may have a recess with a variable size or geometry. For example, an actuator or a deformable structure as discussed below may be used to alter the shape and/or size of the applicator region during use. In one set of embodiments, a deformable structure such as a "snap dome" may be in a first configuration prior to use, causing the applicator region to adopt a first shape and/or size, and the deformable structure may have a second, different configuration once it is triggered, thereby causing the applicator region to adopt a second shape and/or size. In some cases, the applicator region can be formed out of a deformable material, and/or the applicator region may contain one or more folds or pleats that allows the applicator region to change its shape and/or size.

Figure 2A:
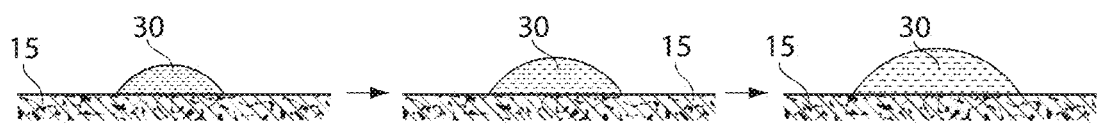
FIGS. 2A-2B illustrate the formation of a pool of bodily fluid on the surface of the skin, in certain embodiments of the invention.

The applicator region may contain, in one set of embodiments, one or more beading disruptors for disrupting the pooling of bodily fluids on the surface of the skin. This is now illustrated with reference to the example shown in FIG. 2. In FIG. 2A, a bodily fluid 30, such as blood, is present on the surface of the skin 15, e.g., transported thereto by one or more flow activators such as is discussed herein. The bodily fluid typically forms a bead or pool on the surface of the skin, instead of wetting the skin. The shape of the bead (e.g., the contact angle) may be controlled by the condition of the skin (for example, its hydrophobicity) and/or the bodily fluid on the skin. For example, the bodily fluid may pool on the skin of the subject at a contact angle of about 30°, about 40°, about 45°, about 50°, about 55°, etc. in a substantially circular region on the surface of the skin. In many cases, the skin is relatively hydrophobic, thereby causing the bodily fluid to form a bead instead of wetting or spreading on the surface of the skin. Furthermore, as more bodily fluid enters the bead, the bead typically grows in size while keeping substantially the same shape. Thus, before the bead is able to contact a surface of the applicator region, a certain amount of bodily fluid must flow from the body into the bead on the surface of the skin.

Figure 2B:
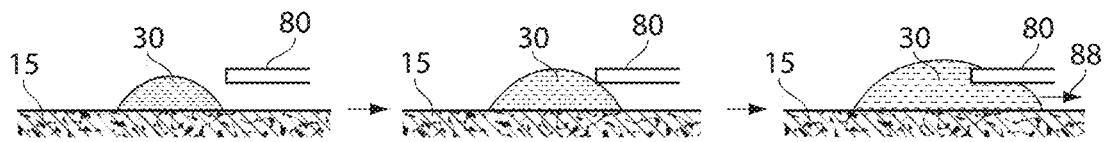

In FIG. 2B, beading disruptor 80 is also shown, in addition to bodily fluid 30 on the surface of skin 15. Beading disruptor 80 is shaped and positioned to disrupt the shape of bodily fluid 30 to prevent or at least alter the ability of bodily fluid 30 to pool on the surface of the skin. Thus, in this example, bodily fluid exiting the skin within the applicator region (e.g., from the center of the applicator region) will first come into contact with the beading disruptor before contacting other portions of the device, which can disrupt the shape of the pool of bodily fluid on the surface of the skin. In some cases, as is shown in this figure, at least a portion of bodily fluid 30 may be caused to move away from the pool of fluid, e.g., towards an inlet of the device, or another suitable location as is shown by arrow 88 and/or upwardly and over the disruptor 80, due to the presence of beading disruptor 80.

The beading disruptor may take any of a variety of forms. In one set of embodiments, the beading disruptor is present within an applicator region, such as a recess, into which a bodily fluid is transported by a flow activator, for example, one or more needles and/or microneedles. More than one beading disruptor may also be present, in some embodiments.

In one set of embodiments, the beading disruptor may take the form of one or more protrusions, e.g., as is illustrated in FIG. 1B or in FIGS. 3A-3M. If more than one protrusion is present, the protrusions may have the same or different shapes or sizes and/or may be made of the same or different material. The protrusions can have any suitable cross-sectional shape or size, for example, substantially square, rectangular, triangular, trapezoidal, circular, irregular, etc. The protrusion may have any shape or aspect ratio. For example, the protrusions may have a shape that is square, rectangular, triangular, trapezoidal, circular, a portion of a circular sector, etc. Non-limiting examples of such protrusions are shown in FIGS. 3A-3M.

In one set of embodiments, a protrusion may have a first end, a second end, a length and a width and may be arranged so that a ratio of the width to the length, e.g., the width at the first end to the length between the first end and the second end, may be about 1, greater than 1, or less than 1 For example, in FIG. 3I, a protrusion is shown having a first end 110 contacting a surface 112 (e.g., which defines at least a portion of a recess of an applicator region) and a second end 115 extending away from the surface, e.g., towards the geometrical center of the applicator region. The width of the first end is shown as "A" and the distance between the first end and the second end (a length) is shown as "B" in this figure. This ratio may have any suitable value. For example, the ratio may be about 1 (i.e., such that the protrusion is substantially square, e.g., as is shown in FIG. 3A), less than 1 as is shown in FIG. 3I, or greater than 1 as is shown in FIG. 3J. As specific non-limiting examples, this ratio may be less than or greater than 1, less than or greater than 2, less than or greater than 3, less than or greater than 4, less than or greater than 5, less than or greater than 7, less than or greater than 10, etc.

Figure 4A:
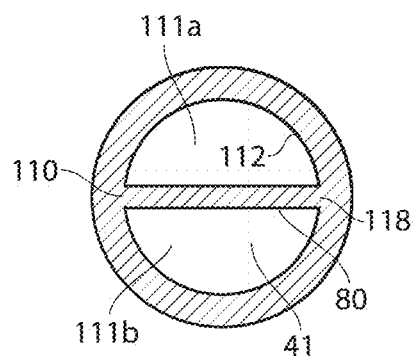
FIGS. 4A-4E illustrate various beading disruptors, in accordance with some embodiments of the invention.
Figure 4B:
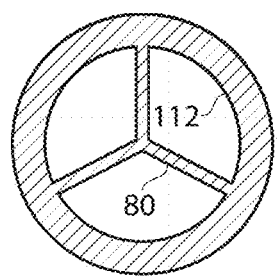
Figure 4C:
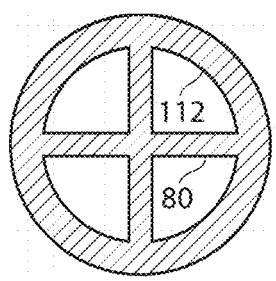

It should be understood, however, that the beading disruptor is not necessarily limited to projections or protrusions that are cantilevered from a wall or other surface. For example, in certain embodiments, the beading disruptor may be connected at two portions to a surface defining the applicator region, e.g., forming a "span" across a recess 41. An example is shown in FIG. 4A, where the beading disruptor connects to a first portion of the surface or wall 112 defining a recess 41 at a first end 110 of beading disruptor 80 and a second portion of the surface or wall 112 at a second end 118 of beading disruptor 80. In this figure, the recess 41 is separated into a first portion 111*a* and a second portion 111*b* by the beading disrupter 80. (In contrast, in FIG. 3G, the recess 41 is not divided into separate portions.) In some embodiments, the beading disruptor has a portion located at the geometric center of the recess 41, but in other embodiments, the geometric center of the recess 41 is not occupied by a portion of a protrusion. More complex shapes may also be used in some embodiments, for example, where the beading disruptor physically contacts the surface 112 at three ends, at four ends (e.g., defining an "X" or a cross shape, as shown in FIG. 4C), or more in some cases. Non-limiting examples of such configurations are shown in FIGS. 4B and 4C.

In some embodiments, the beading disruptor may exhibit rotational symmetry, for example, in cases where the beading disruptor is contained within an applicator region that has a generally circular cross-section. In other embodiments, however, the beading disruptor may not necessarily exhibit rotational symmetry. For example, the beading disruptor may exhibit 180° rotational symmetry, 120° rotational symmetry, 90° rotational symmetry, 60° rotational symmetry, or the like. In certain embodiments, the beading disruptor may be circular or have a shape circumscribable by a circle, and/or the beading disruptor may have a shape circumscribed by the applicator region.

Figure 4D:
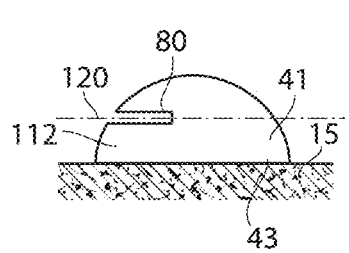
Figure 4E:
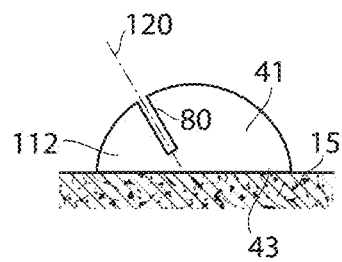

As is shown in many of these figures, the beading disruptor may lie in a plane that is substantially parallel to the opening 43 (and parallel to a surface of the skin when the device is placed on the skin), as is shown in FIG. 4D with a plane 120 of the beading disruptor 80 positioned above the opening 43. In other embodiments, however, the plane 120 of the beading disruptor may intersect the skin of the subject. An example of such an embodiment is shown in FIG. 4E. In addition, it should be understood that the beading disruptor need not be arranged so that the disruptor, or all portions of the disruptor, lie in a single plane. For example, the beading disruptor can have portions that define or lie in a generally partial spherical shape, a conical shape, or a more complex 3-dimensional shape.

Figure 4F:
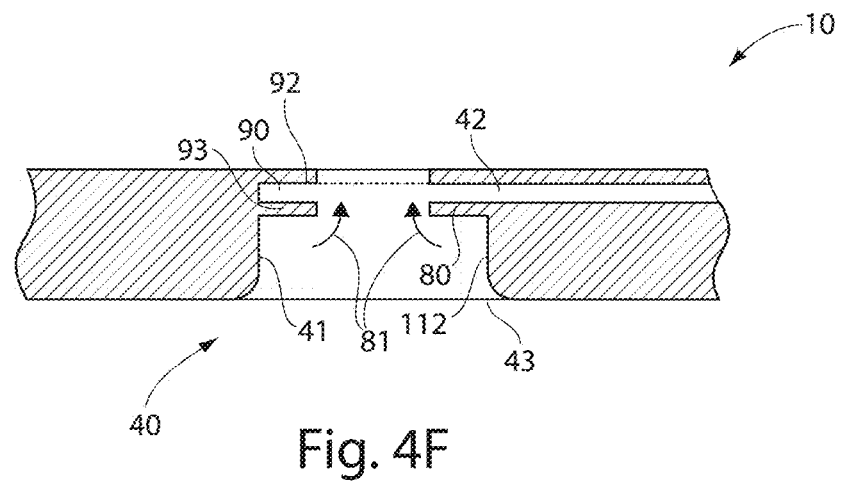
FIG. 4F shows a cross-sectional side view of the FIG. 1B embodiment illustrating beading disruptor movement in a vertical direction in one example.

In another aspect of the invention, a beading disruptor, or at least portions of the beading disruptor, may be arranged to interact with skin or other materials or surfaces that enter into a fluid transporter recess. Such interaction may help ensure proper flow of fluid in the fluid transporter (e.g., from the recess 41 to the inlet 42). For example, in some embodiments, application of a vacuum or other relatively low pressure to the recess 41 may act to draw skin 15 or other material at the opening 43 into the recess 41. In some cases, the skin 15 may be drawn relatively far into the recess 41 and may in some instances impede flow of fluid to the capillary 90 and/or to the inlet 42. For example, the skin 15 may be drawn beyond the beading disruptor 80 and block a flow path to the capillary 90 or inlet 42. In some embodiments, the beading disruptor 80 may be arranged to help resist the movement of skin or other surface or material into the fluid transporter. In one embodiment, the beading disruptor 80 may include protrusions that are relatively rigid and resist upward movement (e.g., in the direction of arrows 81 in FIG. 4F) that might be caused by the movement of skin into the recess 41. In other embodiments, the protrusions may be arranged to be somewhat flexible and move in the direction of the arrows 81 in FIG. 4F at least to a certain extent, but once the protrusions are moved to a certain degree, become more resistant to further movement. This may help stop excessive drawing of skin or other surface into the recess 41 and allow for desired fluid flow. For example, the protrusions may be made cantilevered from the surface 112 and made to flex upwardly when contacted by skin. However, stops or other features (not shown) may be provided to contact the protrusions at points located away from the surface 112 (e.g., the stops may depend from the upper wall 92 and prevent movement of the protrusions beyond a certain point). Alternately, a spring action of the protrusions may resist upward movement to increasing degrees as the protrusions are moved upwardly.

In another aspect of the invention, protrusions or other beading disruptor features may be arranged to accommodate conditions in which skin is not sufficiently drawn into a fluid transporter recess (e.g., because of insufficient vacuum draw at the opening 43 due to leakage) and/or fluid does not enter the recess to a sufficient degree (e.g., because of a relatively low volume release of fluid from skin). For example, protrusions of a beading disruptor 80 may depend downwardly as shown generally in FIG. 4E so that distal ends of the protrusions may contact skin and/or fluid at a relatively low level in the recess 41. Such an arrangement may help the beading disruptor 80 to influence flow to the inlet 42, capillary 90 or other area so as to compensate for lower than expected fluid volume in the recess 41. This arrangement may also aid the protrusions in resisting excessive entry of skin into the recess 41, e.g., because the protrusions may first contact the skin at a relatively low point in the recess, near the opening 43, and thereby more robustly resist entry of the skin into the recess 41. In another arrangement, protrusions (or at least some of the protrusions) can be configured so as to be relatively long and flexible (e.g., hair-like) so that the protrusions can extend to, near or beyond the opening 43. Such protrusions may be effective in influencing flow of fluid at or near the opening 43 to the capillary 90 or inlet 42, particularly if the protrusions are provided with a suitable hydrophilic feature (a coating or made of a suitable material). In some embodiments, such long and thin protrusions may be arranged to avoid interference with the action of a flow activator, e.g., by being deployed after flow activator action or by being suitably small to not interfere with needle action.

In some embodiments, a beading disruptor 80 may include protrusions and other features that serve different functions. For example, relatively short and robust protrusions may be provided at inner regions of a recess 41 to help resist excessive entry of skin into the recess 41. In addition, relatively long, thin and flexible protrusions may be provided so that distal ends of the protrusions may extend to outer regions of the recess 41 near the opening 43. These long and flexible protrusions may help wick or otherwise influence flow in low fluid volume and/or reduced skin penetration situations.

Figure 4G:
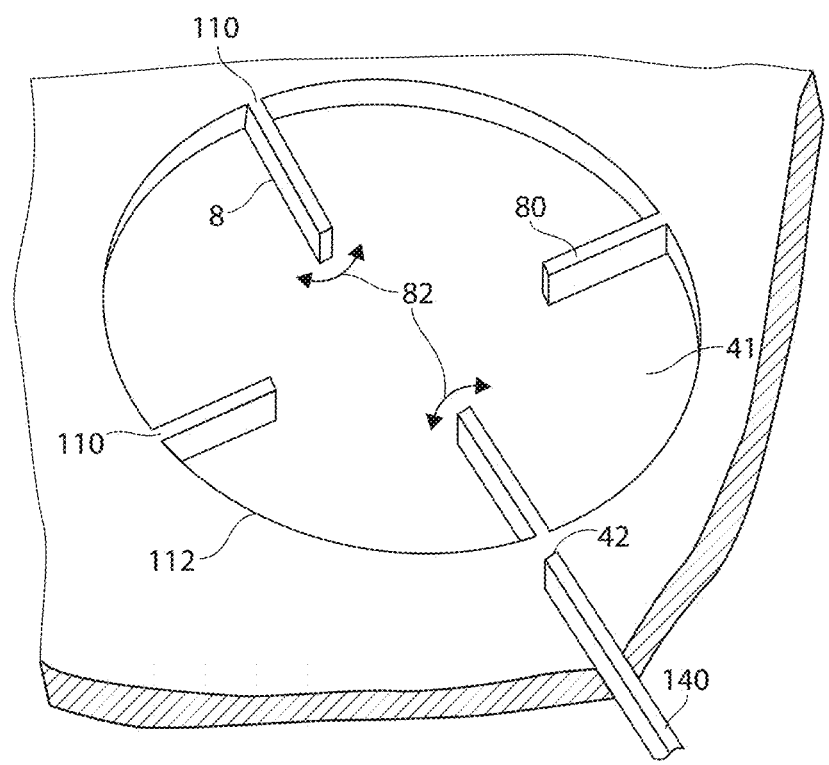
FIG. 4G shows a perspective view of a beading disruptor arrangement like that of FIG. 3D in which the protrusions of the beading disruptor are laterally movable.

While embodiments have been described above in which protrusions may be made flexible or otherwise movable in a vertical direction (e.g., toward and away from an opening 43 to a recess 41), protrusions may be made flexible in other directions. For example, FIG. 4G shows an embodiment in which protrusions 80 are made to be flexible in lateral directions, e.g., in directions along the arrows 82 so that distal ends of the protrusions may move toward the wall surface 112. Such a feature may be provided by making the protrusions to have a relatively high aspect ratio, i.e., so that a thickness of the protrusions (a vertical dimension) is larger than a width A of the protrusions. (See FIGS. 3I-3J regarding the width A dimension.) Thus, the protrusions may be relatively resistant to vertical movement, e.g., in the direction of arrows 81 in FIG. 4F, yet be relatively easily moved in lateral directions along the arrows 82. This feature may help the protrusions not only resist movement of skin into the recess 41, but also help to wick or otherwise influence fluid near the wall 112 to flow in a desired way, such as toward a first end 110 of the protrusions. Of course, while the embodiment of FIG. 4G shows a beading disruptor 80 with four protrusions, more or fewer protrusions may be used, and the protrusions may have the same or different features. For example, laterally flexible protrusions (to help influence flow near the recess wall 112 and resist skin entry into the recess 41) may be coupled with vertically flexible protrusions (to help accommodate low volume or skin entry conditions).

As noted above, protrusions or other features of a beading disruptor 80 may help influence flow to a capillary 90, an inlet 42 or other location. In the embodiment of FIG. 4G, one or more protrusions may be made to include a capillary, wicking structure, hydrophilic surface feature, and/or other arrangement extending along part or all of the length of the protrusion so as to cause fluid flow along the protrusion to an inlet 42. In some embodiments, a portion of a protrusion may extend within, or define, a channel that leads to a storage chamber or other location for fluid. Alternately, protrusions may be made to help influence flow to a capillary 90 at the surface 112 (see FIG. 4F) so that the capillary 90 may conduct the fluid along the capillary 90 to an inlet 42. In one embodiment, a protrusion may include an anticoagulant or other coating, e.g., on an upper surface of the protrusion on a side opposite the opening 43, to help cause flow along the protrusion to a capillary, inlet or other location. As will be understood, an anticoagulant may help the flow of blood by slowing or reducing clotting or other coagulation.

Figure 5:
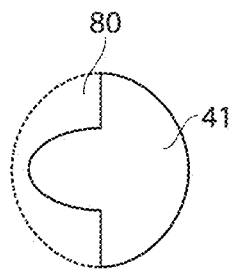
FIG. 5 illustrates a beading disruptor in yet another embodiment of the invention.

In one set of embodiments, the beading disruptor may comprise a "shelf" or a "lip" along a portion of the applicator region. One example of such a configuration is shown in FIG. 3G. As another example, as shown in FIG. 5, the beading disruptor may be positioned along a portion of a wall of the applicator region, for example, such that an imaginary plane can be positioned that divides the applicator region into two halves that have the same volume such that only one of the two halves comprises the beading disruptor. In this figure, beading disruptor 80 is present along a portion of a surface defining applicator region 40.

In some embodiments, the beading disruptor can be positioned to facilitate the flow of a bodily fluid to an inlet to the device, e.g., to the inlet of a channel such as a microfluidic channel within the device. In some cases, as is discussed below, the beading disruptor may form a portion of a capillary that facilitates the flow of a bodily fluid to an inlet to the device.

In one set of embodiments, the applicator region contains one or more capillaries that can facilitate the flow of a bodily fluid to an inlet of the device. A non-limiting example of a capillary is shown with respect to FIG. 6. In this figure, the surface of a portion of applicator region 40 of device 10 is illustrated, including a capillary 90 that is in fluid communication with inlet 42 of the device. In this figure, capillary 90 is defined by walls 92, 93 which are substantially parallel to each other, thereby forming capillary 90. In some embodiments, at least a portion of capillary 90, such as one or both of walls 92, 93, may also be used as a beading disruptor.

Figure 6A:
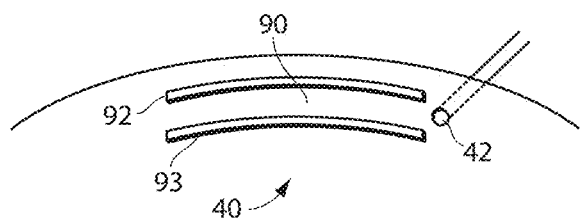
FIGS. 6A-6B illustrate various capillaries in accordance with certain embodiments of the invention.
Figure 6B:
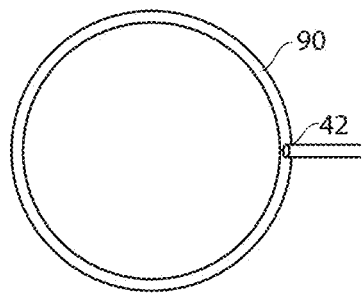

Although only one capillary is shown in FIG. 6, in other embodiments, more than one capillary may be present, which may be lead to one or more inlets of the device. The capillary can have any suitable configuration to facilitate the flow of a bodily fluid along at least a portion of the capillary, e.g., through capillary action. In some cases, the capillary may encircle or circumscribe at least a portion of the applicator region. For instance, the capillary may form a closed circuit such that the flow of bodily fluid in any direction along the capillary will reach the inlet. One example of this can be seen in FIG. 6B with capillary 90 and inlet 42.

The capillary may have any suitable size. For example, the capillary may have an average cross-sectional dimension (e.g., perpendicular to the flow of fluid therein) of less than about 10 mm, less than about 9 mm, less than about 8 mm, less than about 7 mm, less than about 6 mm, less than about 5 mm, less than about 4 mm, less than about 3 mm, or less than about 2 mm, less than about 1 mm, less than about 500 microns, less than about 300 microns, or less than about 100 microns. For example, the capillary may have an average cross-sectional diameter of between about 100 and about 700 micrometers, or between about 300 and about 500 micrometers. The average cross-sectional dimension may be constant or may change along the capillary, e.g., to promote flow towards the inlet. The capillary can have any cross-sectional shape, for example, circular, oval, triangular, irregular, square or rectangular (having any aspect ratio), or the like. The capillary may have, in certain embodiments, a cross-sectional shape and/or area that remains substantially constant throughout the capillary.

In some embodiments, the entire capillary may be exposed to the applicator region; in other embodiments, however, a portion of the capillary may not necessarily be open to or exposed to the applicator region. In some cases, some or all of the capillary is in fluidic communication with the applicator region, for example such that substantially each portion of the capillary can be reached by a fluid within the applicator region. For instance, in certain embodiments, no portion of the capillary is further than about 10 micrometers, about 5 micrometers, about 3 micrometers, or about 1 micrometer away from a portion of the applicator region, as determined by flow of a fluid from the applicator region to the capillary. In some embodiments, no portion of the capillary may be further than about 5 mm, about 3 mm, about 1 mm, about 500 micrometers, about 300 micrometers, about 100 micrometers, about 50 micrometers, about 30 micrometers, or about 10 micrometers away from a portion of the applicator region, as determined by flow of a fluid from the applicator region to the capillary, e.g., depending on the size of the applicator region. In some embodiments, no portion of the applicator region is greater than about 5 mm, about 3 mm, about 1 mm, about 500 micrometers, about 300 micrometers, about 100 micrometers, about 50 micrometers, about 30 micrometers, or about 10 micrometers away from a portion of the capillary.

The capillary may be positioned in any suitable location within the applicator region. In some cases, a capillary may be positioned near an inlet in the applicator region, or such that at least a portion of the capillary is at substantially the same distance away from the skin of the subject as an inlet is when the device is positioned on the skin of a subject. In some embodiments, at least a portion of a capillary may be positioned relatively close to the skin of the subject, e.g., to facilitate the transport of bodily fluids from the skin. For instance, at least a portion, or all, of a capillary may be positioned within about 50%, about 30%, about 20%, about 15%, about 10%, about 5% of the opening of the applicator region, e.g., relative to the distance between the opening of the applicator region and a point within the applicator region perpendicularly furthest away from the opening. In some embodiments, a capillary may be oriented substantially parallel to the opening.

The applicator region may also contain one or more inlets for introduction of a bodily fluid from the subject into the device. For example, the inlet can be an inlet to a fluid communication pathway, a channel such as a microfluidic channel, or the like, which may extend to various portions of the device. The fluid communication pathway into the device may proceed to or otherwise fluidly communicate with, for example, a vacuum source, a storage or collection chamber, a separation membrane (see, e.g., a U.S. provisional patent application 61/480,941, filed Apr. 29, 2011, entitled "Plasma or Serum Production and Removal of Fluids under Reduced Pressure," incorporated herein by reference in its entirety), a portion of the device containing a sensor, or the like, and/or one or more of these. It should be noted that a fluid communication pathway, e.g., between a vacuum source and a fluid transporter opening, need not necessarily involve the opening of a valve or other device that blocks flow, but instead may involve the creation of suitable vacuum to cause flow.

As non-limiting examples, a fluid communication pathway may include one or more microfluidic channels having an average cross-sectional diameter of between about 100 and about 700 micrometers, or between about 300 and about 500 micrometers. Other examples of fluid communication pathways are discussed herein, including other channels and microfluidic channels.

The inlet may be positioned in any suitable location within the applicator region, and one or more inlets may be present. In some cases, an inlet (or at least a portion thereof) may be positioned relatively close to the skin of the subject. For example, the inlet may be positioned such that at least a portion of the inlet is positioned within about 5 mm, within about 3 mm, within about 1 mm, within about 0.7 mm, within about 0.5 mm, or within about 0.3 mm of the skin or the opening of the applicator region. As additional examples, the inlet (or at least a portion thereof) may be positioned to be within about 50%, within about 30%, within about 20%, within about 10%, or within about 5% of the skin of the subject or the opening of the applicator region, where the percentage may be taken relative to the distance between the opening of the applicator region and a point within the applicator region perpendicularly furthest away from the opening.

As mentioned, in some aspects, the device may include channels such as microfluidic channels. In some cases, the microfluidic channels are in fluid communication with a fluid transporter that is used to deliver to and/or receive fluids from the skin. For example, in one set of embodiments, the device may include a hypodermic needle or other needle (e.g., one or more microneedles) that can be inserted into the skin, and fluid may be delivered into or through the skin via the needle and/or received from the skin via the needle. The device may also include one or more microfluidic channels to contain fluid for delivery to the needle, e.g., from a source of fluid, and/or to receive fluid that is received from the skin and/or beneath the skin, e.g., for delivery to an analytical chamber within the device, to a reservoir for later analysis, or the like.

In some cases, more than one chamber may be present within the device, and in some cases, some or all of the chambers may be in fluidic communication, e.g., via channels such as microfluidic channels. In various embodiments, a variety of chambers and/or channels may be present within the device, depending on the application. For example, the device may contain chambers for sensing an analyte, chambers for holding reagents, chambers for controlling temperature, chambers for controlling pH or other conditions, chambers for creating or buffering pressure or vacuum, chambers for controlling or dampening fluid flow, mixing chambers, or the like.

A "channel," as used herein, means a feature on or in an article (e.g., a substrate) that at least partially directs the flow of a fluid. In some cases, the channel may be formed, at least in part, by a single component, e.g. an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

A channel may have any aspect ratio (length to average cross-sectional dimension), e.g., an aspect ratio of much less than 1 (as is the case with a simple opening in a thin wall element), at least about 2:1, more typically at least about 3:1, at least about 5:1, at least about 10:1, etc. A channel may include characteristics that facilitate control over fluid transport, e.g., structural characteristics and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus).

In one set of embodiments, the device may include a microfluidic channel. As used herein, "microfluidic," "microscopic," "microscale," the "micro-" prefix (for example, as in "microchannel"), and the like generally refers to elements or articles having widths or diameters of less than about 1 mm, and less than about 100 microns (micrometers) in some cases. In some embodiments, the microchannels may be of a particular size or less, for example, having a width or diameter of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In all embodiments, specified widths can be the minimum distance across the channel cross-section or the maximum distance across the channel cross-section. In some cases, the cross-section of the microfluidic channel may be a rectangle. The rectangular cross-section may have a rectangular height that is perpendicular to the base and a rectangular width that is parallel to the base. The rectangular height may be from about 10 microns to about 1000 microns. The rectangular width may be from about 10 microns to about 2500 microns. In some embodiments, larger channels may be used instead of, or in conjunction with, microfluidic channels for any of the embodiments discussed herein. For example, channels having widths or diameters of less than about 10 mm, less than about 9 mm, less than about 8 mm, less than about 7 mm, less than about 6 mm, less than about 5 mm, less than about 4 mm, less than about 3 mm, or less than about 2 mm may be used in certain instances. In some cases, the element or article includes a channel through which a fluid can flow.

As used herein, a "cross-sectional dimension," in reference to a fluidic or microfluidic channel, is measured in a direction generally perpendicular to fluid flow within the channel. For example, in the case of a circular cross-section, a cross-sectional dimension may be the diameter. In the case of a rectangular cross-section, a cross-sectional dimension may be the width, height, diagonal, etc., and the like. Other cross-sectional shapes will have corresponding dimensions that may serve as a cross-sectional dimension. Thus, for instance, the microfluidic channel may have an average cross-sectional dimension of less than about 1 mm, less than about 500 microns, less than about 300 microns, or less than about 100 microns. In some cases, the microfluidic channel may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

In some embodiments, the beading disruptor, capillary and microfluidic channel may be made from a polymer, for example, an elastomeric polymer such as polydimethylsiloxane ("PDMS"), polytetrafluoroethylene ("PTFE" or Teflon®), or the like. Other possible materials are elaborated on in more detail in later sections. For example, the beading disruptor may be made of any suitable material or combination of materials, including metals, plastics or polymers, glass, composite materials, fibers, fabrics (whether woven or not), membranes, porous materials, etc. The beading disruptor, capillary and microfluidic channel may be coated with a hydrophilic substance such as Polyvinyl alcohol, Polyvinylpyrrolidone, Polyurethanes, Polyacrylic acid, Polyethylene oxide, Polyethylene glycol, Polysaccharides, albumin, Pluronics, Polysorbates, Triton, or antithrombogenic coatings such as heparin, hirulog, hirudin and others to improve wetting.

In some aspects, a seal or other suitable apparatus may be arranged to control a fluid communication pathway, for example, between the inlet and a vacuum source and/or a storage chamber. A closed seal blocks and/or eliminates fluid communication and an open seal opens and/or enables fluid communication. For example, the seal may comprise a valve or a pierceable surface that can be opened. However, enabling fluid communication between a vacuum source and a fluid transporter opening need not necessarily involve the opening of a valve or other device that blocks flow, but instead may involve the creation of suitable vacuum to cause flow. In some embodiments, the seal can be reversibly manipulated, i.e., the seal may also be used to stop fluid communication (for example, a valve that can be opened or closed). In other embodiments, however, the seal cannot be reversibly manipulated (for example, a punctured seal that cannot be re-sealed). The seal can be actuated using any suitable technique, e.g., automatically, remotely, manually, etc. In some cases, the seal may be self-actuating, e.g., upon application to the skin of a subject. The seal may be actuated once, or multiple times in some cases. The seal may be actuated, for example, by pushing a button, flipping a switch, moving a slider, turning a dial, moving a punch, or the like. The subject, and/or another person, may activate the seal. In some embodiments, the seal, or at least a portion thereof, may also serve as an activator, as discussed herein. Other examples of seals are discussed a U.S. provisional patent application 61/480,977, entitled "Delivering and/or Receiving Fluids," filed Apr. 29, 2011, incorporated herein by reference in its entirety.

Figure 7A:
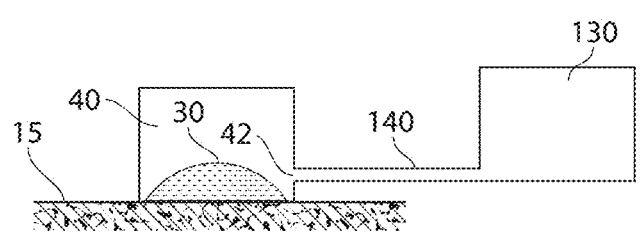
FIGS. 7A-7C illustrate the entry of fluid into a device, in still another embodiment of the invention.
Figure 7B:
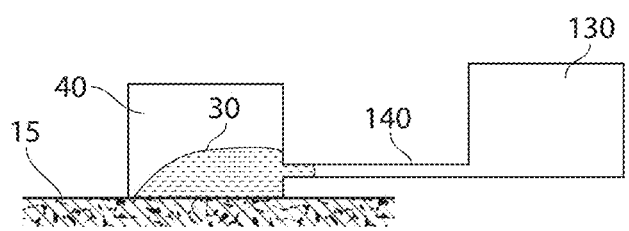
Figure 7C:
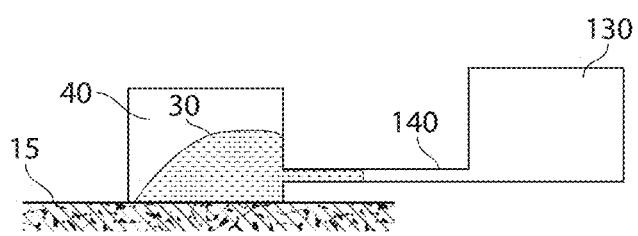

In some aspects, during use, the entry of a bodily fluid into the inlet may alter pressures within the device, for example within the applicator region, which may be used to facilitate the transport of bodily fluid into the device. Referring now to FIG. 7, in FIG. 7A, device 10 contains an applicator region 40 and a vacuum source 130 having a reduced pressure less than ambient pressure, connected through inlet 42 of fluid communication pathway or channel 140. It should be understood that vacuum source 130 is shown here for illustrative purposes only; in other embodiments, the fluid communication pathway may be in fluid communication with other portions of the device having reduced pressure, for example, a storage or collection chamber, a portion of the device containing a sensor, etc., instead of and/or in addition to vacuum source 130. Similarly, while fluid communication pathway 140 is shown in FIG. 7 as a straight channel, in other embodiments, the fluid communication may have a more tortuous pathway, proceed through chambers, membranes, valves, etc., or the like. For instance, in some cases, as discussed herein, a seal may be used to control the fluid communication pathway.

In FIG. 7A, initially, vacuum source 130 and applicator region 40 may have substantially the same pressure (which may be a reduced pressure), e.g., upon the opening of a suitable fluid communication pathway 140 that allows the two to be in fluidic communication. Bodily fluid 30 entering applicator region 40 (e.g., as transported thereto by a suitable fluid transporter) from skin 15 begins to accumulate therein, eventually blocking or otherwise being positioned at the inlet 42 as is shown in FIG. 7B. Thus, in FIG. 7B, vacuum source 130 and applicator region 40 are no longer in gaseous communication with each other, and the pressures within each may thus be different. As bodily fluid 30 continues to enter applicator region 40, however, the pressure within applicator region 40 may increase, since the existing gas within applicator region 40 is unable to exit via inlet 42 into fluid communication pathway 140. Thus, the pressure within applicator region 40 may increase relative to vacuum source 130, which may be used to facilitate the flow of bodily fluid 30 through inlet 42 into fluid communication pathway 140. In some embodiments, inlet 42 within applicator region 40 may be positioned to facilitate this process, for example, by positioning inlet 42 relatively close to the skin of the subject, as discussed herein. Of course, fluid may be introduced into the channel 140 without requiring equilibration of pressures between the applicator region 40 and the vacuum source, blocking of the inlet, etc. Instead, fluid communication between the vacuum source 130 and the application region 40 may be opened and drawn into the channel 140 via the inlet 42 in any suitable way and under any suitable conditions.

In certain aspects, the device includes a fluid transporter able to receive fluid from the skin. As used herein, "fluid transporter" is any component or combination of components that facilitates movement of a fluid from one portion of the device to another, and/or from the device to the skin of the subject or vice versa. For example, at or near the skin, a fluid transporter can be or include a hollow needle or a solid needle, or other flow activator, and/or include a volume (e.g, an applicator region) around a flow activator into which blood or other fluid flows. The flow activator may include a moveable mechanism, e.g., to move a needle, or may not require movement to function. For example, the flow activator may include a jet injector or a "hypospray" that delivers fluid under pressure to a subject, a pneumatic system that delivers and/or receives fluid, a hygroscopic agent that adsorbs or absorbs fluid, a reverse iontophoresis system, a transducer that emits ultrasonic waves, or thermal, radiofrequency and/or laser energy, and so on, any of which need not necessarily require movement of a flow activator to cause fluid release from a subject. If a solid needle is used, and fluid migrates along the needle due to surface forces (e.g., capillary action), then the solid needle can be at least a part of a fluid transporter. If fluid (e.g. blood or interstitial fluid) partially or fully fills an enclosure surrounding a needle after puncture of skin (whether the needle is or is not received from the skin after puncture), then the enclosure can define at least a part of the fluid transporter. In some embodiments, the fluid transporter may include an applicator region such as is described herein (with or without a needle or other flow activator therein). Other components including partially or fully enclosed channels, microfluidic channels, tubes, wicking members, vacuum containers, etc. can be included with a fluid transporter.

The fluid may be received from the skin of a subject (or other mucosal surface). The fluid transporter may include, for example, one or more needles and/or microneedles, a hygroscopic agent, a cutter or other piercing element, an electrically-assisted system, or the like, e.g., as discussed in detail herein. If needles or microneedles are used, they may be solid or hollow, i.e., blood, interstitial fluid, or other fluid may travel in and/or around the needles or microneedles into the device. In some cases, the needles or microneedles may also be removed from the skin of the subject, e.g., after insertion into the skin, for example, to increase the flow of blood or other fluids from the skin and/or beneath the skin of the subject. For example, one or more needles or microneedles may be inserted into the skin and removed, and then a vacuum or other pressure gradient may be applied to the skin to receive a fluid, such as blood or interstitial fluid. In one set of embodiments, the fluid transporter includes solid needles that are removed from the skin and a cup or channel may be used to direct the flow of blood or other bodily fluids.

Non-limiting examples of flow activators include one or more needles and/or microneedles, a hygroscopic agent, a cutter or other piercing element, an electrically-assisted system, or any other systems as described herein. Additional examples of such techniques are described herein and/or in the applications incorporated herein. It is to be understood that, generally, fluids may be received in a variety of ways, and various systems and methods for receiving fluid from the skin are discussed below and/or in the applications incorporated herein. In one set of embodiments, techniques for piercing or altering the surface of the skin to transport a fluid are discussed, for example, using a needle such as a hypodermic needle or one or more microneedles, chemicals applied to the skin (e.g., penetration enhancers), jet injectors or other techniques such as those discussed below.

As an example, in one embodiment, a needle such as a hypodermic needle can be used to receive fluid to or from the skin and/or beneath the skin. Hypodermic needles are well-known to those of ordinary skill in the art, and can be obtained commercially with a range of needle gauges. For example, the needle may be in the 20-30 gauge range, or the needle may be 32 gauge, 33 gauge, 34 gauge, etc.

If needles are present, there may be one or more needles, the needles may be of any suitable size and length, and the needles may each be solid or hollow. The needles may have any suitable cross-section (e.g., perpendicular to the direction of penetration), for example, circular, square, oval, elliptical, rectangular, rounded rectangle, triangular, polygonal, hexagonal, irregular, etc. For example, the needle may have a length of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, less than about 10 micrometers, etc. The needle may also have a largest cross-sectional dimension of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, less than about 10 micrometers, etc. For example, in one embodiment, the needle may have a rectangular cross section having dimensions of 175 micrometers by 50 micrometers. In one set of embodiments, the needle may have an aspect ratio of length to largest cross-sectional dimension of at least about 2:1, at least about 3:1, at least about 4:1, at least 5:1, at least about 7:1, at least about 10:1, at least about 15:1, at least about 20:1, at least about 25:1, at least about 30:1, etc.

In one embodiment, the needle is a microneedle. Typically, a microneedle will have an average cross-sectional dimension (e.g., diameter) of less than about a millimeter. It should be understood that references to "needle" or "microneedle" as discussed herein are by way of example and ease of presentation only, and that in other embodiments, more than one needle and/or microneedle may be present in any of the descriptions herein.

As an example, microneedles such as those disclosed in U.S. Pat. No. 6,334,856, issued Jan. 1, 2002, entitled "Microneedle Devices and Methods of Manufacture and Use Thereof," by Allen, et al., may be used to receive fluids (or other materials) from a subject. The microneedles may be hollow or solid, and may be formed from any suitable material, e.g., metals, ceramics, semiconductors, organics, polymers, and/or composites. Examples include, but are not limited to, medical grade stainless steel, titanium, nickel, iron, gold, tin, chromium, copper, alloys of these or other metals, silicon, silicon dioxide, and polymers, including polymers of hydroxy acids such as lactic acid and glycolic acid polylactide, polyglycolide, polylactide-co-glycolide, and copolymers with polyethylene glycol, polyanhydrides, polyorthoesters, polyurethanes, polybutyric acid, polyvaleric acid, polylactide-co-caprolactone, polycarbonate, polymethacrylic acid, polyethylenevinyl acetate, polytetrafluorethylene, polymethyl methacrylate, polyacrylic acid, or polyesters.

In some cases, more than one needle or microneedle may be used. For example, arrays of needles or microneedles may be used, and the needles or microneedles may be arranged in the array in any suitable configuration, e.g., periodic, random, etc. In some cases, the array may have 3 or more, 4 or more, 5 or more, 6 or more, 10 or more, 15 or more, 20 or more, 35 or more, 50 or more, 100 or more, or any other suitable number of needles or microneedles. In some embodiments, the device may have at least 3 but no more than 5 needles or microneedles (or other flow activators), at least 6 but no more than 10 needles or microneedles, or at least 11 but no more than 20 needles or microneedles. Typically, a microneedle will have an average cross-sectional dimension (e.g., diameter) of less than about a micron.

Those of ordinary skill in the art can arrange needles relative to the skin for these purposes including, in one embodiment, introducing needles into the skin at an angle, relative to the skin's surface, other than 90°, i.e., to introduce a needle or needles into the skin in a slanting fashion so as to limit the depth of penetration. In another embodiment, however, the needles may enter the skin at approximately 90°.

In some cases, the needles (or microneedles) may be present in an array selected such that the density of needles within the array is between about 0.5 needles/mm$^2$ and about 10 needles/mm$^2$, and in some cases, the density may be between about 0.6 needles/mm$^2$ and about 5 needles/mm$^2$, between about 0.8 needles/mm$^2$ and about 3 needles/mm$^2$, between about 1 needles/mm$^2$ and about 2.5 needles/mm$^2$, or the like. In some cases, the needles may be positioned within the array such that no two needles are closer than about 1 mm, about 0.9 mm, about 0.8 mm, about 0.7 mm, about 0.6 mm, about 0.5 mm, about 0.4 mm, about 0.3 mm, about 0.2 mm, about 0.1 mm, about 0.05 mm, about 0.03 mm, about 0.01 mm, etc.

In another set of embodiments, the needles (or microneedles) may be chosen such that the area of the needles (determined by determining the area of penetration or perforation on the surface of the skin of the subject by the needles) allows for adequate flow of fluid to or from the skin and/or beneath the skin of the subject. The needles may be chosen to have smaller or larger areas (or smaller or large diameters), so long as the area of contact for the needles to the skin is sufficient to allow adequate blood flow from the skin of the subject to the device. For example, in certain embodiments, the needles may be selected to have a combined skin-penetration area of at least about 500 nm$^2$, at least about 1,000 nm$^2$, at least about 3,000 nm$^2$, at least about 10,000 nm$^2$, at least about 30,000 nm$^2$, at least about 100,000 nm$^2$, at least about 300,000 nm$^2$, at least about 1 microns$^2$, at least about 3 microns$^2$, at least about 10 microns$^2$, at least about 30 microns$^2$, at least about 100 microns$^2$, at least about 300 microns$^2$, at least about 500 microns$^2$, at least about 1,000 microns$^2$, at least about 2,000 microns$^2$, at least about 2,500 microns$^2$, at least about 3,000 microns$^2$, at least about 5,000 microns$^2$, at least about 8,000 microns$^2$, at least about 10,000 microns$^2$, at least about 35,000 microns$^2$, at least about 100,000 microns$^2$, at least about 300,000 microns$^2$, at least about 500,000 microns$^2$, at least about 800,000 microns$^2$, at least about 8,000,000 microns$^2$, etc., depending on the application.

The needles or microneedles may have any suitable length, and the length may be, in some cases, dependent on the application. For example, needles designed to only penetrate the epidermis may be shorter than needles designed to also penetrate the dermis, or to extend beneath the dermis or the skin. In certain embodiments, the needles or microneedles may have a maximum penetration into the skin of no more than about 3 mm, no more than about 2 mm, no more than about 1.75 mm, no more than about 1.5 mm, no more than about 1.25 mm, no more than about 1 mm, no more than about 900 microns, no more than about 800 microns, no more than about 750 microns, no more than about 600 microns, no more than about 500 microns, no more than about 400 microns, no more than about 300 microns, no more than about 200 microns, no more than about 175 micrometers, no more than about 150 micrometers, no more than about 125 micrometers, no more than about 100 micrometers, no more than about 75 micrometers, no more than about 50 micrometers, etc. In certain embodiments, the needles or microneedles may be selected so as to have a maximum penetration into the skin of at least about 50 micrometers, at least about 100 micrometers, at least about 300 micrometers, at least about 500 micrometers, at least about 1 mm, at least about 2 mm, at least about 3 mm, etc.

In one set of embodiments, the needles (or microneedles) may be coated. For example, the needles may be coated with a substance that is delivered when the needles are inserted into the skin. For instance, the coating may comprise heparin, an anticoagulant, an anti-inflammatory compound, an analgesic, an anti-histamine compound, etc. to assist with the flow of blood from the skin of the subject, or the coating may comprise a drug or other therapeutic agent such as those described herein. The drug or other therapeutic agent may be one used for localized delivery (e.g., of or proximate the region to which the coated needles or microneedles are applied), and/or the drug or other therapeutic agent may be one intended for systemic delivery within the subject.

In one embodiment, the fluid is received manually, e.g., by manipulating a plunger on a syringe. In another embodiment, the fluid can be received from the skin and/or beneath the skin mechanically or automatically, e.g., using a piston pump or the like. Fluid may also be received using vacuums such as those discussed herein. For example, vacuum may be applied to a conduit, such as a needle, in fluidic communication with a bodily fluid in order to draw up at least a portion of the fluid from the skin. In yet another embodiment, fluid is received using capillary action (e.g., using a microfluidic channel or hypodermic needle having a suitably narrow inner diameter). In still another embodiment, pressure may be applied to force fluid out of the needle.

In some embodiments, fluid may be received using a hygroscopic agent applied to the surface of the skin or proximate the skin. For example, a device as described herein may contain a hygroscopic agent. In some cases, pressure may be applied to drive the hygroscopic agent into the skin. Hygroscopic agents typically are able to attract water from the surrounding environment, for instance, through absorption or adsorption. Non-limiting examples of hygroscopic agents include sugar, honey, glycerol, ethanol, methanol, sulfuric acid, methamphetamine, iodine, many chloride and hydroxide salts, and a variety of other substances. Other examples include, but are not limited to, zinc chloride, calcium chloride, potassium hydroxide, or sodium hydroxide. In some cases, a suitable hygroscopic agent may be chosen based on its physical or reactive properties, e.g., inertness or biocompatibility towards the skin of the subject, depending on the application.

In some embodiments, the device may comprise a cutter able to cut or pierce the surface of the skin. The cutter may comprise any mechanism able to create a path through which fluids may be received from the skin and/or beneath the skin. For example, the cutter may comprise a hypodermic needle, a blade (e.g., a knife blade, a serrated blade, etc.), a piercing element (e.g., a lancet or a solid or a hollow needle), or the like, which can be applied to the skin to create a suitable conduit for the receiving of fluid from the skin and/or from beneath the skin. In one embodiment, a cutter is used to create such a pathway and removed, and then fluid may be received via this pathway. In another embodiment, the cutter remains in place within the skin, and fluid may be received through a conduit within the cutter.

In some embodiments, fluid may be received using an electric charge. For example, reverse iontophoresis may be used. Without wishing to be bound by any theory, reverse iontophoresis uses a small electric current to drive charged and highly polar compounds across the skin. Since the skin is negatively charged at physiologic pH, it acts as a permselective membrane to cations, and the passage of counterions across the skin induces an electroosmotic solvent flow that may carry neutral molecules in the anode-to-cathode direction. Components in the solvent flow may be analyzed as described elsewhere herein. In some instances, a reverse iontophoresis apparatus may comprise an anode cell and a cathode cell, each in contact with the skin. The anode cell may be filled, for example, with an aqueous buffer solution (i.e., aqueous Tris buffer) having a pH greater than 4 and an electrolyte (i.e. sodium chloride). The cathode cell can be filled with aqueous buffer. As one example, a first electrode (e.g., an anode) can be inserted into the anode cell and a second electrode (e.g., a cathode) can be inserted in the cathode cell. In some embodiments, the electrodes are not in direct contact with the skin.

A current may be applied to induce reverse iontophoresis, thereby receiving a fluid from the skin. The current applied may be, for example, greater than 0.01 mA, greater than 0.3 mA, greater than 0.1 mA, greater than 0.3 mA, greater than 0.5 mA, or greater than 1 mA. It should be understood that currents outside these ranges may be used as well. The current may be applied for a set period of time. For example, the current may be applied for greater than 30 seconds, greater than 1 minute, greater than 5 minutes, greater than 30 minutes, greater than 1 hour, greater than 2 hours, or greater than 5 hours. It should be understood that times outside these ranges may be used as well.

In one set of embodiments, the flow activator may comprise an apparatus for ablating the skin. Without wishing to be bound by any theory, it is believed that ablation comprises removing a microscopic patch of stratum corneum (i.e., ablation forms a micropore), thus allowing access to bodily fluids. In some cases, thermal, radiofrequency, and/or laser energy may be used for ablation. In some instances, thermal ablation may be applied using a heating element. Radiofrequency ablation may be carried out using a frequency and energy capable of heating water and/or tissue. A laser may also be used to irradiate a location on the skin to remove a portion. In some embodiments, the heat may be applied in pulses such that a steep temperature gradient exists essentially perpendicular to the surface of the skin. For example, a temperature of at least 100° C., at least 200° C., at least 300° C., or at least 400° C. may be applied for less than 1 second, less than 0.1 seconds, less than 0.01 seconds, less than 0.005 seconds, or less than 0.001 seconds.

In some embodiments, the device may comprise a mechanism for taking a solid sample of tissue. For example, a solid tissue sample may be acquired by methods such as scraping the skin or cutting out a portion. Scraping may comprise a reciprocating action whereby an instrument is scraped along the surface of the skin in two or more directions. Scraping can also be accomplished by a rotating action, for example parallel to the surface of the skin and in one direction (i.e., with a roller drum) or parallel to the surface of the skin and in a circular manner (i.e., with a drilling instrument). A cutting mechanism may comprise a blade capable of making one or more incisions and a mechanism for removing a portion of tissue (i.e., by suction or mechanically picking up) or may use a pincer mechanism for cutting out a portion of tissue. A cutting mechanism may also function by a coring action. For example, a hollow cylindrical device can be penetrated into the skin such that a cylindrical core of tissue may be removed. A solid sample may be analyzed directly or may be liquefied prior to analysis. Liquefaction can comprise treatment with organic solvents, enzymatic solutions, surfactants, etc.

In certain embodiments, the flow activator may be fastened on a support structure. In some cases, the support structure can bring the flow activator to the skin, and in certain instances, insert the fluid transport into the skin. For example, the flow activator can be moved mechanically, electrically (e.g., with the aid of a servo, which may be computer-controlled), pneumatically, via a piston, a screw, a mechanical linkage, or the like. In one set of embodiments, the support structure can insert the flow activator into the skin at a speed of at least about 0.1 cm/s, at least about 0.3 cm/s, about 1 cm/s, at least about 3 cm/s, at least about 10 cm/s, at least about 30 cm/s, at least about 1 m/s, at least about 2 m/s, at least about 3 m/s, at least about 4 m/s, at least about 5 m/s, at least about 6 m/s, at least about 7 m/s, at least about 8 m/s, at least about 9 m/s, at least about 10 m/s, at least about 12 m/s, etc., at the point where the flow activator initially contacts the skin. Without wishing to be bound by any theory, it is believed that relatively faster insertion speeds may increase the ability of the flow activator to penetrate the skin (without deforming the skin or causing the skin to move in response), and/or decrease the amount of pain felt by the application of the flow activator to the skin. Any suitable method of controlling the penetration speed into the skin may be used, include those described herein.

Thus in some aspects, the device may include a support structure for application to the skin of the subject. The support structure may be used, as discussed herein, for applying the flow activator to the surface of the skin of the subject, e.g., so that fluid may be received from the skin and/or beneath the skin of the subject. In some cases, the support structure may immobilize the flow activator such that the flow activator cannot move relative to the support structure; in other cases, however, the flow activator may be able to move relative to the support structure. In one embodiment, as a non-limiting example, the flow activator is immobilized relative to the support structure, and the support structure is positioned within the device such that application of the device to the skin causes at least a portion of the flow activator to pierce the skin of the subject. In some cases, as discussed herein, the support structure includes a reversibly deformable structure.

In one set of embodiments, the support structure, or a portion of the support structure, may move from a first position to a second position. For example, the first position may be one where the support structure has immobilized relative thereto a flow activator that does not contact the skin (e.g., the flow activator may be contained within a recess), while the second position may be one where the flow activator does contact the skin, and in some cases, the flow activator may pierce the skin. The support structure may be moved using any suitable technique, e.g., manually, mechanically, electromagnetically, using a servo mechanism, or the like. In one set of embodiments, for example, the support structure may be moved from a first position to a second position by pushing a button on the device, which causes the support structure to move (either directly, or indirectly, e.g., through a mechanism linking the button with the support structure). Other mechanisms (e.g., dials, levers, sliders, etc., as discussed herein) may be used in conjunction with or instead of a button. In another set of embodiments, the support structure may be moved from a first position to a second position automatically, for example, upon activation by a computer, upon remote activation, after a period of time has elapsed, or the like. For example, in one embodiment, a servo connected to the support structure is activated electronically, moving the support structure from the first position to the second position.

In some cases, the support structure may also be moved from the second position to the first position. For example, after fluid has been received from the skin and/or beneath the skin, e.g., using a flow activator the support structure may be moved, which may move the flow activator away from contact with the skin. The support structure may be moved from the second position to the first position using any suitable technique, including those described above, and the technique for moving the support structure from the second position to the first position may be the same or different as that moving the support structure from the first position to the second position.

In one set of embodiments, the device may include a flexible concave member or a reversibly deformable structure that is moveable between a first configuration and a second configuration. For instance, the first configuration may have a concave shape, such as a dome shape, and the second configuration may have a different shape, for example, a deformed shape (e.g., a "squashed dome"), a convex shape, an inverted concave shape, or the like. The flexible concave member (or a reversibly deformable structure) may be moved between the first configuration and the second configuration manually, e.g., by pushing on the flexible concave member using a hand or a finger, and/or the flexible concave member may be moved using an actuator such as is described herein. In some cases, the flexible concave member may be able to spontaneously return from the second configuration back to the first configuration. In other cases, however, the flexible concave member may not be able to return to the first configuration, for instance, in order to prevent accidental repeated uses of the flexible concave member. The flexible concave member, in some embodiments, may be a reversibly deformable structure, although in other embodiments, it need not be.

The flexible concave member (or a reversibly deformable structure, in some embodiments) may be mechanically coupled to one or more needles (e.g., microneedles), or other flow activators such as those discussed herein. The needle may be directly immobilized on the flexible concave member, or the needles can be mechanically coupled to the flexible concave member using bars, rods, levers, plates, springs, or other suitable structures. The needle (or other flow activator), in some embodiments, is mechanically coupled to the flexible concave member such that the needle is in a first position when the flexible concave member is in a first configuration and the needle is in a second position when the flexible concave member is in a second configuration.

In some cases, relatively high speeds and/or accelerations may be achieved, and/or insertion of the needle may occur in a relatively short period of time, e.g., as is discussed herein. The first position and the second position, in some cases, may be separated by relatively small distances. For example, the first position and the second position may be separated by a distance of less than about 10 mm, less than about 9 mm, less than about 8 mm, less than about 7 mm, less than about 6 mm, less than about 5 mm, less than about 4 mm, less than about 3 mm, or less than about 2 mm, etc.

However, even within such distances, in certain embodiments, high speeds and/or accelerations such as those discussed herein can be achieved.

During use, a device may be placed into contact with the skin of a subject such that a recess or other suitable applicator region is proximate or in contact with the skin. By moving the flexible concave member (or reversibly deformable structure) between a first configuration and a second configuration, because of the mechanical coupling, the flexible concave member is able to cause a needle (or other flow activator) to move to a second position within the recess or other applicator region and to contact or penetrate the skin of the subject.

In some embodiments, the device may also include a retraction mechanism able to move the needle (or other flow activator) away from the skin after the flexible concave member (or a reversibly deformable structure) reaches a second configuration. Retraction of the flexible concave member may, in some embodiments, be caused by the flexible concave member itself, e.g., spontaneously returning from the second configuration back to the first configuration, and/or the device may include a separate retraction mechanism, for example, a spring, an elastic member, a collapsible foam, or the like.

In some cases, the support structure may be able to draw skin towards the fluid transporter. For example, in one set of embodiments, the support structure may include a vacuum interface or region. The interface or region may be connected with a vacuum source (external and/or internal to the device), and when a vacuum is applied, skin may be drawn towards the support structure, e.g., for contact with a flow activator, such as one or more needles or microneedles.

In some cases, the device includes an interface that is able to apply vacuum to the skin. The interface may be, for example, a suction cup or a circular bowl that is placed on the surface of the skin, and vacuum applied to the interface to create a vacuum. In one set of embodiments, the interface is part of a support structure, as discussed herein. The interface may be formed from any suitable material, e.g., glass, rubber, polymers such as silicone, polyurethane, nitrile rubber, EPDM rubber, neoprene, or the like. In some cases, the attachment between the interface and the skin may be enhanced (e.g., reducing leakage), for instance, using vacuum grease, petroleum jelly, a gel, or the like. In some cases, the interface may be relatively small, for example, having a diameter of less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm. The interface may be circular, although other shapes are also possible, for example, square, star-shaped (having 5, 6, 7, 8, 9, 10, 11, etc. points), tear-drop, oval, rectangular, or the like.

In some cases, the support structure may be able to draw skin towards the fluid transporter. For example, in one set of embodiments, the support structure may include a vacuum interface. The interface may be connected with a vacuum source (external and/or internal to the device), and when a vacuum is applied, skin may be drawn towards the support structure, e.g., for positioning in a recess of a fluid transporter and contact with a flow activator, such as with one or more needles or microneedles. The interface may also be selected, in some cases, to keep the size of the contact region below a certain area, e.g., to minimize pain or discomfort to the subject, for aesthetic reasons, or the like. The interface may be constructed out of any suitable material, e.g., glass, plastic, or the like.

In one set of embodiments, the device includes a reversibly deformable structure able to drive a flow activator or a substance transfer component into the skin, e.g., so that the flow activator can receive a fluid from the skin and/or from beneath the skin of a subject. The reversibly deformable structure may be a structure that can be deformed using unaided force (e.g., by a human pushing the structure), or other forces (e.g., electrically-applied forces, mechanical interactions or the like), but is able to restore its original shape after the force is removed or at least partially reduced. For example, the structure may restore its original shape spontaneously, or some action (e.g., heating) may be needed to restore the structure to its original shape.

The reversibly deformable structure may be formed out a suitable elastic material, in some cases. For instance, the structure may be formed from a plastic, a polymer, a metal, etc. In one set of embodiments, the structure may have a concave or convex shape. For instance, the edges of the structure may be put under compressive stress such that the structure "bows" out to form a concave or convex shape. A person pushing against the concave or convex shape may deform the structure, but after the person stops pushing on the structure, the structure may be able to return to its original concave or convex shape, e.g., spontaneously or with the aid of other forces as previously discussed. In some cases, the device may be bistable, i.e., having two different positions in which the device is stable.

Figure 12:
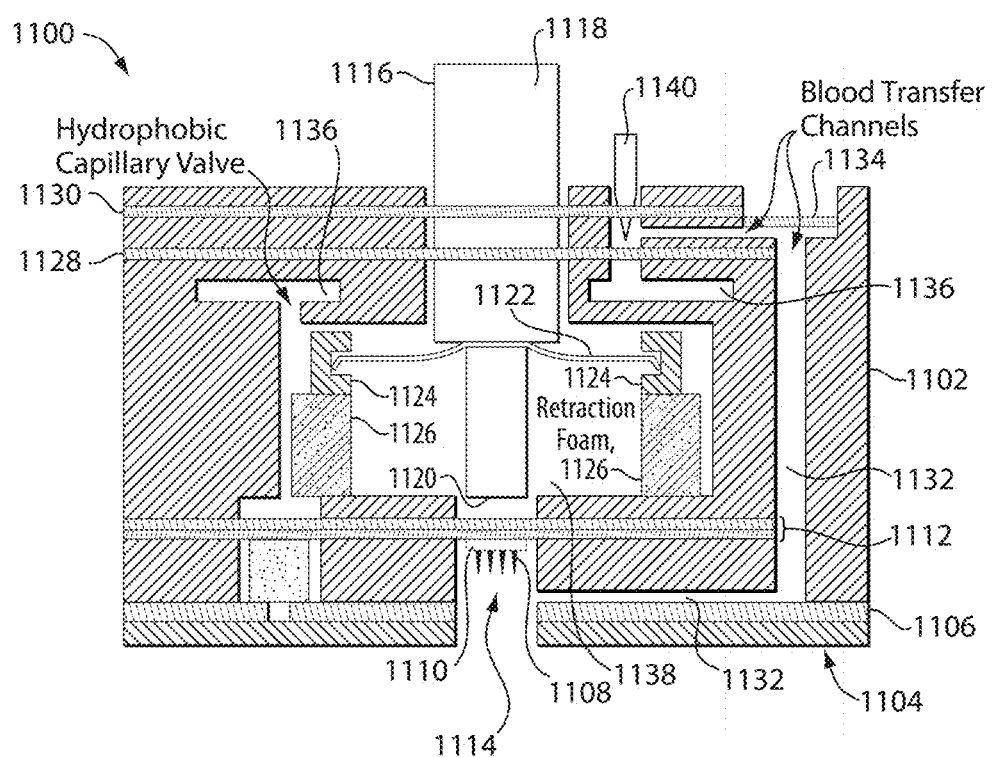
FIG. 12 illustrates yet another embodiment of the invention in which a device is actuated by a reversibly deformable structure.

An example of a reversibly deformable structure is now illustrated with respect to FIG. 12, which schematically illustrates device 1100 in which a flow activator comprising a substance transfer component is driven by a reversibly deformable structure. In FIG. 12, device 1100 includes a housing 1102 defining a plurality of chambers and channels. In other embodiments (not shown) a plurality of components that can be separable from and attachable to each other (e.g., modular components) can together define the device and together define a series of channels and compartments necessary for device function. See, e.g., U.S. patent application Ser. No. 12/716,233, filed Mar. 2, 2010, entitled "Systems and Methods for Creating and Using Suction Blisters or Other Pooled Regions of Fluid within the Skin," by Levinson, et al.; U.S. patent application Ser. No. 12/716,226, filed Mar. 2, 2010, entitled "Techniques and Devices Associated with Blood Sampling," by Levinson, et al.; U.S. patent application Ser. No. 12/716,229, filed Mar. 2, 2010, entitled "Devices and Techniques Associated with Diagnostics, Therapies, and Other Applications, Including Skin-Associated Applications," by Bernstein, et al.; or U.S. Provisional Patent Application Ser. No. 61/411,566, filed Nov. 9, 2010, entitled "Systems and Interfaces for Blood Sampling," by David Brancazio, each incorporated herein by reference.

In the specific device illustrated, device 1100 includes a surface 1104 for positioning the device proximate the skin of a subject during use. Where desired in certain embodiments, the device can include an adhesive layer 1106 where the adhesive is selected to be suitable for retaining the device in a relatively fixed position relative to the skin during use, but may allow for relatively easy removal of the device from the skin following use. Specific non-limiting examples of adhesives are discussed below. The adhesive also can be selected to assist in maintaining a vacuum within portions of the device proximate the skin as will be understood.

In FIG. 12, device 1100 includes a substance transfer component 1108. The substance transfer component may be, for example, a flow activator and/or a skin insertion object as discussed herein. Specific non-limiting examples include one or more needles or microneedles, e.g., as shown in FIG. 12. The substance transfer component can be, as described elsewhere herein and in other documents incorporated herein by reference, any of a variety of components able to receive a substance from the skin and/or from beneath the skin of a subject. For example, the substance transfer component may include one or more needles and/or microneedles, a hygroscopic agent, a cutter or other piercing element, an electrically-assisted system, or the like. In the specific device illustrated, substance transfer component 1108 defines an array of microinsertion objects such as solid or hollow microneedles. In one set of embodiments, substance transfer component 1108 is selected to have a particular size and profile for a particular use. For example, the substance transfer component may include an array of insertion or microinsertion objects which, in the device illustrated, emanate from a base 1110 which will be described further below.

In certain embodiments, a plurality of skin insertion objects define substance transfer component 1108 and are relatively small, and are relatively completely driven into the skin. Examples of skin insertion objects include needles or microneedles, e.g., as described in greater detail below. The skin insertion objects may be positioned to address the skin of the subject, each protruding from a base and defining a length from the base, and are able to be inserted into or through the skin to a depth essentially equal to their length but are prevented, by the base, from inserting at a depth greater than their length. In some embodiments, the plurality of skin insertion objects have an average length (measured from the base) of no more than about 1,000 microns or more than about 2,000 microns, although lengths can differ between individual skin insertion objects. In one set of embodiments, the skin insertion objects are of relatively uniform length, together defining an average length and each differing from the average length by no more than about 50%, about 40%, about 30%, about 10%, or about 5%, e.g., relative to the average length. The average length of the skin insertion objects, in other embodiments, are no more than about 1,500 microns, no more than about 1,000 microns, no more than about 900 microns, no more than about 800 microns, no more than about 750 microns, no more than about 600 microns, no more than about 500 microns, no more than about 400 microns, or no more than about 350 microns. In some embodiments, a triggering mechanism as discussed herein is provided that is able to move the skin insertion objects from a fully predeployed position to a fully deployed position with a force sufficient to insert the plurality of skin insertion object into or through the skin to an average depth of at least about 50% the average length of the plurality of skin insertion objects. In other embodiments, the triggering mechanism is able to insert the plurality of skin insertion objects to an average depth of at least about 55%, at least about 60%, at least about 65%, at least about 70%, at least about 75%, at least about 80%, at least about 85%, at least about 90%, at least about 92%, about 94%, about 96%, or about 98% of the average length of the plurality of skin insertion objects.

In the device illustrated, substance transfer component 1108 is mounted on a flexible structure 1112 which, as illustrated, is maintained relatively rigidly through various aspects of the device but which mounts substance transfer component 1108 flexibly for up/down movement relative to the skin. Flexible structure 1112 can be a membrane, a single or multi-layer structure selected from various polymers or the like to provide sufficient properties such as any combination of flexibility, elasticity, gas permeability or impermeability, fluid permeability or impermeability, or the like for desired operation. Portions of flexible structure 1112, substance transfer component 1108, and other interior walls of the device define a region 1114 which allows for movement of substance transfer component 1108 relative to the skin for the receiving of a substance from the skin or beneath the skin, and, where a substance is received from the skin or from beneath the skin, region 1114 can serve as a reservoir for introduction of the substance into the device. Where a vacuum is used to receive a substance from the subject (e.g., as in the embodiment illustrated in FIG. 12), region 1114, when positioned against the skin, can expose vacuum to that portion of the skin proximate surface 1104 of the device and abutting the chamber.

Device 1100 also includes a transfer component actuator 1116 which, as illustrated, includes a proximate portion 1118 which can be addressed by a user of the device (who may be the same or different from the subject the device is administered to) and a distal portion 1120 for addressing substance transfer component 1108 via flexible structure 1112. Proximal portion 1118 and distal portion 1120 are, in the device illustrated, opposite ends of a single component but, as would be understood by those of ordinary skill in the art, the actuator can include a plurality of individual components operably linked in any way necessary to perform actuation as will be described.

As will be understood, FIG. 12 is a cross-section of a device illustrating various components and channels within the device. As will also be understood by those of ordinary skill in the art, different arrangements of devices and channels are contemplated herein so long as the purpose of the device described herein is met. In this figure, actuator 1116 is directly connected to or otherwise operably linked to a reversibly deformable structure 1122 which, in the device illustrated, is in the form of a "snap dome," the function and use of which will be described below. The snap dome in this figure has an approximately circular profile. The structure may define an interior and a periphery which, if not circular, may include a plurality of tabs, protrusions, or the like sufficient for support of structure 1122 within the device. As illustrated, a plurality of tabs (or the essentially circular perimeter of) the device are supported within holders 1124, and the center, snap dome portion of the device is operably linked to actuator 1116, such that movement of the central portion of snap dome 1122 and the periphery of the snap dome can be controlled independently of each other. Holders 1124 are directly connected to or otherwise operably linked to an actuator retraction component 1126 which, in the device illustrated, can be a ring-shaped structure positioned under and supporting holders 1124. Holders 1124 can be individual holders and/or a ring-like structure surrounding the periphery of snap dome 1122. A series of one, two, or more support members (e.g., 1130) are positioned near the top of device 1100 and serve to define a series of channels for sample flow, vacuum control, or the like as will be described.

Turning now to channels defined within the device, as described above, region 1114, when the device is positioned against skin, can serve to expose a portion of the skin defined by the periphery of the region to a vacuum, to substance transfer component 1108 as it moves toward and/or away from the skin, and/or to transfer a substance from or to the subject. Region 1114 can house a substance for transfer to the subject, in the form of a pharmaceutical composition or the like, optionally loaded on substance transfer component 1108. Where blood and/or interstitial fluid is drawn from a subject, region 1114 can serve to introduce the substance into the device from the subject.

A channel 1132 connects region 1114 to other portions of the device in this example. Channel 1132 can be used to deliver a substance to region 1114 for transfer to a subject, or for application of a vacuum to region 1114, and/or for the receiving of a substance from a subject. The remainder of the description of device 1100 will be made within the context of receiving a substance such as blood and/or interstitial fluid from a subject, but it is to be understood that substances can also be delivered via various channels. Channel 1132 typically emanates in one direction from region 1114 although a plurality of channels can emanate from the region, arranged radially or otherwise relative to the center of the device. In device 1100, channel 1132 first passes laterally from the center of the device and then upwardly where, near the top of the device, it can, optionally, include one wall defining a window 1134 through which a user of the device can observe transfer of a substance, or through which analysis of a substance may occur. It can also itself define a reservoir, in whole or in part, or be connected to an internal or an external reservoir for maintaining, storing, and/or transferring a substance drawn from a subject. As shown here, it can be connected to a substance collection reservoir 1136 which, as illustrated, is a disc-shaped reservoir formed in the device housing and surrounding the center of the device including actuator 1116 and related components.

Device 1100, illustrated as one example of devices provided by the invention, includes a vacuum source for applying a vacuum proximate the skin of a subject for receiving a substance from the skin. As illustrated, vacuum source 1138 is positioned in a central portion of the device surrounding actuator 1116, although it can be provided anywhere in or proximate the device. The vacuum source can be evacuated to an appropriate level just prior to use, or the device can be pre-packaged under vacuum as described elsewhere herein. As illustrated, vacuum source 1138 is in fluid communication with substance collection reservoir 1136 but, in its initial state and prior to use, a membrane or other component, such as support member 1128, separates channel 1132 connecting it to region 1102. In the device illustrated, a vacuum actuation component 1140 can be actuated to puncture the membrane or other component (e.g., 1128) and thereby connect vacuum source 1138 with channel 1132, at an appropriate time during use of the device. In other embodiments, actuator 1116 and vacuum actuation component 1140 can be combined into a single button or operably linked so that only one operation is needed to actuate both the microinsertion objects and the vacuum.

Reversibly deformable structure (or, as shown, a snap dome) 1122 can be provided in a variety of forms including a monostable or bistable configuration. In the embodiment illustrated, a bistable configuration is illustrated including first and second low energy or stable configurations separated by a relatively high energy or unstable configuration. As shown, the reversibly deformable structure 1122 is shown in a "cocked" or predeployed position.

The reversibly deformable structure (or the flexible concave member) may be formed from any suitable material, for example, a metal such as stainless steel (e.g., 301, 301LN, 304, 304L, 304LN, 304H, 305, 312, 321, 321H, 316, 316L, 316LN, 316Ti, 317L, 409, 410, 430, 440A, 440B, 440C, 440F, 904L), carbon steel, spring steel, spring brass, phosphor bronze, beryllium copper, titanium, titanium alloy steels, chrome vanadium, nickel alloy steels (e.g., Monel 400, Monel K 500, Inconel 600, Inconel 718, Inconel x 750, etc.), a polymer (e.g., polyvinylchloride, polypropylene, polycarbonate, etc.), a composite or a laminate (e.g., comprising fiberglass, carbon fiber, bamboo, Kevlar, etc.), or the like.

The reversibly deformable structure may be of any shape and/or size. In one embodiment, the reversibly deformable structure is a flexible concave member. In some cases, the reversibly deformable structure may have a generally domed shape (e.g., as in a snap dome), and be circular (no legs), or the reversibly deformable structure may have other shapes, e.g., oblong, triangular (3 legs), square (4 legs), pentagonal (5 legs), hexagonal (6 legs), spider-legged, star-like, clover-shaped (with any number of lobes, e.g., 2, 3, 4, 5, etc.), or the like. The reversibly deformable structure may have, in some embodiments, a hole, dimple, or button in the middle. The reversibly deformable structure may also have a serrated disc or a wave shape. In some cases, a flow activator or a substance transfer component may be mounted on the reversibly deformable structure. In other cases, however, the flow activator or substance transfer component is mounted on a separate structure which is driven or actuated upon movement of the reversibly deformable structure.

In one set of embodiments, the reversibly deformable structure is not planar, and has a portion that can be in a first position (a "cocked" or predeployed position) or a second position (a "fired" or deployed position), optionally separated by a relatively high energy configuration. In some cases, both the first position and the second position are stable (i.e., the structure is bistable), although conversion between the first position and the second position requires the structure to proceed through an unstable configuration.

In some cases, surprisingly, the distance or separation between the first position and the second position is relatively small. Such distances or separations may be achieved using snap domes or other configurations such as those described herein, in contrast to springs or other devices which require longer translational or other movements. For example, the perpendicular distance (i.e., in a direction away from the skin) in the reversibly deformable structure between the top of the structure and the bottom of the structure (excluding the substance transfer component) when the device containing the structure is placed on the skin of a subject (i.e., the height of the device once it has been placed no the skin of the subject) may be no more than about 5 mm, no more than about 4 mm, no more than about 3 mm, no more than about 2 mm, no more than about 1 mm in some cases, no more than about 0.8 mm, no more than about 0.5 mm, or no more than about 0.3 mm. In one set of embodiments, the distance is between about 0.3 mm and about 1.5 mm. In another set of embodiments, the reversibly deformable structure may have a greatest lateral dimension (parallel to the skin) when the device containing the structure is placed on the skin of a subject of no more than about 50 mm, no more than about 40 mm, no more than about 30 mm, no more than about 25 mm, no more than about 20 mm, no more than about 15 mm, no more than about 5 mm, no more than about 4 mm, no more than about 3 mm, no more than about 2 mm, no more than about 1 mm in some cases, no more than about 0.8 mm, no more than about 0.5 mm, or no more than about 0.3 mm. In one set of embodiments, the distance is between about 0.3 mm and about 1.5 mm.

In some embodiments, the device may exhibit a relatively high success rate of the receiving of fluid from various subjects. For example, in some embodiments, the success rate of receiving at least about 5 microliters of blood from a subject may be at least about 95%, at least about 97%, at least about 98%, at least about 99%, or at least about 100%, as compared to prior art devices (e.g., lancet devices) which typically have success rates of less than 95%. In other embodiments, the volume may be at least about 0.1 microliters, at least about 0.3 microliters, at least about 0.5 microliters, at least about 1 microliter, at least about 3 microliters, at least about 5 microliters, or at least about 10 microliters. For instance, a population of subjects may be tested with both a prior art device and a device of the invention such that each subject is tested with both devices in a suitable location (e.g., the forearm) when determining success probabilities, where the population of subjects is randomly chosen. The population may be for example, at least 10, at least 100, at least 1,000, at least 10,000 or more individuals.

Use of device 1100 will now be described in the context of receiving a substance such as blood from a subject. Device 1100 is placed against the skin of a subject such that at least a portion of surface 1104 contacts the skin. Prior to use, a cover member (not shown) can cover surface 1104 of the device and can cover region 1114, to protect surface 1104 and region 1114 from contaminants, etc. optionally maintaining the interior of the device in a sterile condition. The cover can be peeled off or otherwise removed from the device, and the device placed against the skin, optionally adhering to the skin. Vacuum actuation component 1140 can be actuated to expose channel 1132 and region 1114 to vacuum at any time, including before, simultaneously, or after actuation of substance transfer component 1108. In one arrangement, vacuum actuation component 1140 is actuated to apply vacuum to region 1114 prior to actuation to substance transfer component 1108, thereby to create a vacuum against the skin proximate region 1114 prior to use. Actuation of actuator 1116 can take place before or after deployment of vacuum.

When transfer component actuator 1116 is actuated by a user (e.g., when proximal portion 1118 is depressed downwardly as shown in the figure), distal portion 1120 engages substance transfer component 1108 (optionally via flexible structure 1112) to drive it toward the skin. In some embodiments, foil 1128 is first broken, then component 1126 is compressed, before flexible structure 1112 is stretched and the reversibly deformable structure 1122 of the device fires or is actuated. Membranes or other members 1112, 1128, or 1130 may have, in some cases, sufficient flexibility and/or elasticity to allow actuator 1116 to drive substance transfer component 1108 sufficiently distally (downwardly, as shown) to engage the skin of the subject and carry out the desired function of the device. Various gaskets, bearings, or membranes as shown can be used for this function. Where support member 1128 is a foil or the like used for the purpose of initially separating vacuum reservoir 1138 from channel 1132 (e.g., prior to use), when actuator 1116 is moved downwardly, vacuum actuation component 1140 may rupture support member 1128 proximate actuator 1116, or flexibly deform as need be, so long as member 1130 (or another component) serves to allow actuator 1116 to slide within the device while maintaining sufficient vacuum in vacuum reservoir 1138 and related channels for use of the device.

When substance transfer component 1108 (e.g., insertion objects) engages the skin of the subject and facilitates the receiving of a substance from the skin and/or from beneath the skin of the subject, a vacuum can draw the substance into region 1114, through channel or channels 1132, and into substance collection reservoir 1136. In this process, actuator 1116 first urges structure 1122 from its first stable configuration to a relatively unstable configuration and beyond that point, at which point the structure 1122 rapidly moves to a second stable configuration associated with downward driving of actuator 1116 to quickly drive access substance transfer component 1108 into and/or through the skin.

After that point, if it is desirable for access substance transfer component 1108 to be withdrawn from the skin, then a variety of techniques can be used to do so. In the device illustrated, retraction component 1126 drives holder 1124 upwardly, retracting structure 1122 and actuator 1116 from substance transfer component 1108. At that point, actuator 1116 can be operably linked to transfer component 1108 and withdraw the transfer component, or it can move freely relative to substance transfer component 1108, whereby flexible structure 1112 (e.g., an elastic membrane) or other component can withdraw substance transfer component 1108 from the skin. Again, in the device illustrated, retraction component 1126 can itself be a reversibly deformable structure such as a leaf spring, coil spring, foam, or the like. During use, when actuator 1116 is driven downwardly, retraction component 1126 is first compressed and, depending upon the size and arrangement of components 1126, 1124, 1122, 1116 and 1108, during compression, substance transfer component 1108 can be driven downwardly to some extent. At the point at which retraction component 1126 is compressed and provides a sufficient resistance force, reversibly deformable structure 1122 can be urged from its first configuration through an unstable configuration and can return to its second configuration, driving substance transfer component 1108 against the skin. Then, upon release of user pressure (or other actuation, which can be automatic) from actuator 1116, retraction component 1126 can expand and, with structure 1122 optionally remaining in its second, downwardly-driven low-energy configuration, actuator 1116 can be retracted and substance transfer component 1108 retracted from the skin.

Figure 13A:
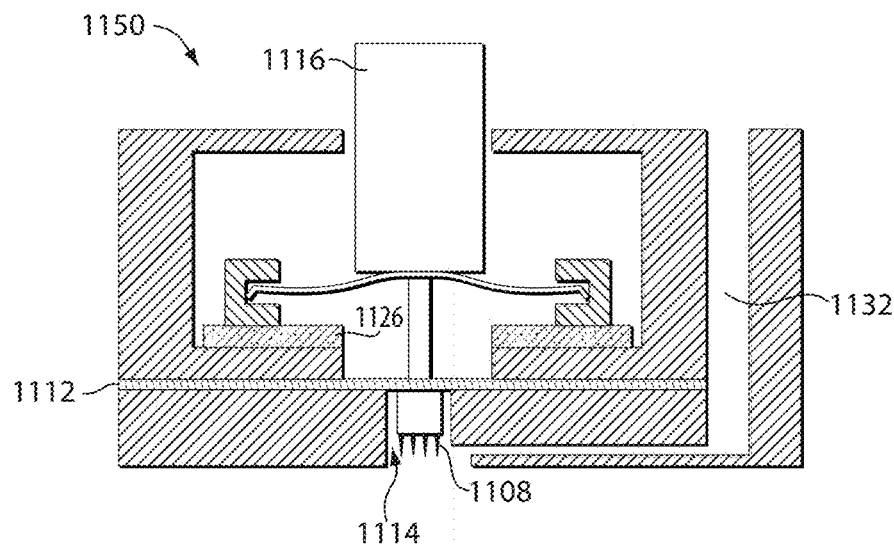
FIGS. 13A and 13B illustrate yet another embodiment of the invention, in which a device is actuated by a reversibly deformable structure, at different stages of operation of the device.
Figure 13B:
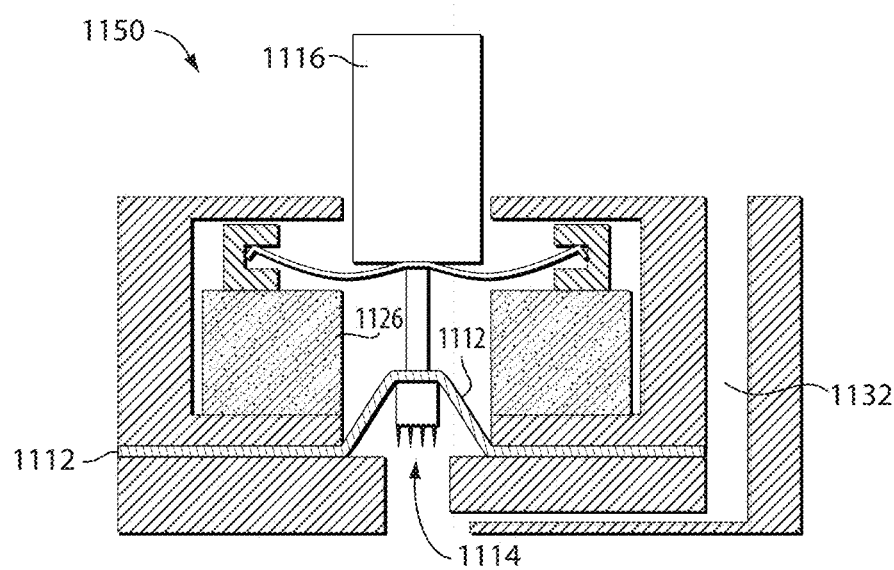

Referring now to FIGS. 13A and 13B, device 1150 is illustrated schematically. Device 1150 is similar to and can be considered essentially identical to device 1100 in all aspects other than those described here with respect to FIGS. 13A and 13B. As such, the reader will observe that not all components are provided, although other components similar to those of device 1100 can exist. One way in which device 1150 differs from device 1100 is that in device 1150, in the pre-deployment or post-deployment retracted configuration, membrane 1112 is drawn proximally (upwardly) as illustrated in FIG. 13B. Membrane 1112 is in a less-stressed lower-energy configuration as shown in FIG. 13A when retraction component 1126 is compressed and substance transfer component 1108 is driven into and/or through the skin. Devices 1100, 1150, and other similar devices are one way to enact a triggering mechanism that can move a substance transfer component 1108 or other similar transfer component relative to the skin in particularly advantageous ways. Examples of triggering mechanisms include, in addition to the examples shown in FIGS. 12 and 13, blasting caps, explosives, other chemical reactions, solenoids or other electrical interactions, pneumatics (e.g., compressed air), other thermal interactions or mechanical interactions, or the like.

In one set of embodiments, the triggering mechanism may move transfer component 1108 from a fully predeployed position (e.g., as shown in FIG. 12) to a fully deployed position in which substance transfer component 1108 is fully engaged with the skin, in a short period of time. In one embodiment, that period of time is less than about 0.01 seconds, and in other embodiments, less than about 0.009 seconds, less than about 0.008 seconds, less than about 0.007 seconds, less than about 0.006 seconds, less than about 0.005 seconds, less than about 0.004 seconds, less than about 0.003 seconds, less than about 0.002 seconds, less than about 0.001 seconds, less than about 0.0005 seconds, less than about 0.00025, or less than about 0.0001 seconds.

In another embodiment, substance transfer component 1108 moves quickly relative to skin during deployment via the triggering mechanism, reaching a speed of at least about 4 m/s, at least about 5 m/s, at least about 6 m/s, at least about 7 m/s, at least about 8 m/s, at least about 10 m/s, at least about 12 m/s, at least about 15 m/s, or at least about 20 m/s at the point at which substance transfer component 1108 first touches the skin during deployment.

In some cases, substance transfer component 1108 achieves relatively high accelerations due to the triggering mechanism, for example, at least about 4 m/s$^2$, about 6 m/s$^2$, about 8 m/s$^2$, about 10 m/s$^2$, about 12 m/s$^2$, about 15 m/s$^2$, or about 20 m/s$^2$, at least about 30 m/s$^2$, at least about 50 m/s$^2$, at least about 100 m/s$^2$, at least about 300 m/s$^2$, at least about 500 m/s$^2$, at least about 1,000 m/s$^2$, at least about 3,000 m/s$^2$, at least about 5,000 m/s$^2$, at least about 10,000 m/s$^2$, at least about 30,000 m/s$^2$, at least about 50,000 m/s$^2$, at least about 100,000 m/s$^2$, at least about 200,000 m/s$^2$, or at least about 300,000 m/s$^2$. In some embodiments, the substance transfer component 1108 is accelerated for relatively short periods of time, e.g., less than about 1 s, less than about 300 ms, less than about 100 ms, less than about 30 ms, less than about 10 ms, less than about 3 ms, or less than about 1 ms, and/or over relatively short distances, e.g., less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 100 micrometers, less than about 50 micrometers, etc.

Significant forces can be applied to substance transfer component 1108 as it moves relative to the skin via the triggering mechanism. In one set of embodiments, substance transfer component 1108, at the point at which it first contacts the skin, is driven by a force created at least in part by the triggering mechanism of at least about 6 micronewtons, about 8 micronewtons, about 10 micronewtons, about 12 micronewtons, or about 15 micronewtons.

In another set of embodiments, substance transfer component 1108 applies a pressure to the skin, during deployment caused by the triggering mechanism, of at least about 100 N/m$^2$, at least about 300 N/m$^2$, at least about 1,000 N/m$^2$, at least about 3,000 N/m$^2$, etc. In force assessment, the area can be measured as the area of skin displaced by the transfer component at full deployment, e.g., the area of the skin ruptured by the total of the cross sectional area of all substance transfer components inserted into the skin, at the top surface of the skin.

In some cases, the substance transfer component is forced into the skin via the triggering mechanism with a force sufficient to insert the substance transfer component into or through the skin to an average depth of at least about 60% of the substance transfer component (or the average length of the substance transfer components, if more than one is used, e.g., as in an array of needles or microneedles). In some cases, the depth is at least about 65%, at least about 70%, at least about 75%, at least about 80%, at least about 85%, at least about 90%, or at least about 95% of the substance transfer component, e.g., the length of the needle or the microneedle inserted into the skin.

Devices of the invention can provide significant advantage in some embodiments. For example, triggering mechanisms able to move substance transfer components in short time periods, and/or at high velocities, and/or with high forces, and/or with high pressure, and/or drive relatively short substance transfer components such as microinsertion objects or microneedles relatively deeply into the skin and/or through the skin, and/or any combination of the above can provide significant advantage. In some embodiments, these features can provide better control of substance delivery or receipt. Better mechanical stability can be provided in some cases by shorter substance transfer components (e.g., bending and/or buckling can be avoided) and relatively shorter substance transfer components, designed to be driven relatively completely (for example, through nearly all of their entire length) into the skin may offer better control of penetration in some embodiments. If better control of penetration can be achieved, better delivery or receipt can also be achieved in some cases, for example, resulting in less pain or essentially painless deployment.

Moreover, if substance transfer components are used to deliver a substance such as a pharmaceutical composition into or through the skin, more precise delivery can be provided, according to certain embodiments. More precise control over depth of insertion of the substance transfer components (e.g., by using devices designed to insert the substance transfer components essentially fully) yield more control over the amount of pharmaceutical substance inserted into the skin by the substance transfer components, in some embodiments. Furthermore, quick and/or high velocity, and/or high force and/or pressure application of microinsertion objects to the skin may in certain embodiments result in lower pain or painless deployment.

Figure 14A:
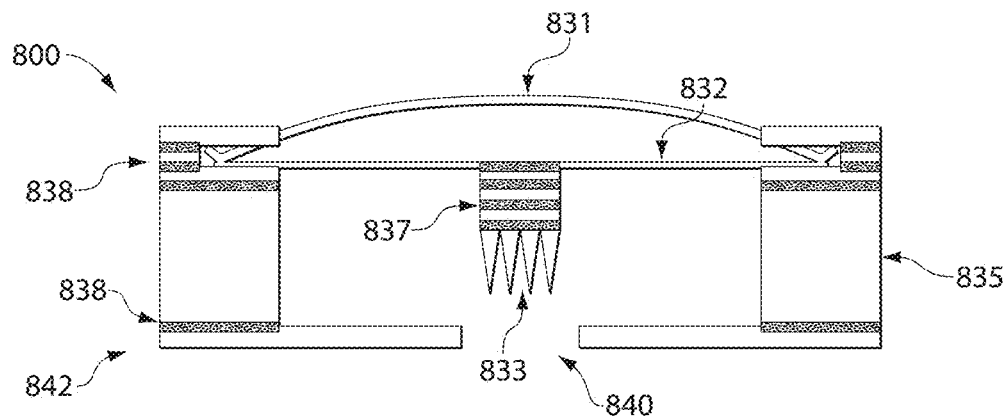
FIGS. 14A-14C illustrate various devices according to various embodiments of the invention.

Another example is illustrates in FIG. 14A. This figure shows a device 800 including a flow activator (e.g., microneedle array 833), a reversibly deformable structure (e.g., snap dome 832), an activator (e.g., activation button 831), a retraction mechanism (e.g., silicone foam 835), and structural components constructed from multiple layers of polycarbonate bonded together using a double-sided adhesive, such as 3M 1509 or 3M 1513 tape. The microneedle arrays can be bonded to laminated post 837 on the underside of a snap dome. Structural components 838, as well as post 837, are formed from polycarbonate and 3M 1509 or 3M 1513 adhesive. The arrays may range in needle number (4 to 28 needles), needle length (350 to 1000 micrometers), and/or arrangement (square, rectangular, and circular arrays), with array footprints of less than 3 mm in diameter, where the "footprint" is the area of the base to which the needles are attached.

In use, the device may be charged by setting the snap dome in a high energy position, placing the base of the device against the skin of a subject (with the needle tips pointing towards the skin), and pushing button 831 on the top of the device. As the button is pressed, silicone foam 835 compresses, positioning the needle tips in close proximity to the skin through opening 840. When the foam is fully compressed, the force causes the button to collapse, which then translates to the back of the snap dome to cause it to move to a stable low energy state. The release of energy from the snap dome changing states accelerates the microneedle array forward through the opening in the base and inserts the needles into the skin. When the force on the button is released, the silicone foam expands to its original height and retracts the needles from the skin in the process.

Figure 14B:
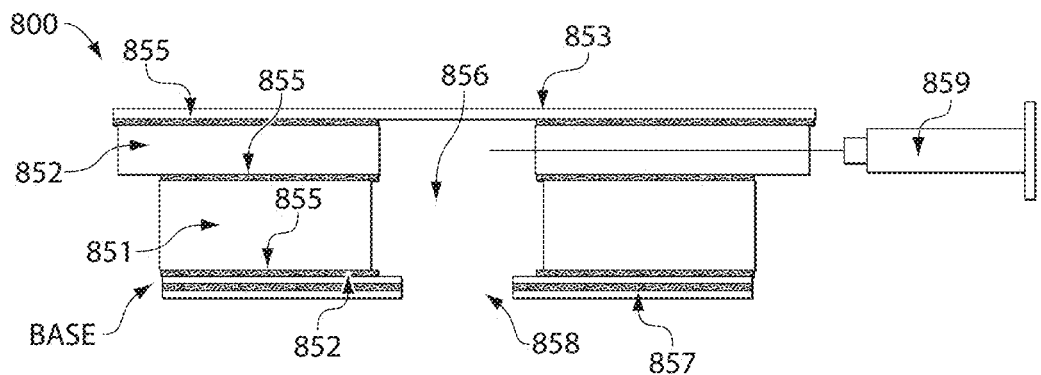

Yet another example is illustrates in FIG. 14B. This device includes a vacuum source comprising layers of polycarbonate, polyethylene terephthalate glycol (PETG), and silicone bonded together using a double-sided adhesive, such as 3M 1509 or 3M 1513 tape. The chamber is approximately 2.7 cm in diameter and 0.6 cm high, with cup opening 858 in the base that ranges from 3 to 7 mm in diameter. The vacuum source may be attached to the skin of a subject over the microneedle insertion site using adhesive 857, such as 3M 1509 or Katecho 10G hydrogel. A vacuum source (i.e., vacuum pump, syringe, vacuum reservoir, etc.) can be connected to the chamber using hypodermic needle 859 inserted through silicone layer 852, and vacuum (i.e., 30 to 70 kPa) may be applied to the site for a fixed period of time (i.e., 10 s to 10 min). The application of vacuum causes blood to flow from the skin punctures into the vacuum source.

Figure 14C:
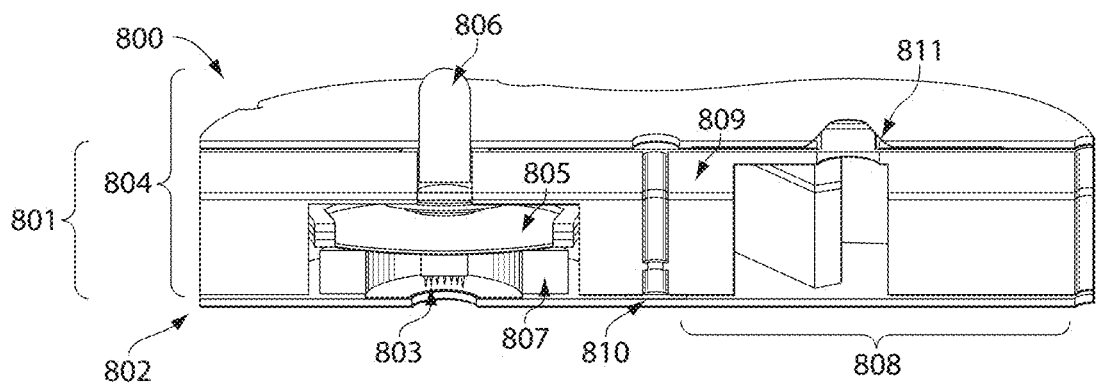

Still another example is shown in FIG. 14C. In this figure, the integrated device 800 includes a support structure 801 for application to the skin of the subject. The structure is constructed from multiple layers of polyethylene terephthalate glycol (PETG). These layers may be formed into the requisite geometry by machining sheet stock or injection molding. The individual layers are bonded together using double-sided adhesive, such as 3M 1513 tape, but may also be bonded using non-adhesive methods such as ultrasonic welding or laser welding. The support structure is attached to the skin of a subject using an adhesive 802, such as Katecho 10G hydrogel.

The left side of the support structure in FIG. 14C houses the components necessary to insert a microneedle array into the skin. These components include a circular microneedle array of sixteen 750 micrometers long needles 803 actuated by the extraction activator 804 comprising a reversibly deformable structure (e.g., a snap dome 805), a button 806, and a foam return mechanism 807. Pressing the button initially compresses the foam, bringing the microneedles into close proximity with the skin, and then fires the snap dome, moving it from the first stable configuration to the second stable configuration. The movement of the snap dome accelerates and inserts the microneedles into the skin. Releasing the pressure on the button allows the foam to expand and retract the microneedles from the skin.

The right side of the support structure shown in FIG. 14C comprises a self-contained vacuum source 808 fluidically connected to a storage chamber 809. The storage chamber is fluidically connected to the extraction activator by a microfluidic channel 810. Pressing the button 811 breaks a seal and causes the fluidically connected components to be evacuated as well as reduces the pressure on the skin below the microneedle array. This reduced pressure urges blood from the skin into the microfluidic channel and into the storage chamber.

In certain aspects, the device may also contain an activator. The activator may be constructed and arranged to cause exposure of the flow activator to the skin upon activation of the activator. For example, the activator may cause a chemical to be released to contact the skin, one or more needles or microneedles to be driven into the skin, a vacuum to be applied to the skin, a jet of fluid to be directed to the skin, or the like. The activator may be activated by the subject, and/or by another person (e.g., a health care provider), or the device itself may be self-activating, e.g., upon application to the skin of a subject. The activator may be activated once, or multiple times in some cases.

The device may be activated, for example, by pushing a button, flipping a switch, moving a slider, turning a dial, or the like. The subject, and/or another person, may activate the activator. In some cases, the device may be remotely activated. For example, a health care provider may send an electromagnetic signal which is received by the device in order to activate the device, e.g., a wireless signal, a Bluetooth signal, an Internet signal, a radio signal, etc.

Any or all of the arrangements described herein can be provided proximate a subject, for example on or proximate the skin of a subject, in various aspects. Activation of the devices can be carried out in a variety of ways, e.g., as described herein. For example, an on-skin device can be in the form of a patch or the like, optionally including multiple layers for activation, sensing, fluid flow, etc. In one embodiment, a patch or a device can be applied to a subject and a region of the patch or device activated (e.g., pushed, pressed, or tapped by a user) to inject a needle or a microneedle, or other flow activator, so as to access interstitial fluid or blood. The same or a different activation action, e.g., tapping or pushing action, can activate a vacuum source, open and/or close one or more of a variety of valves, or the like. The device can be a simple one in which it is applied to the skin and operates automatically (where e.g., application to the skin of the device allows access to interstitial fluid or blood, and delivers and/or receives fluid) or the patch or other device can be applied to the skin and one tapping or other activation action can cause fluid to flow through administration of one or more needles or microneedles (or other flow activator), opening of a valve, activation of vacuum, etc., or any combination thereof. Any number of activation actions can be carried out by a user repeatedly pushing, tapping, etc. a location or selectively, sequentially, and/or periodically activating a variety of switches.

In another arrangement, activation of one or more needles or microneedles, creation of suction blisters, opening and/or closing of valves, and other techniques to facilitate the receiving of a fluid can be carried out electronically or in other manners facilitated by the subject or by an outside controlling entity (e.g., another user of the device). For example, a device or patch can be provided proximate the skin of a subject and a radio frequency, electromagnetic, or other signal can be provided by a nearby controller or a distant source to activate any of the needles, flow activators, blister devices, valves, or other components of the devices described so that the receiving of a fluid can be carried out as desired.

According to certain aspects of the invention, a vacuum (or reduced pressure) may be used to facilitate the receiving of blood (or other bodily fluids) from the skin of the subject, and/or for causing the blood received from the subject to be separated within the device to form plasma or serum and a portion concentrated in blood cells. Accordingly, in some aspects, the device may contain a suitable vacuum source. In some cases, the vacuum source is one that is self-contained within the device, i.e., the device need not be connected to an external vacuum source (e.g., a house vacuum) during use of the device to receive blood or interstitial fluid from the skin and/or from beneath the skin. In certain embodiments, relatively small vacuum sources may be used, e.g., so that the device may have a relatively small size. For example, the vacuum source may have a volume of less than about 25 ml, less than about 20 ml, less than about 15 ml, less than about 10 ml, less than about 5 ml, less than about 3 ml, less than about 2 ml, or less than about 1 ml.

For example, in one set of embodiments, the vacuum source may include a vacuum chamber having a pressure less than atmospheric or ambient pressure before blood (or other fluid) is received into the device, i.e., the vacuum chamber is at a "negative pressure" (that is, negative relative to atmospheric or ambient pressure) or a "vacuum pressure"

(or just having a "vacuum"). For example, the vacuum in the vacuum chamber may be at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least 600 mmHg, at least 650 mmHg, at least about 700 mmHg, or at least about 750 mmHg, i.e., below atmospheric or ambient pressure. Thus, the pressure within the vacuum is at a "reduced pressure" relative to atmospheric or ambient pressure, e.g., the vacuum chamber is a reduced pressure chamber. However, in other embodiments, it should be understood that other pressures may be used and/or that different methods may be used to produce other pressures (greater than or less than atmospheric or ambient pressure). As non-limiting examples, an external vacuum or a mechanical device may be used as the vacuum source; various additional examples are discussed in detail herein.

As mentioned, the vacuum may be an external vacuum source, and/or the vacuum source may be self-contained within the device. For example, vacuums of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least about 600 mmHg, at least 650 mmHg, at least about 700 mmHg, or at least about 750 mmHg may be applied to the skin. As used herein, "vacuum" refers to pressures that are below atmospheric or ambient pressure.

Any source of vacuum may be used. For example, the device may comprise an internal vacuum source, and/or be connectable to a vacuum source is external to the device, such as a vacuum pump or an external (line) vacuum source. In some cases, vacuum may be created manually, e.g., by manipulating a syringe pump, a plunger, or the like, or the low pressure may be created mechanically or automatically, e.g., using a piston pump, a syringe, a bulb, a Venturi tube, manual (mouth) suction, etc., or the like.

As a specific, non-limiting example, in one embodiment, a device may be used to receive fluid using a vacuum without an external power and/or a vacuum source. Examples of such devices that can use vacuum include skin patches, strips, tapes, bandages, or the like. For instance, a skin patch may be contacted with the skin of a subject, and a vacuum created through a change in shape of a portion of the skin patch or other device (e.g., using a shape memory polymer), which may be used to deliver to and/or receive fluid from the skin and/or beneath the skin. As a specific example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As another example, a mechanical device may be used to create the vacuum, For example, springs, coils, expanding foam (e.g., from a compressed state), a shape memory polymer, shape memory metal, or the like may be stored in a compressed or wound state upon application to a subject, then released (e.g., unwinding, uncompressing, etc.), to mechanically create the vacuum. In some embodiments, the device may be used to create a vacuum automatically, once activated, without any external control by a user.

Thus, in some cases, the device is "pre-packaged" with a suitable vacuum source (e.g., a pre-evacuated vacuum chamber); for instance, in one embodiment, the device may be applied to the skin and activated in some fashion to create and/or access the vacuum source. In yet another example, a chemical reaction may be used to create a vacuum, e.g., a reaction in which a gas is produced, which can be harnessed to provide the mechanical force to create a vacuum. In still another example, a component of the device may be able to create a vacuum in the absence of mechanical force. In another example, the device may include a self-contained vacuum actuator, for example, chemical reactants, a deformable structure, a spring, a piston, etc.

In one set of embodiments, the device may be able to create a pressure differential (e.g. a vacuum). For example, the device may contain a pressure differential chamber, such as a vacuum chamber or a pressurized chamber, that can be used to create a pressure differential. The pressure differential may be created by a pressure regulator. As used here, "pressure regulator" is a pressure controller component or system able to create a pressure differential between two or more locations. The pressure differential should be at least sufficient to urge or move fluid or other material in accordance with various embodiments of the invention as discussed herein, and the absolute pressures at the two or more locations are not important so long as their differential is appropriate, and their absolute values are reasonable for the purposes discussed herein. For example, the pressure regulator may produce a pressure higher than atmospheric or ambient pressure in one location, relative to a lower pressure at another location (atmospheric or ambient pressure or some other pressure), where the differential between the pressures is sufficient to urge or move fluid in accordance with the invention. In another example, the regulator or controller will involve a pressure lower than atmospheric or ambient pressure (a vacuum) in one location, and a higher pressure at another location(s) (atmospheric or ambient pressure or a different pressure) where the differential between the pressures is sufficient to urge or move fluid in accordance with the invention. Wherever "vacuum" or "pressure" is used herein, it should be understood that the opposite can be implemented as well, as would be understood by those of ordinary skill in the art, i.e., a vacuum source can be replaced in many instances with a pressure chamber, for creating a pressure differential suitable for urging the movement of fluid or other material.

The pressure regulator may be an external source of vacuum (e.g. a lab, clinic, hospital, etc., house vacuum line or external vacuum pump), a mechanical device, a vacuum source, pre-packaged vacuum source, a pressurized chamber, or the like. In some cases, vacuum may be created manually, e.g., by manipulating a syringe pump, a plunger, or the like, or the low pressure may be created mechanically or automatically, e.g., using a piston pump, a syringe, a bulb, a Venturi tube, manual (mouth) suction, etc., or the like. Vacuum sources can be used in some embodiments, where the device contains, e.g., regions in which a vacuum exits or can be created (e.g. a variable volume chamber, a change in volume of which will affect vacuum or pressure). A vacuum source can include pre-evacuated (i.e., pre-packaged) chambers or regions, and/or self-contained actuators.

A "self-contained" vacuum (or pressure) regulator means one that is associated with (e.g., on or within) the device, e.g. one that defines an integral part of the device, or is a separate component constructed and arranged to be specifically connectable to the particular device to form a pressure differential (i.e., not a connection to an external source of vacuum such as a hospital's, clinic's, or lab's house vacuum line, or a vacuum pump suitable for general use). In some embodiments, the self-contained vacuum source may be actuated in some fashion to create a vacuum within the device. For instance, the self-contained vacuum source may include a piston, a syringe, a mechanical device such as a vacuum pump able to create a vacuum within the device, and/or chemicals or other reactants that can react to increase or decrease pressure which, with the assistance of mechanical or other means driven by the reaction, can form a pressure differential associated with a pressure regulator. Chemical reaction can also drive mechanical actuation with or without a change in pressure based on the chemical reaction itself. A self-contained vacuum source can also include an expandable foam, a shape memory material, or the like.

One category of self-contained vacuum or pressure regulators of the invention includes self-contained assisted regulators. These are regulators that, upon actuation (e.g., the push of a button, or automatic actuation upon, e.g., removal from a package or urging a device against the skin), a vacuum or pressure associated with the device is formed where the force that pressurizes or evacuates a chamber is not the same as the actuation force. Examples of self-contained assisted regulators include chambers evacuated by expansion driven by a spring triggered by actuation, release of a shape-memory material or expandable material upon actuation, initiation of a chemical reaction upon actuation, or the like.

Another category of self-contained vacuum or pressure regulators of the invention are devices that are not necessarily pre-packaged with pressure or vacuum, but which can be pressurized or evacuated, e.g. by a subject, health care professional at a hospital or clinic prior to use, e.g. by connecting a chamber of the device to a source of vacuum or pressure. For example, the subject, or another person, may actuate the device to create a pressure or vacuum within the device, for example, immediately prior to use of the device.

The vacuum or pressure regulator may be a "pre-packaged" pressure or vacuum source in the device when used (i.e., the device can be provided ready for use by a subject or practitioner with an evacuated region on or in the device, without the need for any actuation to form the initial vacuum). A pre-packaged pressure or vacuum source regulator can, e.g., be a region evacuated (relative to atmospheric or ambient pressure) upon manufacture and/or at some point prior to the point at which it is used by a subject or practitioner. For example, a chamber is evacuated upon manufacture, or after manufacture but before delivery of the device to the user, e.g. the clinician or subject. For instance, in some embodiments, the device contains a vacuum source having a vacuum of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least about 650 mmHg, at least about 700 mmHg, or at least about 750 mmHg below atmospheric or ambient pressure.

In one set of embodiments, a device of the present invention may not have an external power and/or a vacuum source. In some cases, the device is "pre-loaded" with a suitable vacuum source; for instance, in one embodiment, the device may be applied to the skin and activated in some fashion to create and/or access the vacuum source. As one example, a device of the present invention may be contacted with the skin of a subject, and a vacuum created through a change in shape of a portion of the device (e.g., using a shape memory polymer), or the device may contain one or more sealed, self-contained vacuum sources, where a seal is punctured in some manner to create a vacuum. For instance, upon puncturing the seal, a vacuum source may be in fluidic communication with one or more needles, which can be used to move the skin towards the device, receive fluid from the skin and/or beneath the skin, or the like.

As another example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As yet another example, a mechanical device may be used to create the vacuum, For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum. Non-limiting examples of shape-memory polymers and metals include Nitinol, compositions of oligo(epsilon-caprolactone)diol and crystallizable oligo(rho-dioxanone) diol, or compositions of oligo(epsilon-caprolactone)dimethacrylate and n-butyl acrylate.

In yet another example, a chemical reaction may be used to create a vacuum, e.g., a reaction in which a gas is produced, which can be harnessed to provide the mechanical force to create a vacuum. In some embodiments, the device may be used to create a vacuum automatically, once activated, without any external control by a user.

Figure 8:
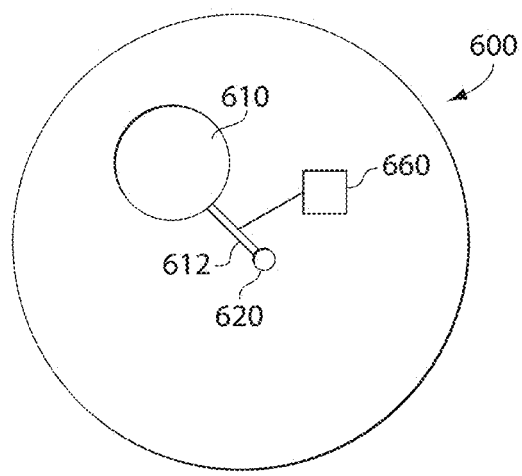
FIG. 8 illustrates a device in one embodiment of the invention, having a vacuum source.

In one set of embodiments, the device contains a vacuum source that is also used as a storage chamber to receive blood, interstitial fluid, or other fluid received from the skin and/or beneath the skin of the subject into the device. For instance, blood received from a subject through or via the fluid transporter may enter the vacuum source due to its negative pressure (i.e., because the chamber has an internal pressure less than atmospheric or ambient pressure) to produce plasma or serum, and the blood, serum, and/or plasma may be optionally stored in the device, e.g., within a storage or collection chamber, or within a vacuum source for later use. A non-limiting example is illustrated in FIG. 8. In this figure, device 600 contains vacuum source 610, which is connected to flow activator 620 (which may be, e.g., one or more needles or microneedles). Upon activation of vacuum source 610 (e.g., using actuator 660, as discussed herein), vacuum source 610 may be put into fluidic communication with flow activator 620. Flow activator 620 may accordingly cause negative pressure to be applied to the skin of the subject, for instance, due to the internal pressure within vacuum source 610. Blood received from the skin and/or beneath the skin via flow activator 620 may accordingly be drawn into the device and into vacuum source 610, e.g., through conduit 612. Upon entry into the device, the blood may be passed across a separation membrane or a membrane that is permeable to fluids but is substantially impermeable to cells.

In another set of embodiments, however, the device may include separate vacuum sources and storage chambers (e.g., chambers to store fluid such as blood, serum, or plasma from the skin and/or beneath the skin of the subject). The vacuum source and storage chambers may be in fluid communication, and may have any suitable arrangement. In some embodiments, the vacuum from the vacuum source may be used, at least in part, to receive fluid from the skin and/or beneath the skin, which is then directed into a storage chamber, e.g., for later analysis or use, for example, as discussed below. As an example, blood may be received into the device, flowing towards a vacuum source, but the blood (or other fluid) may be prevented from entering the vacuum source. For instance, in certain embodiments, a material permeable to gas but not to a liquid such as blood or interstitial fluid may be used. For example, the material may be a membrane such as a hydrophilic or hydrophobic membrane having a suitable porosity, a porous structure, a porous ceramic frit, a dissolvable interface (e.g., formed from a salt or a polymer, etc.), or the like.

Figure 9:
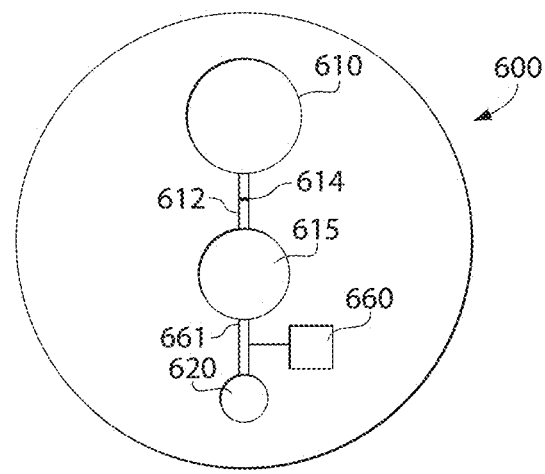
FIG. 9 illustrates a device in another embodiment of the invention, having a vacuum source and a storage chamber.

One non-limiting example is illustrated in FIG. 9. In this figure, device 600 contains vacuum source 610 and storage chamber 615. Vacuum source 610 can be put in fluidic communication with storage chamber 615 via conduit 612, which contains material 614.

Material 614 may be any material permeable to gas but not to a liquid in this example, e.g., material 614 may be a membrane such as a hydrophilic membrane or a hydrophobic membrane that has a porosity that allows gas exchange to occur but does not allow the passage of blood or interstitial fluid from the skin and/or beneath the skin of the subject. When device 600 is actuated using actuator 660, blood (or other fluid) flows through flow activator 620 via conduit 661 into storage chamber 615 because of the internal vacuum pressure from vacuum source 610, which is not completely impeded by material 614 since it is permeable to gases. However, because of material 614, blood (or other bodily fluid) is prevented from entering vacuum source 610, and instead remains in storage chamber 615, e.g., for later analysis or use.

The needle (or other flow activator) may be used for delivering to and/or receiving fluids or other materials from a subject, e.g., to or from the skin and/or beneath the skin. For example, in some cases, a vacuum source having a reduced pressure or an internal pressure less than atmospheric or ambient pressure prior to receiving blood or other bodily fluids (e.g., interstitial fluid) may be used to assist in the receiving of the fluid from the skin after the needle (or other flow activator) has penetrated the skin. The fluid received from the skin and/or beneath the skin may be collected in the vacuum source and/or in a storage chamber. The storage chamber may be separated from the vacuum source using a gas permeable membrane (e.g., one that is substantially impermeable to blood or other bodily fluids), a hydrophobic membrane, a hydrophilic membrane, a porous structure, a dissolvable interface, or the like, e.g., as is discussed herein.

In some embodiments, the flow of blood (or other fluid, e.g., interstitial fluid) into the storage chamber may be controlled using a flow controller. The flow controller may be manually and/or automatically controlled to control the flow of blood. The flow controller may activate or deactivate when a certain amount or volume of fluid has entered the storage chamber in certain cases. For instance, the flow controller may stop blood flow after a predetermined amount or volume of blood has entered the storage chamber, and/or the flow controller may be able to control the internal pressure of the storage chamber, e.g., to a specific level, such as a predetermined level. Examples of suitable flow controllers for the device include, but are not limited to, a membrane, a valve, a dissolvable interface, a gate, or the like.

Figure 10:
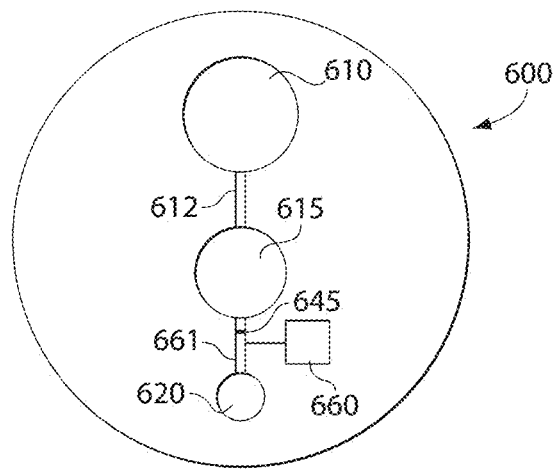
FIG. 10 illustrates a device in yet another embodiment of the invention, having a flow controller.

One non-limiting example of a flow controller is now illustrated with reference to FIG. 10. In this example figure, device 600 includes a vacuum source 610 and a storage chamber 615. Fluid entering device 600 via flow activator 620 is prevented from entering storage chamber 615 due to flow controller 645 present within conduit 611. However, under suitable conditions, flow controller 645 may be opened, thereby allowing at least some fluid to enter storage chamber 615. In some cases, for instance, storage chamber 615 also contains at least a partial vacuum, although this vacuum may be greater or less than the pressure within chamber 610. In other embodiments, flow controller 645 may initially be open, or be externally controllable (e.g., via an actuator), or the like. In some cases, the flow controller may control the flow of fluid into the device such that, after collection, at least some vacuum is still present in the device. Although the flow controller 645 is shown between the storage chamber 615 and the flow activator 620, the flow controller 645 (e.g., a controllable valve) may be positioned between the chamber 610 and the storage chamber 615.

Thus, in some cases, the device may be constructed and arranged to reproducibly obtain from the skin and/or from beneath the skin of the subject a controlled amount of fluid, e.g., a controlled amount or volume of blood or interstitial fluid. The amount of fluid reproducibly obtained from the skin and/or beneath the skin of the subject may be controlled, for example, using flow controllers, materials permeable to gas but not to liquids, membranes, valves, pumps, gates, microfluidic systems, or the like, as discussed herein. In particular, it should be noted that the volume of blood or other fluid obtained from the skin and/or beneath the skin of the subject need not be strictly a function of the initial vacuum pressure or volume within the device. For example, a flow controller may initially be opened (e.g., manually, automatically, electronically, etc.) to allow fluid to begin entering the device; and when a predetermined condition is reached (e.g., when a certain volume or amount of blood or interstitial fluid has entered the device), the flow controller may be closed at that point, even if some vacuum remains within the device. In some cases, this control of fluid allows the amount of fluid reproducibly obtained from the skin and/or beneath the skin of the subject to be controlled to a great extent. For example, in one set of embodiments, the amount of fluid received from the skin and/or beneath the skin of the subject may be controlled to be less than about 1 ml, may be less than about 300 microliters, less than about 200 microliters, less than about 100 microliters, less than about 50 microliters, less than about 30 microliters, less than about 20 microliters, less than about 10 microliters, less than about 5 microliters, less than about 3 microliters, less than about 2 microliters, less than about 1 microliter, etc.

Figure 11:
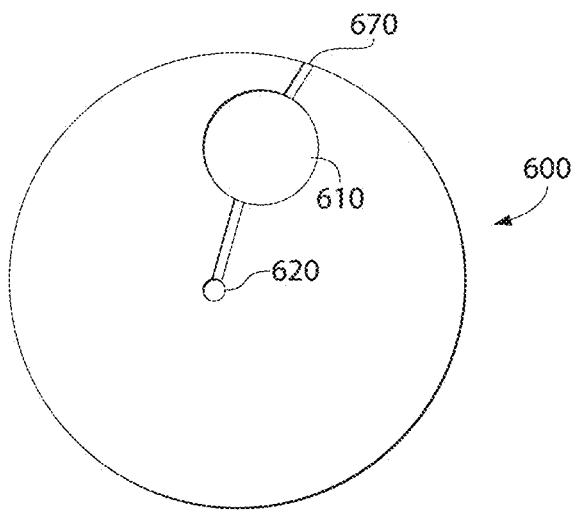
FIG. 11 illustrates a device according to another embodiment of the invention, having an exit port.

In some embodiments, the device may be connected to an external apparatus for determining at least a portion of the device, a fluid (e.g., plasma or serum) removed from the device, an analyte suspected of being present within the fluid, or the like. For example, the device may be connected to an external analytical apparatus, and fluid removed from the device for later analysis, or the fluid may be analyzed within the device in situ, e.g., by adding one or more reaction entities to the device, for instance, to a storage chamber, or to analytical chamber within the device. For example, in one embodiment, the external apparatus may have a port or other suitable surface for mating with a port or other suitable surface on the device, and blood, interstitial fluid, or other fluid can be removed from the device using any suitable technique, e.g., using vacuum or pressure, etc. The blood or other fluid may be removed by the external apparatus, and optionally, stored and/or analyzed in some fashion. For example, in one set of embodiments, the device may include an exit port for removing a fluid from the device (e.g., blood). In some embodiments, fluid contained within a storage chamber in the device may be removed from the device, and stored for later use or analyzed outside of the device. In some cases, the exit port may be separate from the flow activator. An example is shown with exit port 670 and flow activator 620 in device 600 in FIG. 11. As shown in this figure, the exit port can be in fluidic communication with vacuum source 610. As another example, an exit port can be in fluidic communication with a vacuum source, which can also serve as a fluid reservoir in some cases. Other methods for removing blood, interstitial fluid, or other fluids from the device include, but are not limited to, removal using a vacuum line, a pipette, extraction through a septum instead of an exit port, or the like. In some cases, the device may also be positioned in a centrifuge and subjected to various g forces (e.g., to a centripetal force of at least 50 g), e.g., to cause at separation of cells or other substances within a fluid within the device to occur.

As mentioned, in accordance with some aspects, blood, plasma, serum, interstitial fluid, or other bodily fluids may be stored within the device for later use and/or analysis. For instance, the device may include a storage chamber having an internal pressure less than atmospheric or ambient pressure prior to receiving blood, plasma, serum, interstitial fluid, or other bodily fluids. In certain embodiments, relatively small storage chambers may be used, e.g., so that the device may have a relatively small size. For example, the storage chamber may have a volume of less than about 25 ml, less than about 20 ml, less than about 15 ml, less than about 10 ml, less than about 5 ml, less than about 3 ml, less than about 2 ml, or less than about 1 ml.

In one set of embodiments, the device may include an anticoagulant or a stabilizing agent for stabilizing the fluid received from the skin and/or beneath the skin, e.g., within the storage chamber. For example, the fluid may be stored within the device for a certain period of time, and/or the device (or a portion thereof) may be moved or shipped to another location for analysis or later use. For instance, a device may contain anticoagulant or a stabilizing agent in a storage chamber. In some cases, more than one anticoagulant may be used, e.g., in the same storage chamber, or in more than one storage chamber.

The device may include an anticoagulant or a stabilizing agent for stabilizing the fluid received from the skin and/or beneath the skin. As a specific non-limiting example, an anticoagulant may be used for blood received from the skin. Examples of anticoagulants include, but are not limited to, heparin, citrate, thrombin, oxalate, ethylenediaminetetraacetic acid (EDTA), sodium polyanethol sulfonate, acid citrate dextrose. Other agents may be used in conjunction with or instead of anticoagulants, for example, stabilizing agents such as solvents, diluents, buffers, chelating agents, antioxidants, binding agents, preservatives, antimicrobials, or the like. Examples of preservatives include, for example, benzalkonium chloride, chlorobutanol, parabens, or thimerosal. Non-limiting examples of antioxidants include ascorbic acid, glutathione, lipoic acid, uric acid, carotenes, alpha-tocopherol, ubiquinol, or enzymes such as catalase, superoxide dismutase, or peroxidases. Examples of microbials include, but are not limited to, ethanol or isopropyl alcohol, azides, or the like. Examples of chelating agents include, but are not limited to, ethylene glycol tetraacetic acid or ethylenediaminetetraacetic acid. Examples of buffers include phosphate buffers such as those known to ordinary skill in the art.

In one set of embodiments, at least a portion of the device may be colored to indicate the anticoagulant(s) contained within the device. In some cases, the colors used may be identical or equivalent to that commercially used for Vacutainers™, Vacuettes™, or other commercially-available phlebotomy equipment. For example, lavender and/or purple may indicate ethylenediaminetetraacetic acid, light blue may indicate citrate, dark blue may indicate ethylenediaminetetraacetic acid, green may indicate heparin, gray may indicate a fluoride and/or an oxalate, orange may indicate a thrombin, yellow may indicate sodium polyanethol sulfonate and/or acid citrate dextrose, black may indicate citrate, brown may indicate heparin, etc. In other embodiments, however, other coloring systems may be used.

Other coloring systems may be used in other embodiments of the invention, not necessarily indicative of anticoagulants. For example, in one set of embodiments, the device carries a color indicative of a recommended bodily use site for the device, e.g., a first color indicative of a device suitable for placement on the back, a second color indicative of a device suitable for placement on a leg, a third color indicative of a device suitable for placement on the arm, etc.

As mentioned, in one set of embodiments, a device of the invention as discussed herein may be shipped to another location for analysis. In some cases, the device may include an anticoagulant or a stabilizing agent contained within the device, e.g., within a storage chamber for the fluid. Thus, for example, fluid such as blood or interstitial fluid received from the skin and/or beneath the skin may be delivered to a chamber (e.g., a storage chamber) within the device, then the device, or a portion of the device (e.g., a module) may be shipped to another location for analysis. Any form of shipping may be used, e.g., via mail.

In some embodiments, the device may be attached to a suitable external apparatus able to analyze a portion of the device (e.g., containing a fluid, such as blood, serum, or plasma), and/or the external apparatus may remove at least some of the blood, plasma, serum, or other fluid from the device for subsequent analysis and/or storage. In some cases, however, at least some analysis may be performed by the device itself, e.g., using one or more sensors, etc., contained within the device. In some cases, the chambers may be in fluidic communication with one or more fluid transporters and/or one or more microfluidic channels. For instance, the device may contain a chamber for collecting fluid received from a subject (e.g., for storage and/or later analysis), a chamber for containing a fluid for delivery to the subject (e.g., blood, saline, optionally containing drugs, hormones, vitamins, pharmaceutical agents, or the like), etc.

For example, as discussed in detail below, in some cases, a storage chamber may contain a reagent or a reaction entity able to react with an analyte suspected of being present in the blood (or other fluid, e.g., plasma or serum) entering the device, and in some cases, the reaction entity may be determined to determine the analyte. In some cases, the determination may be made externally of the device, e.g., by determining a color change or a change in fluorescence, etc. The determination may be made by a person, or by an external apparatus able to analyze at least a portion of the device. In some cases, the determination may be made without removing blood, serum, or plasma from the device, e.g., from the storage chamber. (In other cases, however, blood or other fluids may first be removed from the device before being analyzed.) For example, the device may include one or more sensors (e.g., ion sensors such as $K^+$ sensors, colorimetric sensors, fluorescence sensors, etc.), and/or contain "windows" that allow light to penetrate the device. The windows may be forming of glass, plastic, etc., and may be selected to be at least partially transparent to one or a range of suitable wavelengths, depending on the analyte or condition to be determined. As a specific example, the entire device (or a portion thereof) may be mounted in an external apparatus, and light from the external apparatus may pass through or otherwise interact with at least a portion of the device (e.g., be reflected or refracted via the device) to determine the analyte and/or the reaction entity.

After receiving fluid into the device, the device, or a portion thereof, may be removed from the skin of the subject, e.g., by the subject or by another person. For example, the entire device may be removed, or a portion of the device containing the storage reservoir may be removed from the device, and optionally replaced with another storage reservoir. Thus, for instance, in one embodiment, the device may contain two or more modules, for example, a first module that is able to cause receiving of fluid from the skin into a storage reservoir, and a second module containing the storage module. In some cases, the module containing the storage reservoir may be removed from the device. Other examples of modules and modular systems are discussed herein; still other examples are discussed in U.S. Provisional Patent Application Ser. No. 61/256,931, filed Oct. 30, 2009, entitled "Modular Systems for Application to the Skin," incorporated by reference herein in its entirety.

The received fluid may then be sent to a clinical and/or laboratory setting, e.g., for analysis. In some embodiments, the entire device may be sent to the clinical and/or laboratory setting; in other embodiments, however, only a portion of the device (e.g., a module containing a storage reservoir containing the fluid) may be sent to the clinical and/or laboratory setting. In some cases, the fluid may be shipped using any suitable technique (e.g., by mail, by hand, etc.). In certain instances, the subject may give the fluid to appropriate personnel at a clinical visit. For instance, a doctor may prescribe a device as discussed above for use by the subject, and at the next doctor visit, the subject may give the doctor the received fluid, e.g., contained within a device or module.

The device, in certain aspects, may contain a portion able to determine a fluid removed from the skin. For example, in some cases, a device can be applied to the skin, and activated to receive fluid from the skin and/or beneath the skin of the subject. The device, or a portion thereof, may then be processed to determine the fluid and/or an analyte within the fluid, alone or with an external apparatus. For example, fluid may be received from the device, and/or the device may contain sensors or agents able to determine the fluid and/or an analyte suspected of being contained in the fluid. For example, a portion of the device may contain a sensor, or reagents able to interact with an analyte contained or suspected to be present within the received fluid from the skin of the subject, for example, a marker for a disease state. For example, the sensor may determine plasma, serum, or blood that has been received from the subject.

The sensor may be embedded within or integrally connected to the device, or positioned remotely but with physical, electrical, and/or optical connection with the device so as to be able to sense a chamber within or fluid from the device. For example, the sensor may be in fluidic communication with fluid received from a subject, directly, via a microfluidic channel, an analytical chamber, etc. The sensor may be able to sense an analyte, e.g., one that is suspected of being in a fluid received from a subject. For example, a sensor may be free of any physical connection with the device, but may be positioned so as to detect the results of interaction of electromagnetic radiation, such as infrared, ultraviolet, or visible light, which has been directed toward a portion of the device, e.g., a chamber within the device. As another example, a sensor may be positioned on or within the device, and may sense activity in a chamber by being connected optically to the chamber. Sensing communication can also be provided where the chamber is in communication with a sensor fluidly, optically or visually, thermally, pneumatically, electronically, or the like, so as to be able to sense a condition of the chamber. As one example, the sensor may be positioned downstream of a chamber, within a channel such a microfluidic channel, on an external apparatus, or the like.

Thus, the invention provides, in certain embodiments, sensors able to determine an analyte. Such determination may occur within the skin, and/or externally of the subject, e.g., within a device on the surface of the skin, depending on the embodiment. "Determine," in this context, generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction, e.g. determination of the binding between two species. The species may be, for example, a bodily fluid and/or an analyte suspected of being present in the bodily fluid. "Determining" also means detecting or quantifying interaction between species or identifying or otherwise assessing one or more characteristics of the sample, such as the presence and/or concentration of one or more species, a physical and/or chemical property of the sample, etc.

Fluids received from the skin and/or from beneath the skin of the subject will often contain various analytes within the body that are important for diagnostic purposes, for example, markers for various disease states, such as glucose (e.g., for diabetics); other example analytes include ions such as sodium, potassium, chloride, calcium, magnesium, and/or bicarbonate (e.g., to determine dehydration); gases such as carbon dioxide or oxygen; $H^+$ (i.e., pH); metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Other examples include insulin, or hormone levels. Still other analytes include, but not limited to, high-density lipoprotein ("HDL"), low-density lipoprotein ("LDL"), albumin, alanine transaminase ("ALT"), aspartate transaminase ("AST"), alkaline phosphatase ("ALP"), bilirubin, lactate dehydrogenase, etc. (e.g., for liver function tests); luteinizing hormone or beta-human chorionic gonadotrophin (hCG) (e.g., for fertility tests); prothrombin (e.g., for coagulation tests); troponin, BNT or B-type natriuretic peptide, etc., (e.g., as cardiac markers); infectious disease markers for the flu, respiratory syncytial virus or RSV, etc.; or the like.

The sensor may be, for example, a pH sensor, an optical sensor, an oxygen sensor, a sensor able to detect the concentration of a substance, or the like. Non-limiting examples of sensors useful in the invention include dye-based detection systems, affinity-based detection systems, microfabricated gravimetric analyzers, CCD cameras, optical detectors, optical microscopy systems, electrical systems, thermocouples and thermistors, pressure sensors, etc. Those of ordinary skill in the art will be able to identify other suitable sensors. The sensor can include a colorimetric detection system in some cases, which may be external to the device, or microfabricated into the device in certain cases. As an example of a colorimetric detection system, if a dye or a fluorescent entity is used (e.g. in a particle), the colorimetric detection system may be able to detect a change or shift in the frequency and/or intensity of the dye or fluorescent entity.

Examples of sensors include, but are not limited to, pH sensors, optical sensors, ion sensors, colorimetric sensors, a sensor able to detect the concentration of a substance, or the like, e.g., as discussed herein. For instance, in one set of embodiments, the device may include an ion selective electrode. The ion selective electrode may be able to determine a specific ion and/or ions such as $K^+$, $H^+$, $Na^+$, $Ag^+$, $Pb^{2+}$, $Cd^{2+}$, or the like. Various ion selective electrodes can be obtained commercially. As a non-limiting example, a potassium-selective electrode may include an ion exchange resin membrane, using valinomycin, a potassium channel, as the ion carrier in the membrane to provide potassium specificity.

Examples of analytes that the sensor may be used to determine include, but are not limited to, pH or metal ions, proteins, nucleic acids (e.g. DNA, RNA, etc.), drugs, sugars (e.g., glucose), hormones (e.g., estradiol, estrone, progesterone, progestin, testosterone, androstenedione, etc.), carbohydrates, or other analytes of interest. Other conditions that can be determined can include pH changes, which may indicate disease, yeast infection, periodontal disease at a mucosal surface, oxygen or carbon monoxide levels which indicate lung dysfunction, and drug levels, e.g., legal prescription levels of drugs such as coumadin, other drugs such as nicotine, or illegal drugs such as cocaine. Further examples of analytes include those indicative of disease, such as cancer specific markers such as CEA and PSA, viral and bacterial antigens, and autoimmune indicators such as antibodies to double stranded DNA, indicative of Lupus. Still other conditions include exposure to elevated carbon monoxide, which could be from an external source or due to sleep apnea, too much heat (important in the case of babies whose internal temperature controls are not fully self-regulating) or from fever. Still other potentially suitable analytes include various pathogens such as bacteria or viruses, and/or markers produced by such pathogens.

As additional non-limiting examples, the sensor may contain an antibody able to interact with a marker for a disease state, an enzyme such as glucose oxidase or glucose 1-dehydrogenase able to detect glucose, or the like. The analyte may be determined quantitatively or qualitatively, and/or the presence or absence of the analyte within the received fluid may be determined in some cases. Those of ordinary skill in the art will be aware of many suitable commercially-available sensors, and the specific sensor used may depend on the particular analyte being sensed. For instance, various non-limiting examples of sensor techniques include pressure or temperature measurements, spectroscopy such as infrared, absorption, fluorescence, UV/visible, FTIR ("Fourier Transform Infrared Spectroscopy"), or Raman; piezoelectric measurements; immunoassays; electrical measurements, electrochemical measurements (e.g., ion-specific electrodes); magnetic measurements, optical measurements such as optical density measurements; circular dichroism; light scattering measurements such as quasielectric light scattering; polarimetry; refractometry; chemical indicators such as dyes; or turbidity measurements, including nephelometry.

In one set of embodiments, a sensor in the device may be used to determine a condition of the blood, interstitial fluid, or other fluid present within the device. For example, the sensor may indicate the condition of analytes commonly found within the blood or interstitial fluid, for example, $O_2$, $K^+$, hemoglobin, $Na^+$, glucose, or the like. As a specific non-limiting example, in some embodiments, the sensor may determine the degree of hemolysis within blood contained within the device. Without wishing to be bound by any theory, it is believed that in some cases, hemolysis of red blood cells may cause the release of potassium ions and/or free hemoglobin into the blood. By determining the levels of potassium ions, and/or hemoglobin (e.g., by subjecting the device and/or the blood to separate cells from plasma, then determining hemoglobin in the plasma using a suitable colorimetric assay), the amount of blood lysis or "stress" experienced by the blood contained within the device may be determined. Accordingly, in one set of embodiments, the device may indicate the usability of blood (or other fluid) contained within the device, e.g., by indicating the degree of stress or the amount of blood lysis. Other examples of devices suitable for indicating the usability of blood (or other fluid) contained within the device are also discussed herein (e.g., by indicating the amount of time blood has been contained in the device, the temperature history of the device, etc.).

In some embodiments, an analyte may be determined as an "on/off" or "normal/abnormal" situation. Detection of the analyte, for example, may be indicative that insulin is needed; a trip to the doctor to check cholesterol; ovulation is occurring; kidney dialysis is needed; drug levels are present (e.g., especially in the case of illegal drugs) or too high/too low (e.g., important in care of geriatrics in particular in nursing homes). As another embodiment, however, an analyte may be determined quantitatively.

In some cases, fluids received from the subject, such as plasma, or serum, will often contain various analytes within the body that are important for diagnostic purposes, for example, markers for various disease states, such as glucose (e.g., for diabetics); other example analytes include ions such as sodium, potassium, chloride, calcium, magnesium, and/or bicarbonate (e.g., to determine dehydration); gases such as carbon dioxide or oxygen; $H^+$ (i.e., pH); metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Other examples include insulin, or hormone levels. As discussed herein, certain embodiments of the present invention are generally directed at methods for receiving fluids from the body, and optionally determining one or more analytes within the received fluid. Thus, in some embodiments, at least a portion of the fluid may be stored, and/or analyzed to determine one or more analytes, e.g., a marker for a disease state, or the like. The fluid received from the skin and/or beneath the skin may be subjected to such uses, and/or one or more materials previously delivered to the skin may be subject to such uses.

Still other potentially suitable analytes include various pathogens such as bacteria or viruses, and/or markers produced by such pathogens. Thus, in certain embodiments of the invention, as discussed below, one or more analytes may be determined in some fashion, which may be useful in determining a past, present and/or future condition of the subject.

In one set of embodiments, the sensor may be a test strip, for example, test strips that can be obtained commercially. Examples of test strips include, but are not limited to, glucose test strips, urine test strips, pregnancy test strips, or the like. A test strip will typically include a band, piece, or strip of paper or other material and contain one or more regions able to determine an analyte, e.g., via binding of the analyte to a diagnostic agent or a reaction entity able to interact with and/or associate with the analyte. For example, the test strip may include various enzymes or antibodies, glucose oxidase and/or ferricyanide, or the like. The test strip may be able to determine, for example, glucose, cholesterol, creatinine, ketones, blood, protein, nitrite, pH, urobilinogen, bilirubin, leucocytes, luteinizing hormone, etc., depending on the type of test strip. The test strip may be used in any number of different ways. In some cases, a test strip may be obtained commercially and inserted into the device, e.g., before or after receiving blood, interstitial fluid, or other fluids from a subject. At least a portion of the blood or other fluid may be exposed to the test strip to determine an analyte, e.g., in embodiments where the device uses the test strip as a sensor so that the device itself determines the analyte. In some cases, the device may be sold with a test strip pre-loaded, or a user may need to insert a test strip in a device (and optionally, withdraw and replace the test strip between uses). In certain cases, the test strip may form an integral part of the device that is not removable by a user. In some embodiments, after exposure to the blood or other fluid received from the subject, the test strip may be removed from the device and determined externally, e.g., using other apparatuses able to determine the test strip, for example, commercially-available test strip readers.

According to one aspect of the invention, the device is of a relatively small size. In some embodiments, the device may be sized such that it is wearable and/or carryable by a subject. For example, the device may be self-contained, needing no wires, cables, tubes, external structural elements, or other external support. The device may be positioned on any suitable position of the subject, for example, on the arm or leg, on the back, on the abdomen, etc.

In some embodiments, the device may be a handheld device that is applied to the surface of the skin of a subject. In some cases, however, the device may be sufficiently small or portable that the subject can self-administer the device. In certain embodiments, the device may also be powered. In some instances, the device may be applied to the surface of the skin, and is not inserted into the skin. In other embodiments, however, at least a portion of the device may be inserted into the skin, for example, mechanically. For example, in one embodiment, the device may include a cutter, such as a hypodermic needle, a knife blade, a piercing element (e.g., a solid or hollow needle), or the like, as discussed herein.

In another set of embodiments, the device may be an electrical and/or a mechanical device applicable or affixable to the surface of the skin, e.g., using adhesive, or other techniques such as those described herein. For example, in one set of embodiments, the device may include a support structure that contains an adhesive that can be used to immobilize the device to the skin. The adhesive may be permanent or temporary, and may be used to affix the device to the surface of the skin. The adhesive may be any suitable adhesive, for example, a pressure sensitive adhesive, a contact adhesive, a permanent adhesive, a cyanoacrylate, glue, gum, hot melts, an epoxy, a hydrogel, a hydrocolloid, or the like. In some cases, the adhesive is chosen to be biocompatible or hypoallergenic.

In another set of embodiments, the device may be mechanically held to the skin. For instance, the device may include mechanical elements such as straps, belts, buckles, strings, ties, elastic bands, or the like. For example, a strap may be worn around the device to hold the device in place against the skin of the subject. In yet another set of embodiments, a combination of these and/or other techniques may be used. As one non-limiting example, the device may be affixed to a subject's arm or leg using adhesive and a strap.

Thus, in some embodiments, the device may be affixed or held onto the surface of the skin using any suitable technique, e.g., using adhesives, mechanical elements such as straps, belts, buckles, strings, ties, elastic bands, or the like. In some cases, the device may be positioned on the subject such that the subject is able to move around (e.g., walking, exercising, typing, writing, drinking or eating, using the bathroom, etc.) while wearing the device. For example, the device may have a mass and/or dimensions such that the subject is able to wear the device for at least about 5 minutes, and in some cases for longer periods of time, e.g., at least about 10 minutes, at least about 15 minutes, at least about 30 minutes, at least about 45 minutes, at least about 1 hour, at least about 3 hours, at least 5 hours, at least about 8 hours, at least about 1 day, at least about 2 days, at least about 4 days, at least about 1 week, at least about 2 weeks, at least about 4 weeks, etc.

In some embodiments, the device is relatively lightweight. For example, the device may have a mass of no more than about 1 kg, no more than about 300 g, no more than about 150 g, no more than about 100 g, no more than about 50 g, no more than about 30 g, no more than about 25 g, no more than about 20 g, no more than about 10 g, no more than about 5 g, or no more than about 2 g. For instance, in various embodiments, the device has a mass of between about 2 g and about 25 g, a mass of between about 2 g and about 10 g, a mass of between 10 g and about 50 g, a mass of between about 30 g and about 150 g, etc.

The device, in some cases, may be relatively small. For example, the device may be constructed and arranged to lie relatively close to the skin. Thus, for instance, the device may have a largest vertical dimension (e.g., a dimension perpendicular to the skin), extending from the skin of the subject when the device is positioned on the skin, of no more than about 25 cm, no more than about 10 cm, no more than about 7 cm, no more than about 5 cm, no more than about 3 cm, no more than about 2 cm, no more than about 1 cm, no more than about 8 mm, no more than about 5 mm, no more than about 3 mm, no more than about 2 mm, no more than about 1 mm, or no more than about 0.5 mm. In some cases, the device may have a largest vertical dimension of between about 0.5 cm and about 1 cm, between about 2 and about 3 cm, between about 2.5 cm and about 5 cm, between about 2 cm and about 7 cm, between about 0.5 mm and about 7 cm, etc.

In another set of embodiments, the device may have a relatively small size. For example, the device may have a largest lateral dimension (e.g., parallel to the skin) of no more than about 25 cm, no more than about 10 cm, no more than about 7 cm, no more than about 5 cm, no more than about 3 cm, no more than about 2 cm, or no more than about 1 cm. In some cases, the device may have a largest lateral dimension of between about 0.5 cm and about 1 cm, between about 2 and about 3 cm, between about 2.5 cm and about 5 cm, between about 2 cm and about 7 cm, etc.

Combinations of these and/or other dimensions are also possible in other embodiments. As non-limiting examples, the device may have a largest lateral dimension of no more than about 5 cm, a largest vertical dimension of no more than about 1 cm, and a mass of no more than about 25 g; or the device may have a largest lateral dimension of no more than about 5 cm, a largest vertical dimension of no more than about 1 cm, and a mass of no more than about 25 g; etc. A variety of materials and methods, according to certain aspects of the invention, can be used to form the device, e.g., microfluidic channels, chambers, etc. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al).

In one set of embodiments, various components of the systems and devices of the invention can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science,* 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering,* 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a polyester, a fluorinated derivative of a polyimide, or the like. Another example is polyethylene terephthalate glycol ("PETG"). In PETG, the ethylene glycol group that is normally part of the PET chain is partially substituted for cyclohexane dimethanol (e.g., approximately 15-35 mol % of the ethylene groups are replaced), which may, in some cases, slow down the crystallization of the polymer when injection molded to allow better processing. Combinations, copolymers, derivatives, or blends involving polymers including those described above are also envisioned. The device may also be formed from composite materials, for example, a composite of a polymer and a semiconductor material.

In some embodiments, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.,* 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one aspect, a subject having a condition such as a physiological condition to be analyzed (or other user, such as medical personnel) reads and/or otherwise determines a signal from a device. For example, the device may transmit a signal indicative of a condition of the subject and/or the device. Alternatively, or in addition, a signal produced by a device can be acquired in the form of a representation (e.g. a digitized signal, or the like) and transmitted to another entity for analysis and/or action. For example, a signal can be produced by a device, e.g., based on a sensor reading of an analyte, based on fluid delivered to and/or received from the skin and/or beneath the skin, based on a condition of the device, or the like. The signal may represent any suitable data or image. For example, the signal may represent the presence and/or concentration of an analyte in fluid received from a subject, the amount of fluid received from a subject and/or delivered to the subject, the number of times the device has been used, the battery life of the device, the amount of vacuum left in the device, the cleanliness or sterility of the device, the identity of the device (e.g., where multiple devices are given unique identification numbers, to prevent counterfeiting, accidental exchange of equipment to incorrect users, etc.), or the like. For instance, in one set of embodiments, an image of the signal (e.g., a visual image or photograph) can be obtained and transmitted to a different entity (for example, a user can take a cell phone picture of a signal generated by the device and send it, via cell phone, to the other entity).

The other entity that the signal is transmitted to can be a human (e.g., a clinician) or a machine. In some cases, the other entity may be able to analyze the signal and take appropriate action. In one arrangement, the other entity is a machine or processor that analyzes the signal and optionally sends a signal back to the device to give direction as to activity (e.g., a cell phone can be used to transmit an image of a signal to a processor which, under one set of conditions, transmits a signal back to the same cell phone giving direction to the user, or takes other action). Other actions can include automatic stimulation of the device or a related device to dispense a medicament or pharmaceutical, or the like. The signal to direct dispensing of a pharmaceutical can take place via the same used to transmit the signal to the entity (e.g., cell phone) or a different vehicle or pathway. Telephone transmission lines, wireless networks, Internet communication, and the like can also facilitate communication of this type.

As one specific example, a device may be a glucose monitor. A signal may be generated by the device and an image of the signal captured by a cell phone camera and then transmitted via cell phone to a clinician. The clinician may then determine that the glucose (or e.g., insulin) level is appropriate or inappropriate and send a message indicating this back to the subject via cell phone.

Information regarding the analysis can also be transmitted to the same or a different entity, or a different location simply by removing the device or a portion of the device from the skin of the subject and transferring it to a different location. For example, a device can be used in connection with a subject to analyze presence and/or amount of a particular analyte. At some point after the onset of use, the device, or a portion of the device carrying a signal or signals indicative of the analysis or analyses, can be removed and, e.g., attached to a record associated with the subject. As a specific example, a patch or other device can be worn by a subject to determine presence and/or amount of one or more analytes qualitatively, quantitatively, and/or over time. The subject can visit a clinician who can remove the patch or a portion of the patch (or other device) and attach it to a medical record associated with the subject.

In another aspect, the present invention is directed to a kit including one or more of the compositions previously discussed, e.g., a kit including a device for the delivery to and/or the receiving of fluid from the skin and/or beneath the skin, a kit including a device able to create a pooled region of fluid within the skin of a subject, a kit including a device able to determine a fluid, or the like. A "kit," as used herein, typically defines a package or an assembly including one or more of the compositions or devices of the invention, and/or other compositions or devices associated with the invention, for example, as previously described. For example, in one set of embodiments, the kit may include a device and one or more compositions for use with the device. Each of the compositions of the kit, if present, may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or subcontractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following documents are incorporated herein by reference: U.S. patent application Ser. No. 12/478,756, filed Jun. 4, 2009, entitled "Compositions and Methods for Diagnostics, Therapies, and Other Applications," by Levinson, published as U.S. Pat. Apl. Pub. No. 2010/0069726 on Mar. 18, 2010; U.S. patent application Ser. No. 12/716,222, filed Mar. 2, 2010, entitled "Oxygen Sensor," by Levinson, et al., published as U.S. Pat. Apl. Pub. No. 2010/0249560 on Sep. 30, 2010; U.S. patent application Ser. No. 12/716,233, filed Mar. 2, 2010, entitled "Systems and Methods for Creating and Using Suction Blisters or Other Pooled Regions of Fluid within the Skin," by Levinson, et al., published as U.S. Pat. Apl. Pub. No. 2011/0009847 on Jan. 13, 2011; U.S. patent application Ser. No. 12/716,226, filed Mar. 2, 2010, entitled "Techniques and Devices Associated with Blood Sampling," by Levinson, et al., published as U.S. Pat. Apl. Pub. No. 2010/0256524 on Oct. 7, 2010; U.S. patent application Ser. No. 12/716,229, filed Mar. 2, 2010, entitled "Devices and Techniques Associated with Diagnostics, Therapies, and Other Applications, Including Skin-Associated Applications," by Bernstein, et al., published as U.S. Pat. Apl. Pub. No. 2010/0256465 on Oct. 7, 2010; U.S. patent application Ser. No. 12/953,744, filed Nov. 24, 2010, entitled "Patient-Enacted Sampling Technique," by Levinson, et al.; U.S. patent application Ser. No. 12/915,735, filed Oct. 29, 2010, entitled "Systems and Methods for Application to Skin and Control of Actuation, Delivery, and/or Perception Thereof," by Chickering, et al.; U.S. patent application Ser. No. 12/915,789, filed Oct. 29, 2010, entitled "Systems and Methods for Treating, Sanitizing, and/or Shielding the Skin or Devices Applied to the Skin," by Bernstein, et al.; U.S. patent application Ser. No. 12/915,820, filed Oct. 29, 2010, entitled "Relatively Small Devices Applied to the Skin, Modular Systems, and Methods of Use Thereof," by Bernstein, et al.; U.S. patent application Ser. No. 13/006,177, filed Jan. 13, 2011, entitled "Rapid Delivery and/or Withdrawal of Fluids," by Chickering, et al.; U.S. patent application Ser. No. 13/006,165, filed Jan. 13, 2011, entitled "Sampling Device Interfaces," by Chickering, et al.; U.S. Prov. Pat. Apl. Ser. No. 61/357,582, filed Jun. 23, 2010, entitled "Sampling Devices and Methods Involving Relatively Little Pain," by Chickering, et al.; U.S. Prov. Pat. Apl. Ser. No. 61/367,607, filed Jul. 26, 2010, entitled "Rapid Delivery and/or Withdrawal of Fluids," by Davis, et al.; U.S. Prov. Pat. Apl. Ser. No. 61/373,764, filed Aug. 13, 2010, entitled "Clinical and/or Consumer Techniques and Devices," by Chickering, et al.; and U.S. Prov. Pat. Apl. Ser. No. 61/411,566, filed Nov. 9, 2010, entitled "Systems and Interfaces for Blood Sampling," by Brancazio, et al.

Also incorporated herein by reference in its entirety is U.S. provisional patent application 61/480,941, entitled "Plasma or Serum Production and Removal of Fluids under Reduced Pressure," filed Apr. 29, 2011.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of receiving bodily fluid from a subject, the method comprising:
    applying, to the skin of a subject, a device comprising a fluid transporter having a recess and a flow activator, a channel having an inlet in fluid communication with the recess, and a vacuum source having a pressure less than ambient pressure, the recess positioned to collect bodily fluid on the skin of the subject that is released by the flow activator;
    receiving a bodily fluid from the skin into the recess and into a groove positioned in the recess, the groove extending from the inlet and being in fluid communication with the inlet; and
    moving the bodily fluid from the groove into the channel and toward the vacuum source due to a difference in pressure between the recess and the vacuum source.

2. The method of claim 1, wherein the flow activator comprises one or more needles.

3. The method of claim 1, wherein the fluid transporter has an opening, and wherein the inlet is positioned such that at least a portion of the inlet is positioned within about 0.7 millimeters of the opening of the fluid transporter.

4. The method of claim 1, wherein the flow activator comprises one or more needles or microneedles.

5. The method of claim 1, wherein the fluid transporter has a volume of no more than about 2 ml when the device is positioned against the skin of the subject.

6. The method of claim 1, further comprising a seal arranged to control a fluid communication pathway between the vacuum source and the fluid transporter.

7. The method of claim 1, wherein the vacuum source comprises a vacuum chamber having a pressure less than ambient pressure prior to introduction of a bodily fluid from the subject into the device.

8. The method of claim 7, wherein the vacuum chamber has a pressure, prior to introduction of a bodily fluid from the subject into the device, that is less than about 100 mmHg below ambient pressure.

9. The method of claim 1, wherein the groove comprises a capillary.

10. The method of claim 9, wherein the capillary comprises a curved flow path.

11. A method of receiving bodily fluid from a subject, the method comprising:
    applying, to the skin of a subject, a device comprising a fluid transporter having an opening, a recess and a flow activator, a channel having an inlet in fluid communication with the recess, and a vacuum source having a reduced pressure less than ambient pressure, the fluid transporter positioned to collect bodily fluid on the skin of the subject that is released by the flow activator;
    opening fluid communication between the recess and the vacuum source;
    receiving a bodily fluid into the recess and into a groove positioned in the recess, the groove forming a flow path along a surface that defines the recess, and the groove being in fluid communication with the inlet;
    blocking the inlet with at least a portion of the bodily fluid;
    increasing a pressure within the recess relative to a pressure in the vacuum source; and
    moving the bodily fluid from the groove into the channel towards the vacuum source due to a difference in pressure between the recess and the vacuum source.

12. The method of claim 11, wherein the inlet is positioned such that at least a portion of the inlet is positioned within about 0.7 millimeters of the opening of the fluid transporter.

13. The method of claim 11, wherein the flow activator comprises one or more needles or microneedles.

14. The method of claim 11, wherein the fluid transporter has a volume of no more than about 2 ml when the device is positioned against the skin of the subject.

15. The method of claim 11, further comprising a seal arranged to control a fluid communication pathway between the recess and the vacuum source.

16. The method of claim 11, wherein the vacuum source comprises a vacuum chamber having a pressure less than ambient pressure prior to introduction of a bodily fluid from the subject into the device.

17. The method of claim 16, wherein the vacuum chamber has a pressure, prior to introduction of a bodily fluid from the subject into the device, that is less than about 100 mmHg below ambient pressure.

18. The method of claim 11, wherein the inlet is positioned such that at least a portion of the inlet is positioned within a distance to the opening of about 10% of a distance between the opening and a point within the fluid transporter perpendicularly furthest away from the opening.

19. The method of claim 11, wherein the fluid transporter and the opening together define a first volume, the vacuum source has a second volume, and a volumetric ratio of the first volume to the second volume is at least about 1:6.

20. The method of claim 11, wherein the fluid transporter and the opening together define a first volume that is less than about 10 ml.

21. The method of claim 11, wherein the vacuum source has a second volume that is less than about 10 ml.

* * * * *